United States Patent
Calakos et al.

(10) Patent No.: US 11,285,142 B2
(45) Date of Patent: *Mar. 29, 2022

(54) COMPOSITIONS AND METHODS FOR IDENTIFYING AND TREATING DYSTONIA DISORDERS

(71) Applicants: DUKE UNIVERSITY, Durham, NC (US); THE UNITED STATES OF AMERICA, AS REPRESENTED BY THE SECRETARY DEPARMENT OF HEALTH AND HUMAN SERVICES, Bethesda, MD (US)

(72) Inventors: Nicole Calakos, Chapel Hill, NC (US); Zachary F. Caffall, Durham, NC (US); Joseph Rittiner, Durham, NC (US); Min Shen, Boyds, MD (US); Jennifer T. Fox, Rockville, MD (US); Zhuyin Li, Wallingford, CT (US)

(73) Assignees: The United States of America, as Represented by the Secretary, Department of Health and Human Services, Bethesda, MD (US); Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/764,320

(22) PCT Filed: Sep. 29, 2016

(86) PCT No.: PCT/US2016/054513
§ 371 (c)(1),
(2) Date: Mar. 29, 2018

(87) PCT Pub. No.: WO2017/059118
PCT Pub. Date: Apr. 6, 2017

(65) Prior Publication Data
US 2018/0271929 A1    Sep. 27, 2018

Related U.S. Application Data

(60) Provisional application No. 62/317,046, filed on Apr. 1, 2016, provisional application No. 62/234,127, filed on Sep. 29, 2015.

(51) Int. Cl.
| | | |
|---|---|---|
| A61K 31/47 | (2006.01) |
| C12Q 1/6883 | (2018.01) |
| G01N 33/68 | (2006.01) |
| C12Q 1/68 | (2018.01) |
| A61K 31/17 | (2006.01) |
| A61K 31/4706 | (2006.01) |
| A61P 25/14 | (2006.01) |
| A61K 31/4725 | (2006.01) |
| A61K 38/05 | (2006.01) |
| A61K 31/427 | (2006.01) |
| A61K 31/472 | (2006.01) |
| A61K 31/497 | (2006.01) |
| A61K 31/513 | (2006.01) |

(52) U.S. Cl.
CPC .............. *A61K 31/47* (2013.01); *A61K 31/17* (2013.01); *A61K 31/427* (2013.01); *A61K 31/472* (2013.01); *A61K 31/4706* (2013.01); *A61K 31/4725* (2013.01); *A61K 31/497* (2013.01); *A61K 31/513* (2013.01); *A61K 38/05* (2013.01); *A61P 25/14* (2018.01); *C12Q 1/68* (2013.01); *C12Q 1/6883* (2013.01); *G01N 33/6893* (2013.01); *C12Q 2600/118* (2013.01); *C12Q 2600/158* (2013.01); *G01N 2800/2835* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,744,305 A | 4/1998 | Fodor et al. |
| 6,313,296 B1 | 11/2001 | Sham et al. |
| 2005/0131017 A1 | 6/2005 | Degoey et al. |
| 2006/0160866 A1 | 7/2006 | Wong et al. |
| 2008/0096202 A1 | 4/2008 | Popko et al. |
| 2011/0142799 A1 | 6/2011 | Glimcher et al. |
| 2013/0116215 A1 | 5/2013 | Coma et al. |
| 2018/0289691 A1* | 10/2018 | Calakos ................. A61K 31/17 |

FOREIGN PATENT DOCUMENTS

| | | |
|---|---|---|
| WO | 1999/32619 | 7/1997 |
| WO | 1999/07409 | 2/1999 |
| WO | 2000/01846 | 1/2000 |
| WO | 2000/44895 | 8/2000 |
| WO | 2000/44914 | 8/2000 |
| WO | 2001/29058 | 4/2001 |
| WO | 2001/36646 | 5/2001 |

OTHER PUBLICATIONS

Kelly "Extrapyramidal symptoms with ritonavir/indinavirplus risperidone." Ann Phannacolher. May 2002;36(5):827-30. (abstract only) (Year: 2002).*
Solomons "Acute Extrapyramidal Dysfunction in Two HIV-infected Children" Journal of Tropical Pediatrics, vol. 57, No. 3 (Year: 2011).*
Reyes "Reversible movement disorders due to toxoplasmosis as initial manifestation of HIV-AIDS, with sequential MR and video imaging" Reyes AJ, et al. BMJ Case Rep (Year: 2016).*
(Continued)

*Primary Examiner* — Adam Weidner
(74) *Attorney, Agent, or Firm* — Polsinelli PC

(57) ABSTRACT

The present disclosure provides methods and compositions for the treatment, identification, diagnosis, and prognosis of dystonia, or dystonia related disorders.

14 Claims, 28 Drawing Sheets

(56) References Cited

OTHER PUBLICATIONS

Moccia "Movement Disorders as presenting symptoms of AIDS" Basal Ganglia 3(3) (Year: 2013).*
Factor "Dystonia in AIDS: Report of Four Cases" Movement Disorders vol. 18, No. 12, (Year: 2003).*
Webb "The ART of HIV therapies: dopaminergic deficits and future treatments for HIV pediatric encephalopathy" Expert Rev Anti Infect Ther. Mar. 2009 ; 7(2): 193-203 (Year: 2009).*
Rarediseases "Dystonia" accessed from rarediseases.org on Feb. 14, 2020 (Year: 2019).*
Gills "Nelfinavir,A Lead HIV Protease Inhibitor, Is a Broad-Spectrum, Anticancer Agent that Induces Endoplasmic Reticulum Stress,Autophagy, andApoptosis In vitro and In vivo" Clin Cancer Res;13(17) (Year: 2007).*
International Search Report for PCT/US2016/54506, dated Feb. 16, 2017.
International Search Report for PCT/US2016/54513, dated Feb. 3, 2017.
Andreev, D. E. et al., "Translation of 5' leaders in pervasive in genes resistant to eIF2 repression," (2015) Elife 4, e03971.
Barrows N.J., et al., "Factors affecting reproducibility between genome-scale siRNA-based screens," (2010) J. Biomol. Screen. 15, 735-47.
Barrows, N.J. et al.,"Functional genomics approach for the identification of human host factors supporting dengue viral propagation," (2014) Methods Mol. Biol. 1138, 285-99.
Bass, "The Short Answer," 2001, Nature 411: 428-429.
Boyce, M. et al., "A selective inhibitor of eIF2[alpha] dephosphorylation protects cells from ER stress," (2005) Science 307, 935-9.
Bragg et al. 2004, "Perinuclear biogenesis of mutant torsin-A inclusions in cultures cells infected with tetracycline-regulates herpes simplex virus type 1 amplicon vectors," Neuroscience 125, 651-61.
Bragg, D. C., et al., "Molecular pathways in dystonia," (2011) Neurobiol. Dis. 42, 136-47.
Calakos et al. "Functional evidence implicating a novel TOR1A mutation in idiopathic, late-inset focal dystonia," 2010, J Med Genet. 47, 646-50.
Camargos, S. et al., (2008), "DYT16, a novel young-onset dystonia-parkinsonism disorder: identification of a segregating mutation in the stress-response protein PRKRA," Lancet. Neural. 7, 207-15.
Cao, S. et al. (2010) "Chemical enhancement of torsinA function in call and animal models of torsion dystonia," Dis. Model. Mech. 3, 386-96.
Chen, P. et al. (2010), "The early-onset torsion dystonia-associated protein, torsinA, is a homeostatic regulator of endoplasmic reticulum stress reponse," Hum. Mol. Genet. 19, 3502-15.
Costa-Mattioli and Sonenberg, 2006, "eIF2[alpha] phosphorylation bidirectionally regulates the switch from short-to long-term synaptic plasticity and memory," Crit. Rev. Neurobiol. 18, 187-95.
Costa-Mattioli et al., 2007, "translational control of long-term synaptic plasticity and memory storage by eIF2[alpha]," Cell 129, 195-206.
Dang, NI. T. et al., (2005), "Generation and characterization of Dyt1 [delat]GAG knock-in mouse as a model for early-onset dystonia," Exp. Neural 196, 452-63.
Di Prisco et al., 2014, "Translational control of mGluR-dependent long-term depression and object-place learning by eIF2[alpha]," Nat. Neurosci. 17, 1073-82.
Elbashir et al., 2001, "Duplexes of 21-nucleotide RNAs mediate RNA interference in cultured mammalian cells," Nature 411: 494-498.
Frank, C. L., (2010), "Control of activating transcription Factor 4 (ATF4) persistence by multisite phosphorylation impacts cell cycle progression and neurogenesis," J Bioi. Chem. 285, 33324-33337.
Fullwood, M. J., et al., (2012), "Targetingn phosphorylation of eukaryotic initiation Factor-2[alpha] to treat human disease," Prog. Mol. Biol. Transl. Sci. 106, 75-106.

Gassart et al., (2015), "An inhibitor of HIV-1 protease modulates constitutive eIF2[alpha] dephosphorylation to trigger a specific integrated stress response," PNAS 113 (2) E117-E126.
Giles et al. 2008, "Dystonia-associated mutations cause premature degradation of TorsinA protein and cell-type-specific mislocalization to the nuclear envelope," Hum. Mol. Genet. 17, 2712-22.
Gonzalez-Alegre et al. 2004, "Aberrant cellular behavior of mutant TorsinA implicates nuclear envelope dysfunction in DYT1 dystonia," J Neurosci. 24, 2593-601.
Goodchild et al. 2004, "Mislocalization to the nuclear envelope:an effect of the dystonia-causing torsinA mutation," Proc. Natl. Acad Sci. USA 101, 847-52.
Goodchild, et al. 2005, "The AAA+ protein torsinA interacts with a conserved domain present in LAP1 and a novel ER protein," J Cell Biol. 168, 855-62.
Goodchild, R. E., et al,. (2005) "Loss of the dystonia-associated protein TorsinA selectively disrupts the neuronal nuclear enevelope ," Neuron 48, 923-32.
Harding, H. P. et al., (2000), "Regulated Translation Initiation Controls Stress-Induced Gene Expression in Mammalian Cells," Mol. Cell 6, 1099-108.
Harding, H. P. et al., (2003) "An integrated stress response regulated amino acid metabolism and resistance to oxidative stress," Mol. Cell 11, 619-33.
Hewett et al. 2000, "Mutant torsinA, responsible for early-onset torsin dystonia, form membrane inclusions in cultured neural cells," Hum. Mol. Genet. 9, 1403-13.
Hewett et al., 2008, "siRNA knock-down of mutant torsinA restores processing through secretory pathway in DYT1 dystonia cells," Hum. Mol. Genet. 17, 1436-45.
Hewett, et al., (2007), "Mutant torsinA interfers with protein processing through the secretory pathway in DYT1 dystonia cells," Proc. Natl. Acad. Sci. USA. 104, 7271-6.
Hinnebusch, A. G. & Lorsch, J. R., (2012), "The mechanism of eukaryotic translation: new insights and challenges," Cold Spring Harb. Perspect. Biol. 4.
Inglese, J., et al. (2006), "Quantitative high-throughput screening: a titration-based approach that efficiently identifies biological activities in large chemical libraries," PNAS, 103: 11473-11478.
Jackson, R. J., et al., (2010) "The mechanism of eukaryotic translation initiation and principles of its regulation," Nat. Rev. Mol. Cell Biol. 11, 113-27.
Jokhi et al., 2013, "Torsin mediates primary envelopment of large ribonucleoprotein granules at the nuclear envelope," Cell Rep. 3, 988-95.
Jungwirth, M, et al., (2010) "relative tissue expression of homologous torsinB correlates with the neuronal specific importance of DYT1 dystonia-associated torsinA," Hum. Mol. Genet. 19, 888-900.
Kim, C.E., et al., (2010) "A molecular mechanism underlying the neural-specific defect in torsinA mutant mice," Proc. Natl. Acad Sci. USA 107: 9861-6.
Kock et al. 2006, "Effects of genetic variations in the dystonia protein torsinA: identification of polymorphism at residue 216 as protein modifier," Hum. Mol. Genet. 15, 1355-64.
Kustedjo et al. 2000, "Torsin A and its Torsin dystonia-associated mutant form are lumenal glycoproteins that exhibit distinct subcellular localization," J Biol. Chem. 275, 27933-9.
Lassot, I. et al., (2001) "ATF4 degradation relies on a phosphorylation-dependent interaction with SCF ubiquitin ligase," Mol. Cell. Bioi. 21, 2192-202.
Liang et al. 2014, "Torsin A hypofunction causes abnormal twisting movements and sensorimotor circuit neurodegeneration," J Clin. Invest. 124, 3080-92.
Marciniak, S. J. & Ron, D, (2006) "Endoplasmic reticulum stress signaling in disease," Physiol. Rev. 86, 1133-49.
Martella et al., 2009, "Impairment of bidirectional synaptic plasticity in the striatum of a mouse model of DYT1 dystonia: role of endogenous acetylcholine," Brain 132, 2336-19.
Martella et al., 2014, "Regional specificity of synaptic plasticity deficits in a knock-in mouse model of DYT1 dystonia," Neurobiol. Dis. 65, 124-32.

(56) References Cited

OTHER PUBLICATIONS

Martin, et al. 2009, "Transcriptional and proteomic profiling in a cellular model of DYT1 dystonia," Neuroscience 164, 563-72.
Naismith et al. 2004, "TorsinA in the nuclear envelope," Proc. Natl. Acad Sci. USA 101, 7612-7.
Nery, F. C. et al. (2011) "TorsinA participates in endoplasmic reticulum-associated degradation," Nat. Commun. 2, 393.
Nolan et al., 2002, "Suspension array technology: evolution of the flat-array paradigm," Trends Biotechnol. 20(1): 9-12.
Ozelius et al., 1997, "The early-onset torsin dystonia gene (DYT1) encodes an ATP-binding protein," Nat. Genet. 17, 40-8.
Panda, D. et al. (2011), "RNAi screening reveals requirement for the host cell secretory pathway in infection by diverse families of negative-strand RNA viruses," Proc. Natl. Acad Sci. US. A. 108, 19036-41.
Patil, C. & Walter, P., (2001) "Intracellular signalling from the endoplasmic reticulum to the nucleus: the unfolded protein response in yeast and mammals," Curr. Opin. Cell Biol. 13, 349-55.
Peterson et al., 2010, "Convergent evidence for abnormal stratal synaptic plasticity in dystonia," Neurobiol Dis. 37, 558-73.
Seibier, P. et al. (2008), "A heterozygous frameshift mutation in PRKRA (DYT16) associated with generalised dystonia in a German patient," Lancet. Neural. 7, 380-1.
Sidrauski, C. et al., (2013), "pharmacological brake-release of mRNA translation enhances cognitive memory," Elife 2, e00498.
Stockwell, S. R. et al., (2012), "Mechanism-based screen for G1/S checkpoint activators identifies a selective activator of EIF2AK3/PERK signalling," PloS One 7, e28568.
Tanabe, L. M., et al., (2012), "Genetic background modulates the phenotype of a mouse model of DYT1 dystonia," PloS One 7, e32245.
Trinh and Klann, 2013, "Translational control by eIF2[alpha] kinases in long-lasting synaptic plasticity and long-term memory," Neurobiol. Learn. Mem. 105, 93-9.
Trusel et al., 2015, "Coordinated regulation og synaptic plasticity at striatopallidal and striatonigral neurons orchestrates motor control," Cell Rep. 13, 1353-65.
Tsaytler, P., et al., (2011), "slelective inhibition of a regulatory subunit of protein phosphatase 1 restores proteostasis," Science 332, 91-4.
Vander Heyden et al. 2009, "LULL1 retargets TorsinA to the nuclear envelope revealing an activity that is impaired by the DYT1 dystonia mutation," Mol. Biol. Cell 20, 2661-72.
Vattem, K. M. & Wek, R. C., (2004), "Reinitiation involving upstream ORFs regulates ATF4 mRNA translation in mammalian cells," Proc. Natl. Acad Sci. USA 101, 11269-74.
Vaughn, L. S. et al., (2015), "Altered activation f protein kinase PKR and enhanced apoptosis in dystonia cells carrying a mutation in PKR activator protein PACT," J Bioi. Chem.290, 22543-57.
Vulinovic et al. 2014, "Unraveling cellular phenotypes of novel TorsinA/TOR1A mutations," Hum. Mutat. 35, 1114-22.
Waugh, J. L. & Sharma, N., (2013), "Dystonia from phenotype to genotype," Neurol. Clin. 31, 969-86.
Zech, M., et al., (2015), "reply to letter: Novel compound Heterzygous mutations in PRKRA cause pure Dystonia," Mov Disord 30, 878-9.
Adachi et al., "Structure of HIV-1 protease in complex with potent inhibitor KNI-272 determined by high-resolution X-ray and neutron crystallography." Proc Natl Acad Sci USA, 106(12):4641-6 (Mar. 2009).
Shashidharan et al., "Transgenic mouse model of early-onset DYT1 dystonia." Hum Mol Genet., 14(1):125-33 (Jan. 2005).
Houlden et al., "THAP1 mutations (DYT6) are an additional cause of early-onset dystonia." Neurology, 74(10):846-50 (Mar. 2010).
International Preliminary Report on Patentability for PCT/US2016/54506, dated Apr. 3, 2018.
Written Opinion for PCT/US2016/54506, dated Feb. 16, 2017.
International Preliminary Report on Patentability for PCT/US2016/54513, dated Apr. 3, 2018.
Written Opinion for PCT/US2016/54513, dated Feb. 3, 2017.

\* cited by examiner c

| Gene Name | Variant ID | Function |
|---|---|---|
| AMDHD2 | 16:2577907-C/T | START_GAINED |
| ATF4 | 22:39917587-C/T | NON_SYNONYMOUS_CODING |
| CATSPERD | 19:5727283-G/A | NON_SYNONYMOUS_CODING |
| CDK10 | 16:89753080-C/T | START_GAINED |
| CHRDL2 | 11:74441891-C/T | NON_SYNONYMOUS_CODING |
| CYP1A1 | 15:75014027-A/G | NON_SYNONYMOUS_CODING |
| CYP1A1 | 15:75014727-G/A | NON_SYNONYMOUS_CODING |
| DOLK | 9:131708504-T/C | NON_SYNONYMOUS_CODING |
| L3MBTL2 | 22:41605776-G/C | NON_SYNONYMOUS_CODING |
| RSRC2 | 12:122990229-A/C | NON_SYNONYMOUS_CODING |
| SULT2B1 | 19:49079224-G/A | NON_SYNONYMOUS_CODING |
| WDR90 | 16:705854-G/A | STOP_GAINED |
| ZNF138 | 7:64291333-T/A | NON_SYNONYMOUS_CODING |
| ZNF138 | 7:64291333-T/G | NON_SYNONYMOUS_CODING |

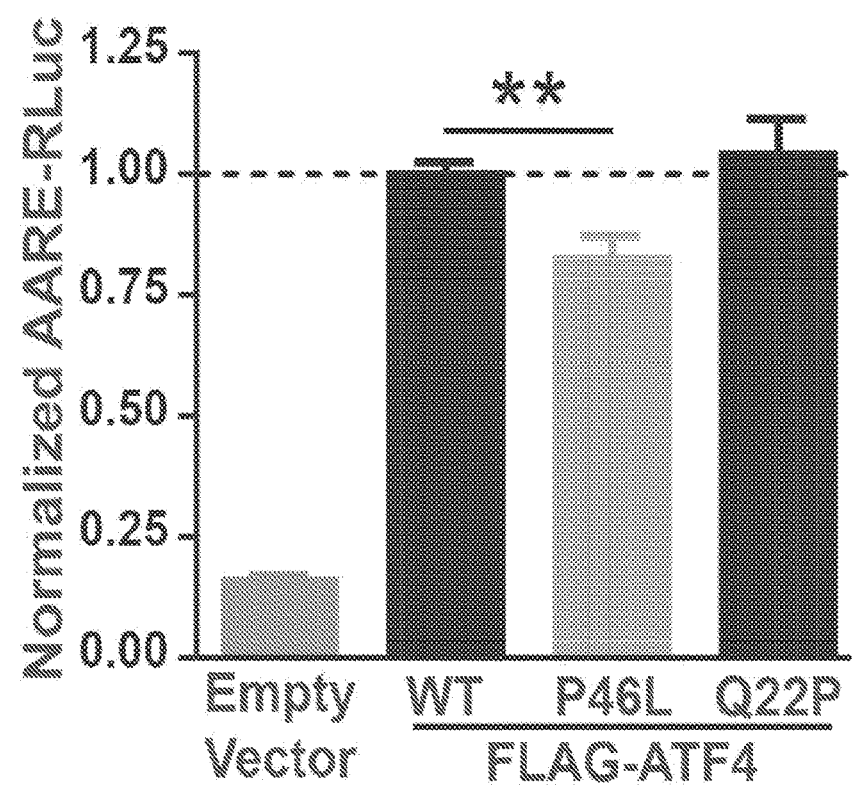

| ATF4 | | Variant Allele Frequency | | |
|---|---|---|---|---|
| Variant | Impact | Dystonia | Control | Enrichment |
| *Rare* | | | | |
| c.1A>G | p.M1V | 0.21% | 0.0032% | 65.6x |
| c.103G>A | p.D35N | 0.63% | 0% | N/A |
| c.103G>T | p.D35Y | 0.21% | Novel | N/A |
| c.137C>T | p.P46L | 0.63% | 0.2% | 3.2x |
| *Common* | | | | |
| c.65A>C | p.Q22P | 31.2% | 30.7% | 1.02x |

Figure 6 a

COMPOSITIONS AND METHODS FOR IDENTIFYING AND TREATING DYSTONIA DISORDERS

CROSS-REFERENCE TO RELATED APPLICATIONS

This application is a U.S. national phase application of International Patent Application No. PCT/US16/54513, filed on Sep. 29, 2016, which claims the benefit of U.S. provisional application No. 62/234,127, filed Sep. 29, 2015, and U.S. provisional application No. 62/317,046, filed Apr. 1, 2016 all of which are incorporated herein by reference in their entirety.

NAMES OF THE PARTIES TO A JOINT RESEARCH AGREEMENT

Duke University and the United States of America, as Represented by the Secretary, Department of Health and Human Services, Office of Technology Transfer, National Institutes of Health are parties to a Joint Research Agreement.

BACKGROUND OF THE INVENTION

Field of the Invention

The present invention relates to the diagnosis, prognosis, and treatment of dystonia and dystonia related disorders.

DESCRIPTION OF RELATED ART

Dystonia is a movement disorder characterized by sustained, often painful involuntary postures, causing patients motor disability and a marked decrease in quality-of-life. As a class of disorders, dystonia is the 3rd most common movement disorder behind Parkinson and essential tremor, and is present as a symptom in a broad range of clinical contexts (e.g. sporadic, neurodegeneration, trauma, medication side effects). Once symptoms onset, they are typically unremitting, creating a substantial quality of life impairment and disease burden. Importantly, the therapeutic armamentarium for dystonia is severely limited.

DYT1 early-onset torsion dystonia is a severe, childhood-onset form of dystonia. DYT1 dystonia is caused by an in-frame trinucleotide deletion in the TOR1A gene, leading to the loss of a single glutamic acid residue (delta-E) from the AAA+ATPase Torsin1a. (See, e.g., Ozelius et al., 1997, *Nat. Genet.* 17, 40-8.) Though the precise function of Torsin1a is unknown, the delta-E mutation has a dramatic effect in its subcellular localization. (See, e.g., Goodchild, et al. 2005, *J. Cell Biol.* 168, 855-62; Kustedjo et al. 2000, *J. Biol. Chem.* 275, 27933-9; Bragg et al. 2004, *Neuroscience* 125, 651-61; Calakos et al. 2010, *J. Med. Genet.* 47, 646-50; Gonzalez-Alegre et al. 2004, *J. Neurosci.* 24, 2593-601; Goodchild et al. 2004, *Proc. Natl. Acad. Sci. U.S.A* 101, 847-52; Hewett et al., 2008, *Hum. Mol. Genet.* 17, 1436-45; Kock et al. 2006, *Hum. MoL Genet.* 15, 1355-64; Hewett et al. 2000, *Hum. Mol. Genet.* 9, 1403-13; Vander Heyden et al. 2009, *Mol. Biol. Cell* 20, 2661-72; Goodchild et al. 2005, *J. Cell Biol.* 168, 855-62; Martin et al. 2009, *Neuroscience* 164, 563-72; Liang et al. 2014, *J. Clin. Invest.* 124, 3080-92; Giles et al. 2008, *Hum. Mol. Genet.* 17, 2712-22; Vulinovic et al. 2014, *Hum. Mutat.* 35, 1114-22.)

Normally, the wildtype (WT) Torsin1a cycles between the outer nuclear envelope (NE) and the lumen of the endoplasmic reticulum (ER) in an ATP hydrolysis-dependent fashion, with the bulk of the protein detected in the ER. See, e.g., Goodchild et al. 2004; Naismith et al. 2004, *Proc. Natl. Acad. Sci. U.S.A* 101, 7612-7. In contrast, when delta-E Torsin1a is the major species, as in overexpression experiments or homozygous knock-in mouse models, it predominantly co-localizes with nuclear envelope ("NE") markers and disrupts the normal subcellular NE membrane structure in a manner that is suggestive of a membrane-trafficking defect. (Goodchild et al, 2004; Naismith et al. 2004; Jokhi et al, 2013, *Cell Rep.* 3, 988-95.)

At the light microscopic level, delta-E Torsin1a distribution appears as an abnormal punctate pattern (see FIG. 1, panel a); an appearance that is in striking contrast to the diffuse reticular pattern of similarly expressed WT Torsin1a (see FIG. 1b). Because delta-E Torsin1a mis-localization is a robust, early phenotype associated with disruption of basic cellular architecture, it is possible that molecular pathways remediating delta-E Torsin1a mis-localization could serve as novel therapeutic targets for Dyt1 dystonia.

The etiology of other forms of inherited and sporadic dystonia are less clear or entirely unknown. Furthermore, current drug treatments are only symptomatic, of modest efficacy, and are poorly tolerated because of side effects (anticholinergics). Other treatment options are invasive and generally require access to tertiary care centers (deep brain stimulation, botulinum toxin).

Thus, there is a need in the art for methods of diagnosing and treating subjects suffering from inherited and sporadic forms of dystonia, including understanding the molecular basis of the disease. Furthermore, there is a need in the art to understand the basis for aberrant delta-E Torsin1a localization in DYT1 dystonia patients.

SUMMARY OF THE INVENTION

Against this backdrop, embodiments of the present disclosure address one or more of the above-identified needs, among others, recognized by those skilled in the art, and provide several benefits over existing clinical methods of identification, diagnosis, prognosis, and therapeutic intervention in, or treatment of, subjects with dystonia.

In embodiments, the disclosure provides methods of treating dystonia using an HIV aspartyl protease inhibitor. Examples include, but are not limited to, ritonavir, liponavir, saquinavir, nelfinavir, and indinavir. In some embodiments, an inhibitor of the disclosure is selected from ritonavir, liponavir, saquinavir, and combination thereof.

In some embodiments, the inhibitor of the disclosure is a compound of formula (I):

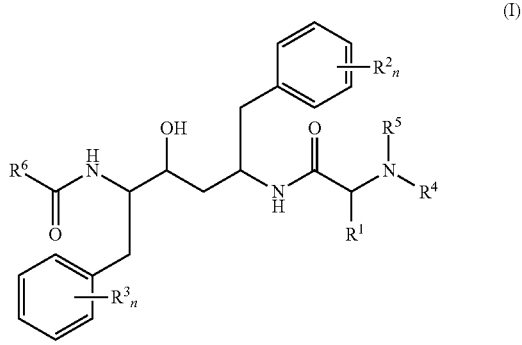

or pharmaceutically acceptable salts thereof, wherein
each n is independently selected from 0, 1, 2, 3, and 4;
$R^1$ is hydrogen or $C_1$-$C_6$ alkyl;
$R^2$ and $R^3$ are each independently selected from halogen, hydroxy, $C_1$-$C_6$ alkyl, and $C_1$-$C_6$ alkoxy; and
$R^4$ is —C(O)$R^8$, —C(O)O$R^8$, —C(O)NH$R^8$, or —C(O)N($C_1$-$C_6$ alkyl)$R^8$,
where $R^8$ is $C_1$-$C_6$ alkyl, aryl, heteroaryl, heterocyclyl, aryl$C_1$-$C_6$ alkyl-, heteroaryl$C_1$-$C_6$ alkyl-, or heterocyclyl$C_1$-$C_6$ alkyl-, each optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino;
$R^5$ is selected from hydrogen and $C_1$-$C_6$ alkyl,
or $R^5$ and $R^8$ together with atoms to which they are attached form heterocyclyl optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, di$C_1$-$C_6$ alkylamino, oxo, or thio; and
$R^6$ is —Z—$R^7$, wherein
Z is absent, —$C_1$-$C_6$ alkylene-, —O—$C_1$-$C_6$ alkylene-, —$C_1$-$C_6$ alkylene-O—, —NH—$C_1$-$C_6$ alkylene-, —$C_1$-$C_6$ alkylene-NH—, —O—, —NH—, or —N($C_1$-$C_6$ alkyl)-; and
$R^7$ is aryl, heteroaryl, or heterocyclyl, each optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino.

In other embodiments, compound of formula (I) is of formula (I-A):

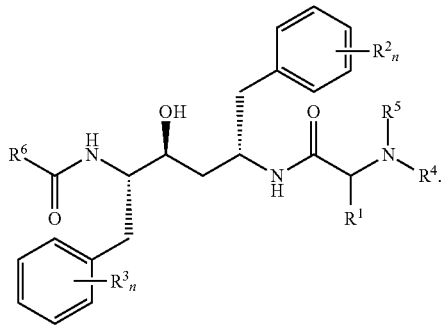

In further embodiments, the inhibitor of the disclosure is a compound of formula (II):

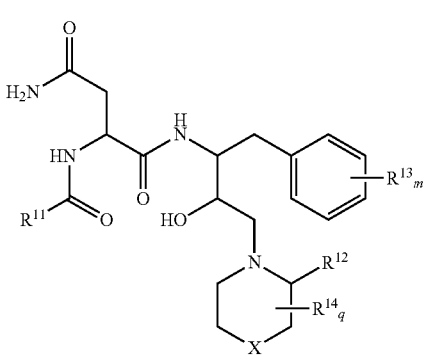

(II)

or pharmaceutically acceptable salts thereof, wherein
m is selected from 0, 1, 2, 3, and 4;
q is selected from 0, 1, 2, 3, and 4;
X is —O—, —NH—, —CH$R^{14}$—, —C($R^{14}$)$_2$—, or —CH$_2$—,
$R^{11}$ is aryl, heteroaryl, or heterocyclyl, each optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino;
$R^{12}$ is —C(O)$R^{15}$, —C(O)O$R^{15}$, —C(O)NH$R^{15}$, or —C(O)N($C_1$-$C_6$ alkyl)$R^{15}$,
where $R^{15}$ is $C_1$-$C_6$ alkyl, $C_2$-$C_6$ alkenyl, $C_2$-$C_6$ alkynyl, aryl, heteroaryl, heterocyclyl, aryl$C_1$-$C_6$ alkyl-, heteroaryl$C_1$-$C_6$ alkyl-, or heterocyclyl$C_1$-$C_6$ alkyl-, each optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino;
$R^{13}$ is each independently selected from halogen, hydroxy, $C_1$-$C_6$ alkyl, and $C_1$-$C_6$ alkoxy; and
$R^{14}$ is each independently selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino;
or two $R^{14}$ with atoms to which they are attached form heterocyclyl optionally substituted with one or more groups selected from halogen, cyano, nitro, $C_1$-$C_6$ alkyl, hydroxy, $C_1$-$C_6$ alkoxy, amino, $C_1$-$C_6$ alkylamino, di$C_1$-$C_6$ alkylamino, oxo, or thio.

Specific preferred embodiments of the present invention will become evident from the following more detailed description of certain preferred embodiments and the claims.

BRIEF DESCRIPTION OF THE DRAWINGS

The foregoing aspects and other features of the invention are explained in the following description, taken in connection with the accompanying drawings, in which.

DETAILED DESCRIPTION OF THE INVENTION

Figure 1:
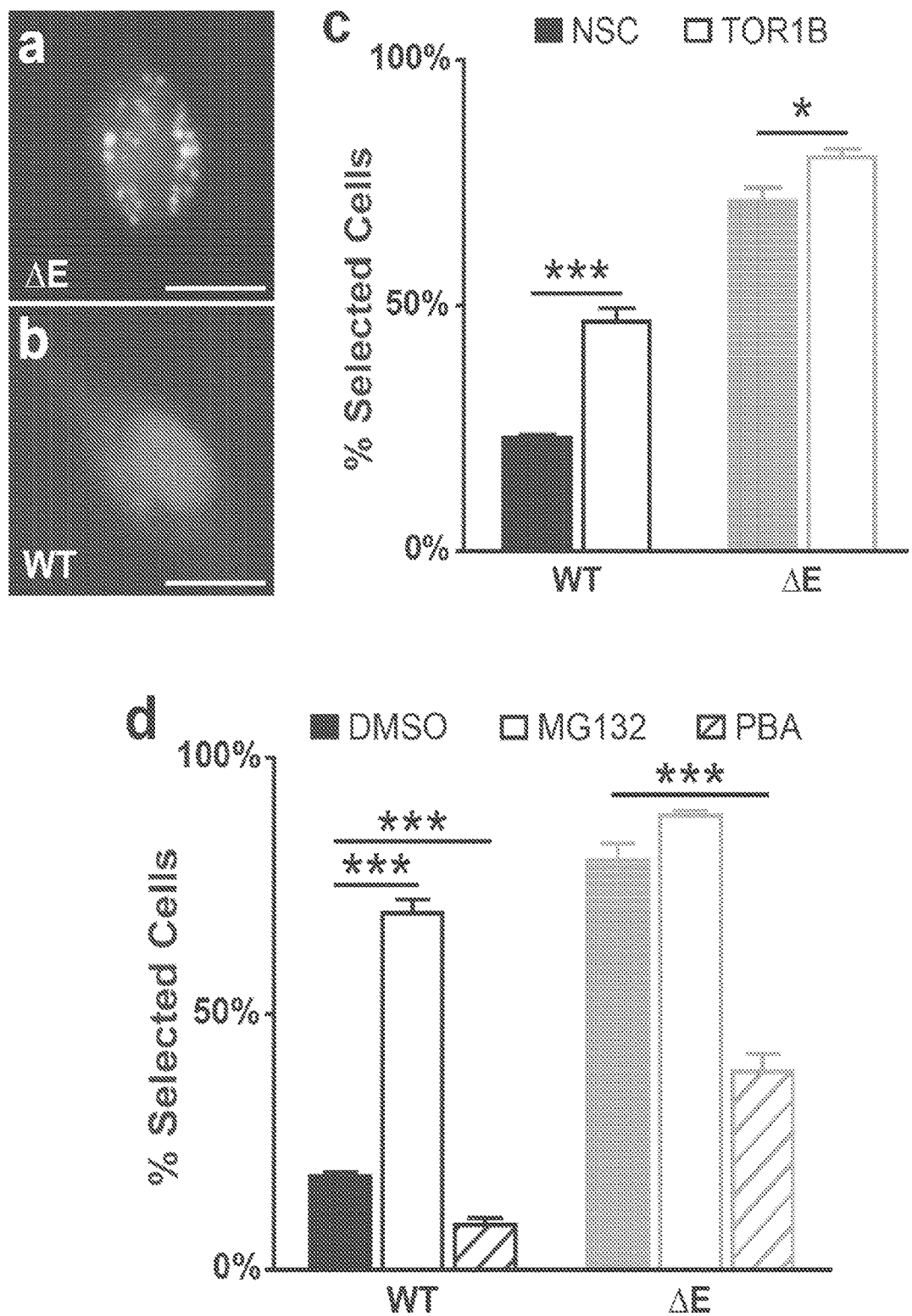
FIG. 1 shows results of delta-E ("ΔE") Torsin1a mis-localization assay and whole genome siRNA screen. Panels (a) and (b) show representative images of Flp-In T-REx 293T stable cell lines expressing delta-E (panel a) and wild-type ("WT") (panel b) EGFP-hTorsin1a following 72 h tetracycline induction (light punctate staining comprises EGFP-hTorsin1a signal; diffuse darker staining comprises Hoescht nuclear stain). Scale bars=10 μm. Panel (c) shows that silencing Torsin1b (TOR1B) worsens Torsin1a mis-localization in both WT and delta-E cell lines. Panel (d) shows that proteasomal inhibition with MG132 increases Torsin1a mis-localization, and the chemical "chaperone," phenylbutyric acid (PBA) reduces Torsin1a mis-localization. Panels (e)-(g) show representative low-magnification images of cell lines acquired under high-throughput screen conditions in 384-well plates following reverse transfection with control siRNAs. WT (panel e) and delta-E treated with non-silencing siRNA control (panel f) or with positive control siRNA (panel g). Scale bars=50 μm. Panel (h) shows assay reproducibility and siRNA pooling strategy. Inset—Four independent siRNAs targeting each gene were split into two unique pools of two siRNAs. Panel (i) shows results of a whole genome siRNA (WGS) screen. Dots represent data for individual gene targets, with results from each independent siRNA pool plotted on orthogonal axes. Panel (j) shows a schematic depicting WGS workflow for analyzing primary hits. Panel (k) shows performance of four of top 93 hits in counter screen to rescue deficient secretion in fibroblasts derived from human DYT1 patients relative to WT cells. All data are presented as means±S.E.M. * denotes p<0.05; *** denotes p<0.0005 by unpaired t test. Panel (I) shows strategy for site-specific integration of a single cDNA copy of EGFP-WT-Torsin1a or EGFP-deltaE-Torsin1a into Flp-In HEK 293 T-REx cells under control of a tetracycline-sensitive transcriptional repressor.
Figure 1:
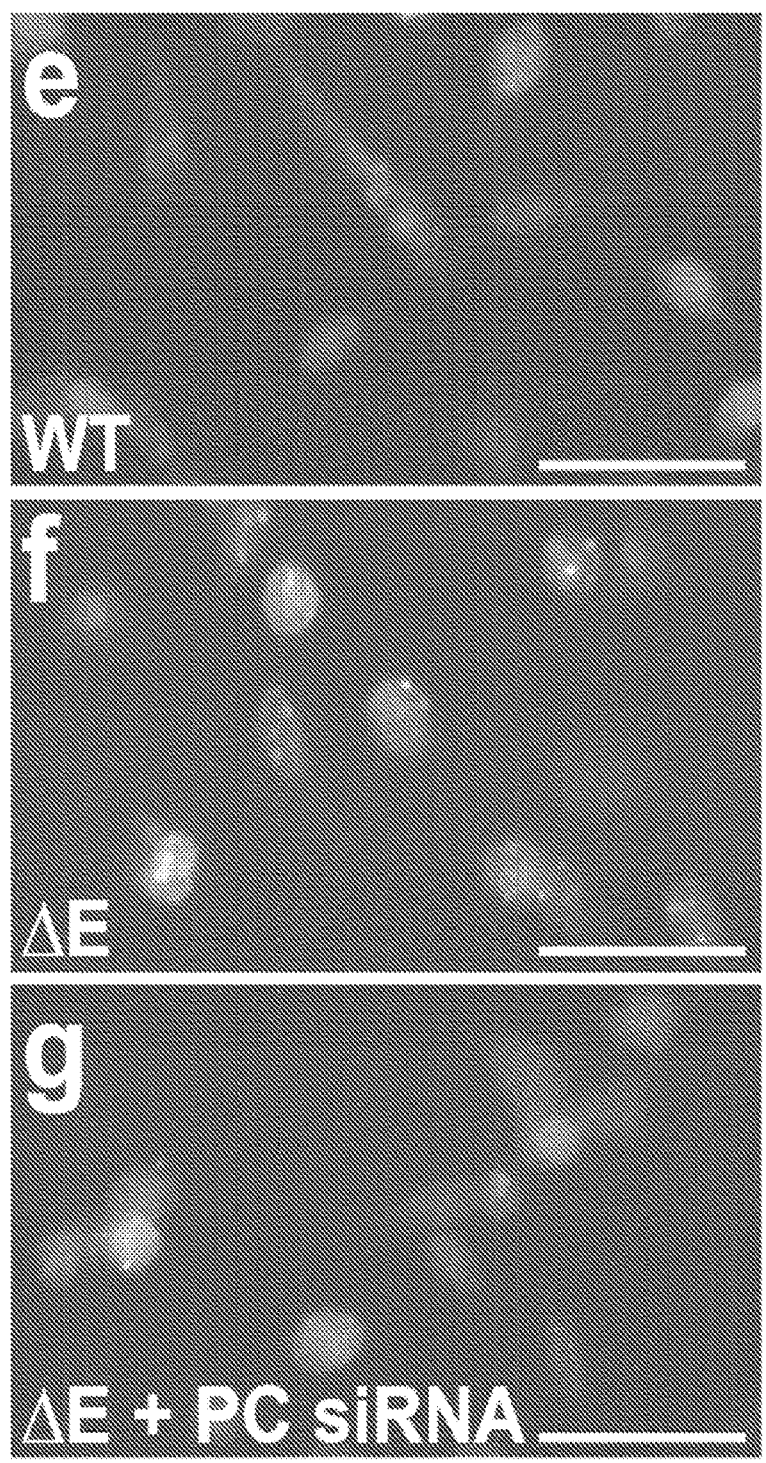
Figure 1:
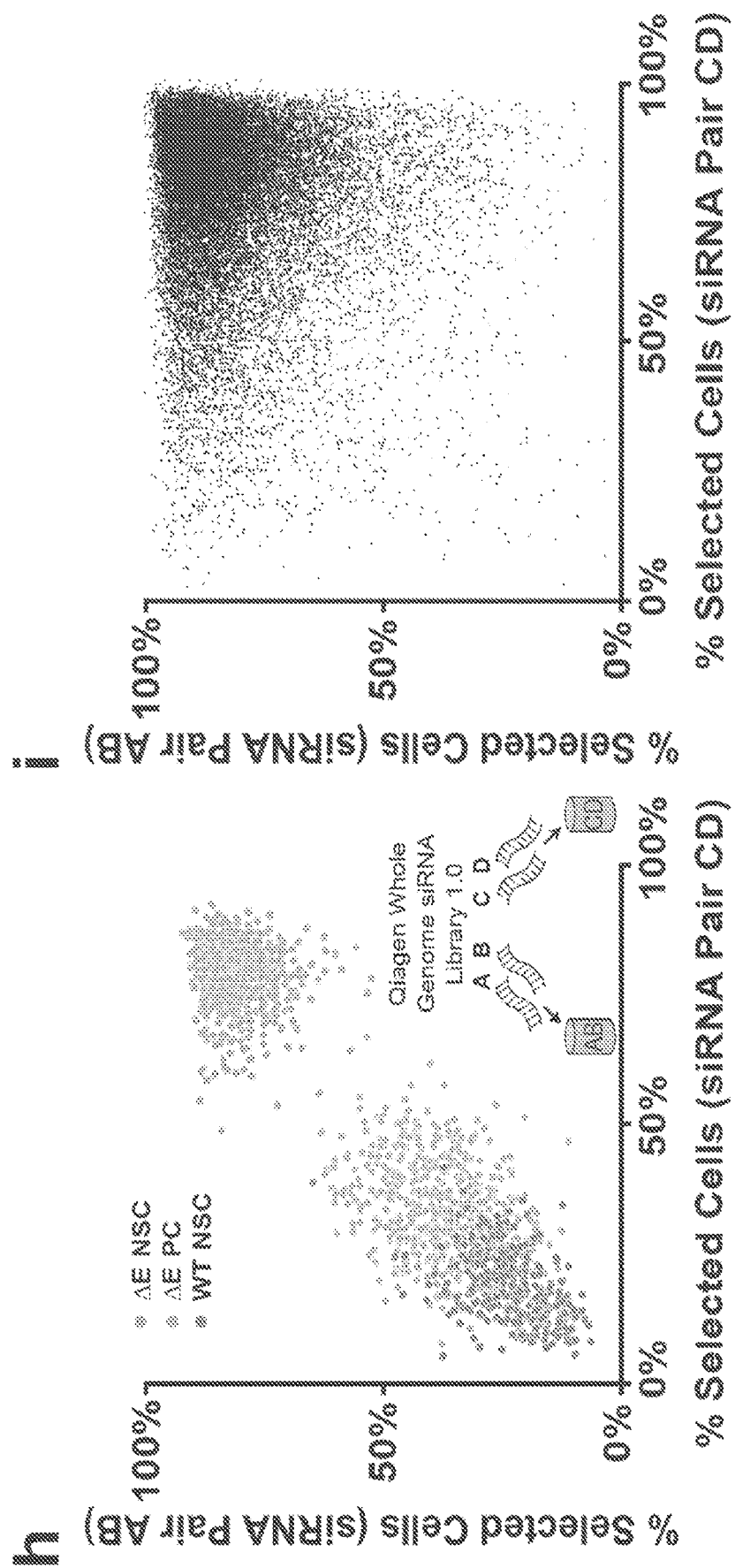
Figure 1:
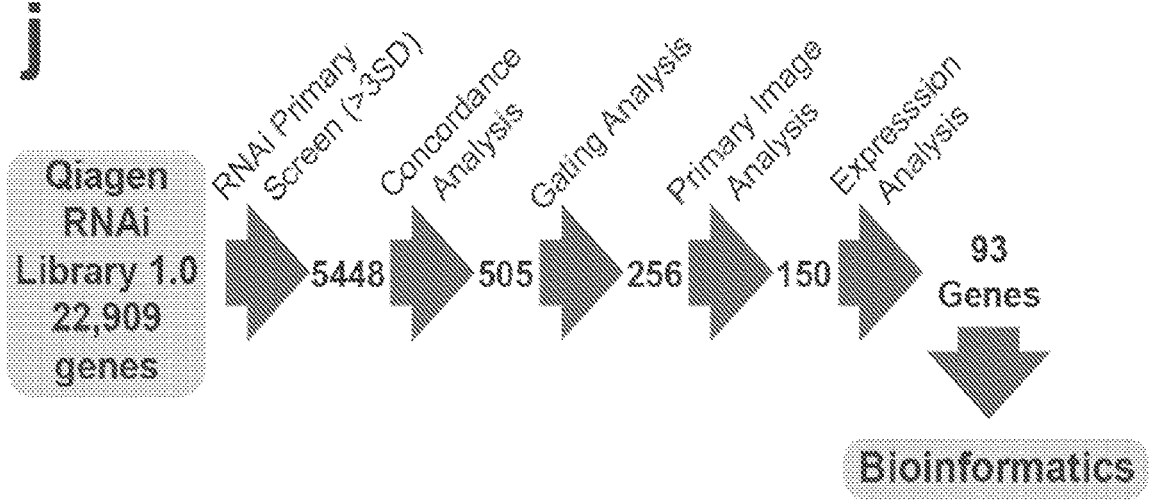
Figure 1:
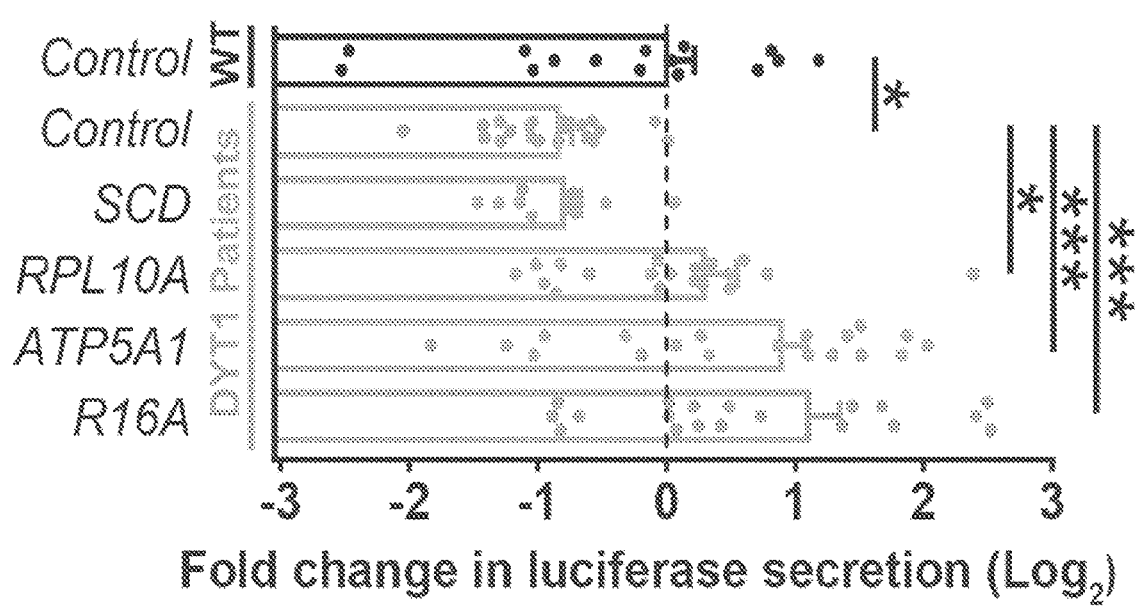
Figure 1:
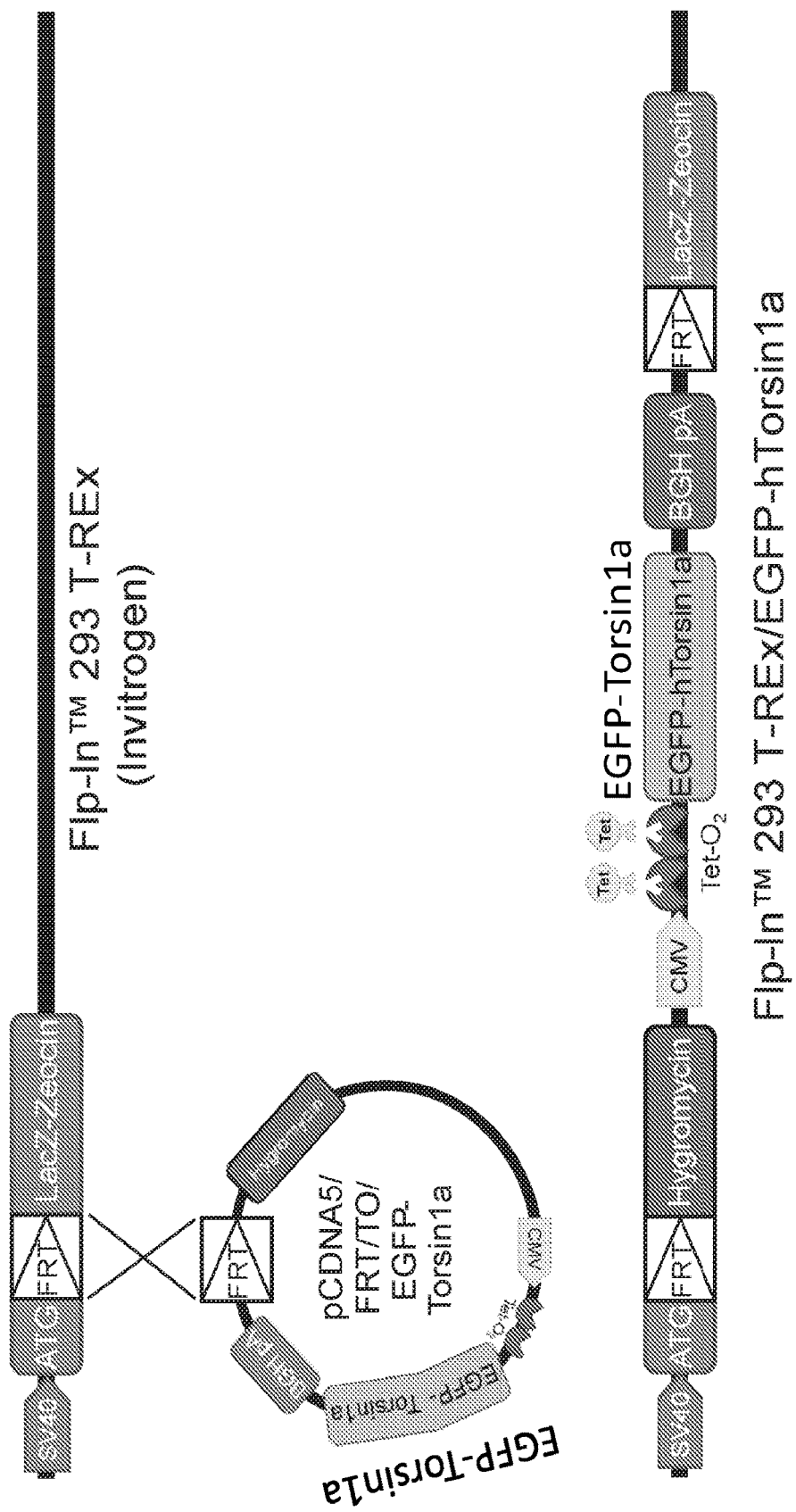

For the purposes of promoting an understanding of the principles of the present disclosure, reference will now be made to embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

The present disclosure provides methods and compositions for the treatment, identification, diagnosis, and prognosis of dystonia, or dystonia related disorders. In some embodiments, the disclosure provides compositions and methods for therapeutic intervention in subjects suffering from dystonia, or dystonia related disorders. In other embodiments, the disclosure provides methods and compositions for diagnosis or prognosis of subjects who are suffering from, or are likely to suffer from, dystonia, or dystonia related disorders. In still further embodiments, the present disclosure provides methods for diagnosing and treating subjects who are, or who may be, suffering from dystonia.

All publications, patents and patent applications cited herein are hereby expressly incorporated by reference for all purposes.

Methods well known to those skilled in the art can be used to practice embodiments of the present disclosure. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York; Sambrook, J. et al., 2001, "MOLECULAR CLONING: A LABORATORY MANUAL," 3.sup.rd edition, Cold Spring Harbor Laboratory Press. The contents of the above are incorporated in their entirety herein by reference.

Additional methods well known to those skilled in the art can be used to prepare pharmaceutically acceptable compositions and methods of treatment according to the present disclosure. See, for example, Goodman & Gilman, *The Pharmacological Basis of Therapeutics*, ($11^{th}$ Edition) 2005, McGraw-Hill. The contents of the above are incorporated in their entirety herein by reference.

Additional methods well known to those skilled in the art can be used for therapeutic intervention in subjects with dystonia disorders. (See e.g., Stacy, M., Ed., *Physician's Desk Reference*, Medical Economics Company, Inc. Montvale, N. J. ($54^{th}$ Edition) 2000.)

Before describing the disclosed methods and compositions in detail, a number of terms will be defined. As used herein, the singular forms "a", "an", and "the" include plural referents unless the context clearly dictates otherwise.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of this invention.

For the purposes of describing and defining this invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Definitions

In addition to terms defined elsewhere in the disclosure, the following definitions apply to the description of the embodiments herein:

As used herein, the term "dystonia" refers to those neurological conditions and brain disorders characterized by often painful twisting motions and postures and involuntary movements. Such conditions may be idiopathic, sporadic, or inherited forms with or without defined genetic causes.

As used herein, the term "patient" or "subject" refers to mammals, including humans, animal pets, farm animals, zoo animals, and the like. Further, the patient or subject of the present disclosure may refer to any vertebrate species. In some embodiments, the patient or subject is a human. In certain embodiments, the subject is a human patient that is at risk for, or suffering from, dystonia.

As used herein, the term "integrated stress response" refers to the common adaptive pathway eukaryotic cells activate in response to stress stimuli.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results. As used herein an "effective" amount or a "therapeutically effective amount" of a pharmaceutical ingredient refers to a nontoxic but sufficient amount of the ingredient to provide the desired effect. For example, one desired effect would be the prevention or treatment of dystonia or dystonia related disorders.

An amount that is "effective" according to embodiments of the disclosure will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

As used herein, the term active pharmaceutical ingredient (API) means a compound or compounds with the ability to modulate dystonia or dystonia symptoms in a subject in need thereof. In some embodiments, an API of present disclosure is capable of modulating the levels or activity of one or a plurality of genes or proteins selected from ATF4, BiP, eIF2-alpha, GADD34, and CreP.

As used herein, the term "agonist" is used in the broadest sense and includes any molecule that mimics a biological activity of a native polypeptide disclosed herein. An agonist can be any chemical compound, nucleic acid molecule, peptide or polypeptide can enhance activity of a gene product (e.g., by stabilizing the gene product, preventing its proteolytic degradation or increasing its enzymatic or binding activity or directly activating expression of a gene).

As used herein, the term "biological sample" or "biosample" or "sample" isolated from a subject includes, but is not limited to, a tissue or bodily fluid obtained from an animal, preferably a mammal and most preferably a human, containing tissues, cells, and/or biological fluids isolated from a subject. Examples of biological samples include, but are not limited to, tissues, cells, biopsies, blood, lymph, serum, plasma, cerebrospinal fluid, urine, feces, saliva, mucus and tears. In one embodiment, the biological sample is a blood sample (such as a plasma sample) or biopsy sample (such as a tissue/cell sample). A biological sample may be obtained directly from a subject (e.g., by blood or tissue sampling) or from a third party (e.g., received from an intermediary, such as a healthcare provider or lab technician). In some embodiments, a sample according to the disclosure is obtained from a human suspected of having, or previously diagnosed as having, or in need of screening for dystonia. In certain embodiments, a biological sample is a sample of blood or cerebrospinal fluid.

As used herein, the term "dystonia biomarker" refers to a naturally occurring biological molecule, or variant or mutation thereof, present in a subject at varying concentrations useful in predicting the risk or incidence of a disease, the aggressiveness of a disease or a condition, or the likelihood of developing and/or surviving a disease or condition, such as dystonia. For example, the biomarker can be mis-localization of a protein, such as ΔE Torsin1a, that is present in in a subject as compared to a control that indicates the presence of a disease, such as dystonia or likelihood of developing said disease/condition, such as dystonia.

As used herein "concentration" of a biomarker refers to both percent concentration and absolute concentration of the biomarker. "Percent concentration" refers to the comparative concentration of a biomarker with respect to another. "Absolute concentration" refers to a direct measurement of the biomarker without comparison to other detected species.

As used herein "pre-treatment level" or "pre-treatment range" refers to a level or concentration of one or more biomarkers (e.g. 1, 2, 3, 4, 5, or more biomarkers) in a biosample isolated from a subject before administering treatment for a disorder characterized by dystonia, or dystonia related disorders. A pre-treatment level or pre-treatment range includes, without limitation, an average of multiple measurements of the level or concentration of one or more biomarkers, or range of one or more biomarkers, based on multiple measurements from a subject.

The term "quantify" or "quantification" may be used interchangeable, and refer to a process of determining the quantity or abundance of a substance in a sample (e.g., a biomarker), whether relative or absolute. For example, quantification may be determined by methods including but not limited to, micro-array analysis, qRT-PCR, band intensity on a Northern or Western blot, Fluorescent in situ hybridization (FISH), or by various other methods known in the art. Any method of detection fails within the general scope of the present disclosure. The detection methods may be generic for the detection of proteins, phosphopeptides, nucleic acids, polypeptides and the like. The detection methods may be directed towards the scoring of a presence or absence of one or more biomarker molecules or may be useful in the detection of expression levels.

Methods of Treating or Preventing Dystonia

In embodiments, the present disclosure provides methods of treating a subject suffering from dystonia by administering one or more therapeutically effective agents that modulate the integrated stress response. In some embodiments, the present disclosure provides methods of treating a subject suffering from dystonia by administering one or more therapeutically effective agents that modulate the intracellular signaling pathway controlled by eIF2-alpha. In some embodiments, the present disclosure provides agents that modulate eIF2-alpha, either directly, or through modulation of other genes or proteins in the intracellular pathways of which eIF2-alpha is a component.

In some embodiments, methods of treating a subject suffering from dystonia according to the present disclosure comprise treating a subject with one or more agents that increase the phosphorylation state of the eIF2-alpha protein. In further embodiments, the one or more agents capable of increasing the phosphorylation state of eIF2-alpha comprises an agent that increases the kinase activity of eIF2-alpha-specific kinases, thereby increasing the phosphorylation state of eIF2-alpha. In other embodiments, the one or more agents capable of increasing the phosphorylation state of eIF2-alpha comprises an agent capable of inhibiting eIF2-alpha-specific phosphatases, thereby increasing the phosphorylation state of eIF2-alpha. In still other embodiments, the one or more agents capable of increasing the phosphorylation state of eIF2-alpha comprises an agent that acts upstream of eIF2-alpha-specific kinases, or eIF2-alpha-specific phosphatases, thereby increasing or inhibiting, respectively, their kinase or phosphatase activity toward eIF2-alpha.

In some embodiments, the present disclosure provides agents that mimic phosphorylated eIF2-alpha. In other embodiments, the present disclosure provides agents that mimic eIF2-alpha phosphorylated on Serine 51 of the human homolog of eIF2-alpha, or the corresponding residue on non-human homologs of eIF2-alpha.

In some embodiments, methods of treating a subject suffering from dystonia according to the present disclosure comprise treating a subject with one or more agents that modulate the steady state levels of eIF2-alpha protein in a cell. In certain embodiments, the one or more agents that modulate the steady state levels of eIF2-alpha protein in a cell regulate the expression of the eIF2-alpha gene, or the stability of the eIF2-alpha mRNA transcripts, or the rate of translation of eIF2-alpha mRNA transcripts. In other embodiments, the one or more agents that modulate the steady state levels of eIF2-alpha protein in a cell modulate the stability or turnover of the eIF2-alpha protein in a cell.

In some aspects, methods of treating a subject suffering from dystonia according to the present disclosure comprise treating a subject with one or more agents that modulate the phosphatase activity of the CreP protein toward its targets. In embodiments, methods of the present disclosure comprise one or more agents that directly modulate CreP phosphatase activity. In other embodiments, methods of the present disclosure comprise one or more agents that indirectly modulate CreP phosphatase activity. In certain embodiments, the activity of CreP is modulated at the level of protein or mRNA expression, such that the steady state levels of CreP in the cell are increased or reduced. In certain embodiments, the one or more agents that modulate the steady state levels of CreP protein in a cell regulate the expression of the CreP gene, or the stability of the CreP mRNA transcripts, or the rate of translation of CreP mRNA transcripts. In other embodiments, the one or more agents that modulate the steady state levels of CreP protein in a cell modulate the stability or turnover of the CreP protein in a cell. In some embodiments, methods of the present disclosure comprise one or more agents that modulate the phosphatase activity of CreP toward eIF2-alpha.

In further embodiments, the one or more agents capable of increasing the phosphorylation state of eIF2α according to the present method comprises salubrinal, Sal-003, or guanabenz.

In some embodiments, the one or more agents capable of increasing the phosphorylation state of eIF2α according to the present method comprises ritonavir, liponavir, saquinavir, nelfinavir, and indinavir. Those skilled in the art will recognize that agents according to the present disclosure are capable of increasing the cellular stress response. See, e.g., Gassart et al., (2015) PNAS 113 (2) E117-E126, incorporated herein in its entirety. Further, those skilled in the art will recognize that agents of the present disclosure modulate the phosphorylation state of the eIF2-alpha protein.

In some aspects, methods of treating a subject suffering from dystonia according to the present disclosure comprise treating a subject with one or more agents that modulate the activity of the ATF4 protein. In embodiments, methods of the present disclosure comprise one or agents that directly modulate ATF4 activity toward, for example, its transcriptional targets. In other embodiments, methods of the present disclosure comprise one or more agents that indirectly modulate ATF4 activity.

Accordingly, aspects of the disclosure provide compositions and methods for therapeutic intervention in subjects suffering from Dystonia or related disorders. In some embodiments, therapeutic intervention comprises additional dystonia therapies known in the art. For example, therapies for dystonia may include, but are not limited to, the following: (a) non-drug therapies, such as physical therapy, occupational therapy, speech and/or voice therapy, and relaxation/stress management; (b) oral medications, such as anticholinergics (e.g., trihexyophenidyl, benztmpine, ethopropazine, etc.), benzodiazepines (e.g., diazepam, clonazepam, lorazepam etc.), baclofen, dopaminergic agents/dopamine-depleting agents (e.g., levodopa, bromocriptine, clozapine, tetrabenazine, etc.), tetrabenezine and the like; (c) Botulinum Neurotoxin injections; (d) surgery, including deep brain stimulation, lesioning procedures (e.g., pallidotomy & Thalamotomy), peripheral surgeries, etc.) and complementary therapies, such as relaxation techniques, yoga, pilates, biofeedback, acupuncture, and the like. Such treatments are well known and particular to the patient and type of dystonia and can be readily determined by one skilled in the art. In some embodiments, an active pharmaceutical ingredient, or API, of the present disclosure comprises an interfering molecule. As used herein, the term "interfering molecule" refers to any molecule that is capable of disrupting, or inhibiting, an intracellular signaling pathway. In preferred embodiments, the interfering molecule is capable of disrupting the signaling pathway. An interfering molecule of the invention, for example, can inhibit the activity of a protein that is encoded by a gene either directly or indirectly. Direct inhibition can be accomplished, for example, by binding to a protein and thereby preventing the protein from binding an intended target, such as a receptor.

Indirect inhibition can be accomplished, for example, by binding to a protein's intended target, such as a receptor or binding partner, thereby blocking or reducing activity of the protein.

Furthermore, an interfering molecule of the invention can inhibit a gene by reducing or inhibiting expression of the gene, inter alia by interfering with gene expression (transcription, processing, translation, post-translational modification), for example, by interfering with the gene's mRNA and blocking translation of the gene product or by post-translational modification of a gene product, or by causing changes in intracellular localization.

Examples of suitable interfering molecules include, but are not limited to, small molecules, antibodies, antisense RNAs, cDNAs, dominant-negative forms of molecules such as, without limitation, ATF4, BiP, eIF2-alpha, GADD34, and CreP, protein kinase inhibitors, protease inhibitors, combinations thereof; and the like.

In certain embodiments, an inhibitor of the disclosure can be a small molecule inhibitor. As used herein, the term "small molecule" refers to a molecule that has a molecular weight of less than about 1500 g/Mol. A small molecule can be, for example, small organic molecules, peptides or peptide-like molecules. By way of example, a small molecule inhibitor suitable in methods of the disclosure can be salubrinal, Sal-003, or guanabenz.

In certain embodiments, an inhibitor of the disclosure can be an HIV aspartyl protease inhibitor. Examples include, but are not limited to, ritonavir, liponavir, saquinavir, nelfinavir, and indinavir. In some embodiments, an inhibitor of the disclosure is selected from ritonavir, liponavir, saquinavir, and combination thereof.

In some embodiments, the inhibitor of the disclosure is a compound of formula (I):

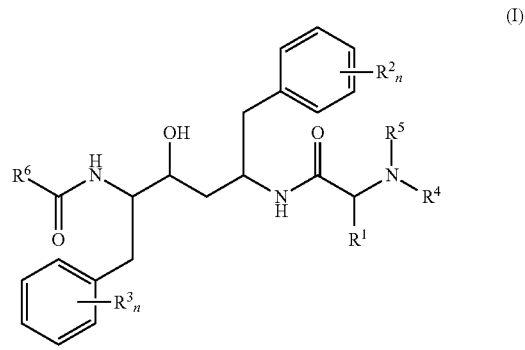

or pharmaceutically acceptable salts thereof, wherein
each n is independently selected from 0, 1, 2, 3, and 4;
$R^1$ is hydrogen or $C_1$-$C_6$ alkyl;
$R^2$ and $R^3$ are each independently selected from halogen, hydroxy, $C_1$-$C_6$ alkyl, and $C_1$-$C_6$ alkoxy; and
$R^4$ is —C(O)$R^8$, —C(O)O$R^8$, —C(O)NH$R^8$, or —C(O)N($C_1$-$C_6$ alkyl)$R^8$,
where $R^8$ is $C_1$-$C_6$ alkyl, aryl, heteroaryl, heterocyclyl, aryl$C_1$-$C_6$ alkyl-, heteroaryl$C_1$-$C_6$ alkyl-, or heterocyclyl$C_1$-$C_6$ alkyl-, each optionally substituted with one or more of groups selected from halogen, cyano, nitro, $C_1$-$C_6$ alkyl, hydroxy. $C_1$-$C_6$ alkoxy, amino, $C_1$-$C_6$ alkylamino, and di$C_1$-$C_6$ alkylamino;
$R^5$ is selected from hydrogen and $C_1$-$C_6$ alkyl,
or $R^5$ and $R^8$ together with atoms to which they are attached form heterocyclyl optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, di$C_1$-$C_6$ alkylamino, oxo, or thio; and $R^6$ is —Z—$R^7$, wherein
Z is absent, —$C_1$-$C_6$ alkylene-, —O—$C_1$-$C_6$ alkylene-, —$C_1$-$C_6$ alkylene-O—, —NH—$C_1$-$C_6$ alkylene-, —$C_1$-$C_6$ alkylene-NH—, —O—, —NH—, or —N($C_1$-$C_6$ alkyl)-; and
$R^7$ is aryl, heteroaryl, or heterocyclyl, each optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino.

In other embodiments, compound of formula (I) is of formula (I-A):

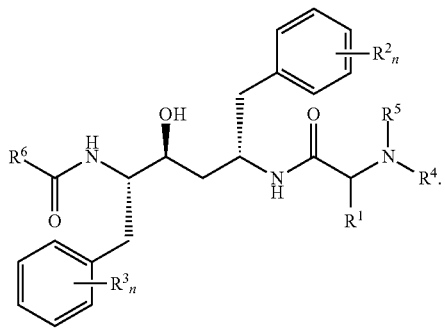

In other embodiments, the compound of formula (I) or formula (I-A) is wherein each n is 0. In some other embodiments, the compound of formula (I) or formula (I-A) is wherein $R^1$ is $C_1$-$C_6$ alkyl, or methyl, or ethyl, or, propyl, or isopropyl.

In other embodiments, the compound of formula (I) or formula (I-A) is wherein $R^4$ is —C(O)$R^8$, —C(O)O$R^8$, —C(O)NH$R^8$, or —C(O)N($C_1$-$C_6$ alkyl)$R^8$, where $R^8$ is $C_1$-$C_6$ alkyl, aryl, heteroaryl, heterocyclyl, aryl$C_1$-$C_6$ alkyl-, heteroaryl$C_1$-$C_6$ alkyl-, or heterocyclyl$C_1$-$C_6$ alkyl-, each optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino; and/or $R^5$ is selected from hydrogen and $C_1$-$C_6$ alkyl.

In some embodiments, the compound of formula (I) or formula (I-A) is wherein $R^4$ is —C(O)NH$R^8$ or —C(O)N($C_1$-$C_6$ alkyl)$R^8$, where $R^8$ is aryl$C_1$-$C_6$ alkyl-, heteroaryl$C_1$-$C_6$ alkyl-, or heterocyclyl$C_1$-$C_6$ alkyl-, each optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino. In some other embodiments, $R^5$ is hydrogen.

In some embodiments, the compound of formula (I) or formula (I-A) is wherein —N$R^4R^5$ is of formula:

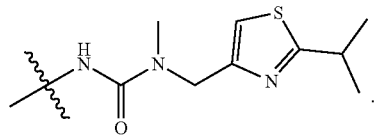 [SMILES: *NC(=O)N(C)Cc1csc(C(C)C)n1]

In other embodiments, the compound of formula (I) or formula (I-A) is wherein $R^5$ and $R^8$ together with atoms to which they are attached form heterocyclyl optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, di$C_1$-$C_6$ alkylamino, oxo, or thio.

In some embodiments, the compound of formula (I) or formula (I-A) is wherein —N$R^4R^5$ is of formula:

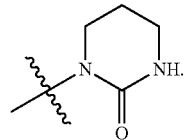

In some embodiments, the compound of formula (I) or formula (I-A) is wherein Z is —$C_1$-$C_6$ alkylene-, —O—$C_1$-$C_6$ alkylene-, or —$C_1$-$C_6$ alkylene-O—. In some other embodiments, $R^7$ is aryl, heteroaryl, or heterocyclyl, each optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino. In other embodiments, Z is —O-methylene- or -methylene-O—. In some other embodiments, $R^7$ is aryl or heteroaryl, each optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino.

In some embodiments, the compound of formula (I) or formula (I-A) is wherein $R^6$ is of formula:

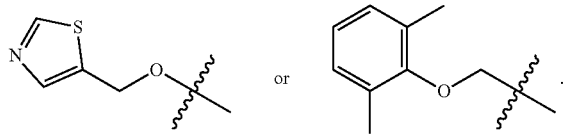 [SMILES: *OCc1cncs1 ; *COc1c(C)cccc1C]

In some embodiments, the inhibitor of the disclosure is a compound of formula (II):

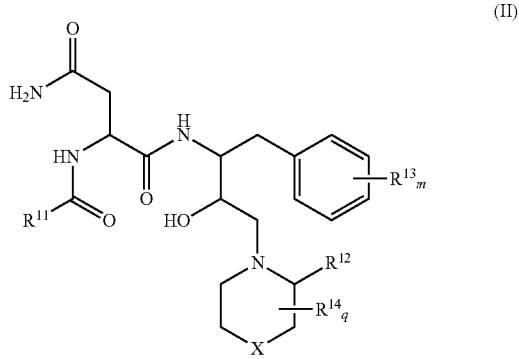

or pharmaceutically acceptable salts thereof, wherein
m is selected from 0, 1, 2, 3, and 4;
q is selected from 0, 1, 2, 3, and 4;
X is —O—, —NH—, —CH$R^{14}$—, —C($R^{14}$)$_2$—, or —CH$_2$—,
$R^{11}$ is aryl, heteroaryl, or heterocyclyl, each optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino;

$R^{12}$ is —C(O)$R^{15}$, —C(O)O$R^{15}$, —C(O)NH$R^{15}$, or —C(O)N($C_1$-$C_6$ alkyl)$R^{15}$, where $R^{15}$ is $C_1$-$C_6$ alkyl, $C_2$-$C_6$ alkenyl, $C_2$-$C_6$ alkynyl, aryl, heteroaryl, heterocyclyl, aryl$C_1$-$C_6$ alkyl-, heteroaryl$C_1$-$C_6$ alkyl-, or heterocyclyl$C_1$-$C_6$ alkyl-, each optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino;

$R^{13}$ is each independently selected from halogen, hydroxy, $C_1$-$C_6$ alkyl, and $C_1$-$C_6$ alkoxy; and $R^{14}$ is each independently selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino;

or two $R^{14}$ with atoms to which they are attached form heterocyclyl optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, di$C_1$-$C_6$ alkylamino, oxo, or thio.

In other embodiments, compound of formula (II) is of formula (II-A):

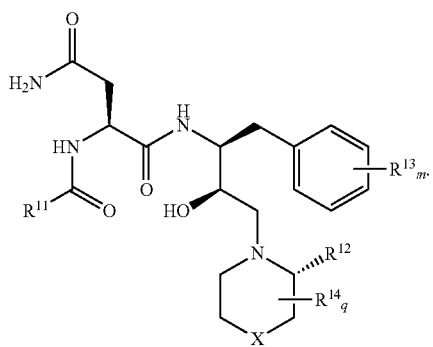

(II-A)

In other embodiments, the compound of formula (II) or formula (II-A) is wherein each m is 0.

In some embodiments, the compound of formula (II) or formula (II-A) is wherein $R^{11}$ is aryl or heteroaryl, each optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino. In some other embodiments, the compound of formula (II) or formula (II-A) is wherein $R^{11}$ is aryl or heteroaryl. In some other embodiments, the compound of formula (II) or formula (II-A) is wherein $R^{11}$ is heteroaryl.

In some embodiments, the compound of formula (II) or formula (II-A) is wherein $R^{11}$ is quinolinyl, or quinolin-2-yl.

In some embodiments, the compound of formula (II) or formula (II-A) is wherein $R^{12}$ is —C(O)NH$R^{15}$ or —C(O)N($C_1$-$C_6$ alkyl)$R^{15}$, where $R^{15}$ is $C_1$-$C_6$ alkyl, $C_2$-$C_6$ alkenyl, $C_2$-$C_6$ alkynyl, aryl, heteroaryl, heterocyclyl, aryl$C_1$-$C_6$ alkyl-, heteroaryl$C_1$-$C_6$ alkyl-, or heterocyclyl$C_1$-$C_6$ alkyl-, each optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, and di$C_1$-$C_6$ alkylamino.

In some embodiments, the compound of formula (II) or formula (II-A) is wherein $R^{12}$ is —C(O)NH$R^{15}$ or —C(O)N($C_1$-$C_6$ alkyl)$R^{15}$, where $R^{15}$ is $C_1$-$C_6$ alkyl, $C_2$-$C_6$ alkenyl, or $C_2$-$C_6$ alkynyl.

In some embodiments, the compound of formula (II) or formula (II-A) is wherein $R^{12}$ is —C(O)NH$R^{15}$ or —C(O)N($C_1$-$C_6$ alkyl)$R^{15}$, where $R^{15}$ is $C_1$-$C_6$ alkyl. In some other embodiments, $R^{12}$ is —C(O)NH$R^{15}$ and $R^{15}$ is $C_1$-$C_6$ alkyl. In some other embodiments, $R^{12}$ is —C(O)NH(tert-butyl).

In some embodiments, the compounds of formula (II) or formula (II-A) is wherein q is 1, —CH$R^{14}$—, and two $R^{14}$ with atoms to which they are attached form heterocyclyl optionally substituted with one or more of groups selected from halogen, cyano, nitro, $C_1$-$C_6$ alkyl, hydroxy, $C_1$-$C_6$ alkoxy, amino, $C_1$-$C_6$ alkylamino, di$C_1$-$C_6$ alkylamino, oxo, or thio. In other embodiments, two $R^{14}$ with atoms to which they are attached form decahydro-isoquinolin-2-yl. In other embodiments, two $R^{14}$ with atoms to which they are attached form 3-$R^{12}$-decahydro-isoquinolin-2-yl.

In some embodiments, an inhibitor according to the disclosure can be, for example, a small molecule inhibitor, an antibody, a nucleic acid such as an antisense nucleic acid, a short interfering RNA (siRNA) molecule, or a short hairpin RNA (shRNA) molecule. In addition, such inhibitors can be specifically designed using the methods described herein or using methods known in the art. For example, antibodies, particularly neutralizing antibodies and preferably monoclonal antibodies, can be generated by conventional means as described, for example, in "Antibodies: A Laboratory Manual" by Harlow and Lane (Cold Spring Harbor Press, 1988), which is hereby incorporated by reference.

In further embodiments, inhibitors or the disclosure are species of short interfering RNA (siRNA). The term "short interfering RNA" or "siRNA" as used herein refers to a double stranded nucleic acid molecule capable of RNA interference or "RNAi", as disclosed, for example, in Bass, 2001, Nature 411: 428-429; Elbashir et al., 2001, Nature 411: 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914. As used herein, siRNA molecules need not be limited to those molecules containing only RNA, but further encompasses chemically modified nucleotides and non-nucleotides having RNAi capacity or activity.

In still other embodiments, an API according to the present disclosure comprises an agonist. An agonist of the invention can increase the activity of a protein that is encoded by a gene either directly or indirectly. Direct activation can be accomplished, for example, by binding to a protein and thereby enhancing binding of the protein to an intended target, such as a receptor. Indirect activation can be accomplished, for example, by binding to a protein's intended target, such as a receptor or binding partner, and enhancing activity, e.g. by increasing the effective concentration of the target. Furthermore, an agonist of the invention can activate a gene by increasing expression of the gene, e.g., by increasing gene expression (transcription, processing, translation, post-translational modification), for example, by stabilizing the gene's mRNA or blocking degradation of the mRNA transcript, or by post-translational modification of a gene product, or by causing changes in intracellular localization.

Suitable agonist molecules specifically include agonist antibodies or antibody fragments, fragments or amino acid sequence variants of native polypeptides, peptides, small organic molecules, etc. Methods for identifying agonists of a native polypeptide may comprise contacting a native polypeptide with a candidate agonist molecule and measuring a detectable change in one or more biological activities normally associated with the native polypeptide.

Methods of Detecting Dystonia in a Subject

One aspect of the present disclosure provides a method of determining whether a subject is suffering from dystonia comprising determining the presence of a dystonia biomarker in a biological sample derived from the subject, wherein the presence of the biomarker is associated with dystonia.

In embodiments, the present disclosure provides methods of determining the presence of dystonia in a subject, and/or the likelihood of a subject developing dystonia, by measuring the level or activity of one or a plurality of biomarkers (e.g. 1, 2, 3, 4, 5, or more biomarkers) in a subject. In embodiments, the method comprises obtaining a sample from a subject to measure the one or a plurality of biomarkers in the sample. The subject may be any mammal, such as a human.

In embodiments, the methods of the disclosure may comprise obtaining more than one sample, such as two samples, three samples, four samples, or more, from one or more subjects. In certain embodiments, the methods of the disclosure comprise comparing the expression of one or a plurality of biomarkers (e.g. 1, 2, 3, 4, 5, or more biomarkers) from one or more subjects. In alternative embodiments, methods of the disclosure compare a one or a plurality of biomarkers in a single sample against a "standardized," or "reference," level of one or a plurality of biomarkers capable of detecting dystonia or dystonia related disorders. Before analyzing a sample according to the disclosure, in some embodiments one or more sample preparation operations, or steps, are performed upon the sample. Typically, these sample preparation operations, or steps, comprise one or more treatments, such as, without limitation, concentration, suspension, extraction of intracellular material, e.g., proteins/phosphopeptides from tissue/whole cell samples, and the like. Any method required for the processing of a sample prior to detection by any of the methods noted herein falls within the scope of the present disclosure. These methods are typically well known by a person skilled in the art.

In some aspects, the disclosure provides one or more biomarkers (e.g. 1, 2, 3, 4, 5, or more biomarkers) associated with dystonia comprising components of an intracellular signaling pathway mediated by eIF2-alpha. In embodiments, the one or more biomarkers associated with dystonia comprise the expression level of one or more components of an intracellular signaling pathway mediated by eIF2-alpha. In other embodiments, the one or more biomarkers associated with dystonia comprise an activity level of one or more components of an intracellular signaling pathway mediated by eIF2-alpha. In still other embodiments, the one or more biomarkers associated with dystonia comprise mutations in one or more components of an intracellular signaling pathway mediated by eIF2-alpha. In some embodiments, the biomarker(s) associated with dystonia comprise, one or more of the following proteins: Torsin1a, ATF4, BiP, eIF2-alpha, GADD34, CReP, HERPUD1, RAP1A, and MAP2K5, variants and mutations thereof, and combinations thereof. In certain embodiments, presence of a ΔE Torsin1a mis-localization associated with an increased likelihood of developing dystonia. In other embodiments, the presence of a ΔE Torsin1a mis-localization is associated with the presence of dystonia in a subject.

In some embodiments, the one or more biomarkers (e.g. 1, 2, 3, 4, 5, or more biomarkers) associated with Dystonia comprise mutations in components of intracellular signaling pathways mediated by the eIF2-alpha protein. In other embodiments, the one or more biomarkers associated with Dystonia comprise mutations in components of intracellular signaling pathways mediated by the ATF4 protein. In still further embodiments, the one or more biomarkers associated with Dystonia comprise mutations in components of intracellular signaling pathways mediated by the CReP protein. In yet additional embodiments, the one or more biomarkers associated with Dystonia comprise mutations in components of intracellular signaling pathways that are upstream or downstream of any of eIF2-alpha, ATF4, or CreP.

In some embodiments, the disclosure provides one or more biomarkers that indicate the state of an intracellular signaling pathway, such as an activated or inhibited intracellular signaling pathway. In certain embodiments, the disclosure provides one or more biomarkers that indicate the signaling state of the intracellular signaling pathway mediated by eIF2-alpha. In some embodiments, the disclosure provides one or more biomarkers comprising the phosphorylation state of, e.g., the Extracellular Signal-Regulated Kinases (ERKs), eIF2-alpha, eIF2-alpha kinases, or eIF2-alpha phosphatases. In other embodiments, the disclosure provides one or more biomarkers comprising the phosphorylation state of intracellular proteins downstream of eIF2-alpha signaling, such as the phosphorylation state of ATF4. In still further embodiments, the disclosure provides one or more biomarkers comprising the phosphorylation state of tyrosine 37 in ATF4.

In certain embodiments, the one or more biomarkers (e.g. 1, 2, 3, 4, 5, or more biomarkers) associated with Dystonia comprise mutations in the ATF4 protein found in sporadic dystonia patients. In a particular embodiment, the biomarker associated with Dystonia comprises a proline to leucine substitution at position 46 of the wild-type ATF4 protein sequence. In another particular embodiment, the biomarker associated with Dystonia comprises a tyrosine to phenylalanine substitution at position 37 of the wild-type ATF4 protein sequence. In still another particular embodiment, the biomarker associated with Dystonia comprises an arginine to lysine substitution at position 296 of the wild-type ATF4 protein sequence. In yet another particular embodiment, the biomarker associated with Dystonia comprises an aspartic acid to tyrosine substitution at position 35 of the wild-type ATF4 protein sequence. In still further embodiments, the biomarker associated with Dystonia comprises an aspartic acid to asparagine substitution at position 35 of the wild-type ATF4 protein sequence. In still further embodiments, the biomarker associated with Dystonia comprises an methionine to valine substitution at position 1 of the wild-type ATF4 protein sequence In still further embodiments, the biomarkers (e.g. 1, 2, 3, 4, 5, or more biomarkers) associated with Dystonia according the present disclosure comprise the expression of one or more genes responsive to the ATF protein. In some embodiments, the biomarkers of the present disclosure comprise reduced expression of one or more genes responsive to the ATF protein. In other embodiments, the biomarkers of the present disclosure comprise increased expression of one or more genes responsive to the ATF protein.

Another aspect of the present disclosure provides a method of predicting the likelihood of a subject developing dystonia comprising, consisting of, or consisting essentially of quantifying the amount of a dystonia biomarker present in a biological sample derived from the subject, wherein the present of the biomarker is associated with a likelihood of the subject developing dystonia.

Another aspect of the present disclosure provides a method of determining whether a subject is suffering from dystonia comprising, consisting of, or consisting essentially of: (a) obtaining a biological sample from a subject; (b) determining the expression level of a dystonia biomarker in the biological sample; (c) comparing the expression level of the biomarker in the biological sample with that of a control, wherein the presence of the biomarker in the sample that is in an amount greater than that of the control indicates the subject is suffering from dystonia; and (d) administering appropriate anti-dystonia therapy if the biomarker is expressed.

Another aspect of the present disclosure provides a method of determining whether a subject is at risk of developing dystonia comprising, consisting of, or consisting essentially of (a) obtaining a biological sample from a subject; (b) determining the expression level of a dystonia biomarker in the biological sample; (c) comparing the expression level of the biomarker in the biological sample with that of a control, wherein the presence of the bio marker in the sample that is in an amount greater than that of the control indicates the subject is at risk of developing dystonia; and (d) administering appropriate anti-dystonia therapy if the biomarker is expressed.

In other aspects, the disclosure provides methods for monitoring progression of dystonia in a patient, for example, to determine if a patient is responding positively or negatively to a certain treatment regime.

In another embodiment, the determination of the presence of dystonia in a subject and/or the likelihood of a person developing dystonia can be determined by comparing the subject's biomarker profile to a reference biomarker profile, such as one that corresponds to biological samples obtained from a normal population that do not have a condition such as dystonia, or that corresponds to biological samples obtained from a population that have a condition such as dystonia. As used herein, a "reference biomarker profile" means a control level or range obtained from multiple subjects, or from one or more subjects over time. Optionally, a reference profile according to the disclosure comprises multiple biomarker expression profiles, with each corresponding to a different stage of a condition such as dystonia. Optionally, a reference profile according to the disclosure comprises a reference biomarker profile from one or more subjects.

In some embodiments, the level or concentration of one or more biomarkers (e.g. 1, 2, 3, 4, 5, or more biomarkers) in a subject is increased relative to a reference biomarker profile. In other embodiments, the level or concentration of one or more biomarkers is decreased relative to a reference biomarker profile. In still other embodiments, the level or concentration of one or more biomarkers is decreased, whereas the level or concentration of other biomarkers are increased, relative to a control level or range.

In embodiments, the level or concentration of one or more biomarkers (e.g. 1, 2, 3, 4, 5, or more biomarkers) changes by at least about 10 percent, for example, by at least about 25, 30, 35, 40, 45, 50, 55, 60, 65, 70, 75, 80, 85, 90, 95 or 100 percent, relative to a control level or range. In some embodiments, the level or concentration of one or more biomarkers changes by at least about 2-fold, for example, at least about 4, 6, 8, 10, 20, 40, 60, 80, or 100 fold, relative to a reference biomarker profile. A "control level" or "reference level" as used herein refers to an amount or range of amounts of a biochemical marker, such as, without limitation, Torsin1a, ATF4, BiP, eIF2-alpha, GADD34, CreP, HERPUD1, RAP1A, and MAP2K5, variants and mutations thereof, found in a comparable biosample in subjects not suffering from dystonia, or from a subject known to be suffering from dystonia, or from a subject with a known inherited or genetic form of dystonia. The "control level" or "reference level" can also be based on a database of biochemical markers such as from previously tested subjects who did not exhibit, or develop, dystonia or dystonia related disorders over a clinically relevant time.

In some embodiments, the present disclosure provides one or a plurality of biomarkers (e.g. 1, 2, 3, 4, 5, or more biomarkers) capable of determining the presence of dystonia in a subject. In further embodiments, the disclosure provides one or a plurality of biomarkers capable of determining the likelihood of a subject developing dystonia.

In certain embodiments, the disclosure provides biomarkers (e.g. 1, 2, 3, 4, 5, or more biomarkers), such as Torsin1a, ATF4, BiP, eIF2-alpha, GADD34, CreP, HERPUD1, RAP1A, and MAP2K5, variants and mutations thereof as biomarkers useful for determining the presence of dystonia in a subject, and/or the likelihood of a subject developing dystonia. The inventors have determined that certain biomarkers are directly involved in dystonia and/or likelihood of developing dystonia, and their expression pattern in a biological sample can be associated with the pathophysiological status of the subject suffering from dystonia.

The disclosure also provides methods for identifying a subject that is eligible for reimbursement of an insurance claim for treatment of dystonia, or dystonia related disorders. In these embodiments, the methods comprise the steps of: (a) isolating a biosample from a subject; (b) determining a level or concentration of one or more biomarkers present in the biosample; and (c) as eligible for reimbursement of the insurance claim when the concentration of one or more biomarkers is increased or decreased relative to an insurance control value. In these embodiments, the insurance control value refers to an amount or range of amounts of a biochemical marker.

The insurance control value refers to an amount or range of amounts of one or more biochemical markers found in a comparable biosample in subjects not suffering from dystonia, or dystonia related disorders, and used as an insurance reimbursement criterion by, inter alia, a health insurer. In another embodiment, insurance coverage of an individual is assessed as a function of actuarial data that is obtained from individuals with changes in concentration of the one or more biomarkers disclosed herein. A control level according to embodiments of the present methods is based on a database of biochemical marker such comprising one or more biomarkers from previously tested subjects who did not exhibit or develop dystonia, or dystonia related disorders, over a clinically relevant time frame. Additionally, a control level according to embodiments of the present methods is based on an individual that did not file a reimbursement claim based on dystonia, or dystonia related disorders, within an actuarially relevant time period.

In some aspects, a subject is included or enrolled in an insurance plan based on the insurable status of the subject or wherein the rate or cost of the insurance is based on the insurable status of the subject. Alternatively, the subject is excluded from an insurance plan based on the insurable status of the subject. In some such instances, an organization that provides medical insurance requests or otherwise obtains information concerning a subject's biochemical marker status and uses that information to determine an appropriate medical insurance premium or reimbursement of an insurance claim relating to treatment of the subject.

The disclosure also provides methods for determining the efficacy of a treatment for dystonia, or dystonia related disorders, in a subject. In these embodiments, the methods comprise the steps of: (a) treating a subject for dystonia, or a dystonia related disorder; (b) isolating a biosample from the subject; (c) determining a level or concentration of one or more biomarkers present in the biosample; and (d) determining the efficacy of the treatment for dystonia, or dystonia related disorders, when the concentration of one or more biomarkers is increased or decreased relative to a pre-treatment level or pre-treatment range of the one or more biomarkers. In embodiments, the one or more biomarkers comprise the genes, or gene products, selected from Torsin1a, ATF4, BiP, eIF2-alpha, GADD34, CreP, HERPUD1, RAP1A, and MAP2K5. In some embodiments, the control sample is a biological sample from a normal subject, i.e. an individual without dystonia, or dystonia related symptoms, or one who responds to therapy for a condition characterized by dystonia, or dystonia related disorders.

In some embodiments, a panel of biomarkers capable of predicting the occurrence of dystonia, or dystonia related disorders, or determining the efficacy of a treatment for dystonia, or dystonia related disorders is provided. Embodiments of a biomarker panel are comprised of two or more biomarkers. In one embodiment, a biomarker panel comprises the genes, or gene products of, two or more of Torsin1a, ATF4, BiP, eIF2-alpha, GADD34, CreP, HERPUD1, RAP1A, and MAP2K5. In some embodiments, a panel of two or more biomarkers disclosed herein provide an improved method according to the disclosure. In embodiments, improvements using a panel of two or more biomarkers comprise greater accuracy or specificity relative to a single biomarker, or to an alternative biomarker panel.

As described above, certain embodiments of the disclosure comprise detecting one or more biomarkers (e.g. 1, 2, 3, 4, 5, or more biomarkers) in a sample. In some embodiments, detection may comprise detecting the presence versus absence of one or more biomarkers. In some embodiments, detection may comprise quantifying the level or degree of expression of one or more biomarkers, depending on the method of detection employed. Determining the amount of a biomarker, such as Torsin1a, ATF4, BiP, eIF2-alpha, GADD34, CreP, HERPUD1, RAP1A, and MAP2K5 in a sample relates to measuring an amount or concentration of biomarker protein or nucleic acid in the sample. In certain embodiments, such measurements are semi-quantitative or quantitative. Measuring can be done directly or indirectly. Direct measuring relates to measuring the amount or concentration of the protein or nucleic acid based on a signal which is obtained from the protein or nucleic acid itself and the intensity of which directly correlates with the number of molecules of the protein or nucleic acid present in the sample. Such a signal—sometimes referred to as intensity signal—may be obtained, for example, by measuring an intensity value of a specific physical or chemical property of the protein or nucleic acid. Indirect measuring includes measuring of a signal obtained from a secondary component (i.e., a component not being the protein or nucleic acid itself) or a biological read out system, e.g., measurable cellular responses, ligands, labels, or enzymatic reaction products.

In aspects of the present disclosure, determining the amount of a peptide or polypeptide (protein) can be achieved by all known means for determining the amount of a peptide or polypeptide in a sample. For example, without limitation, the methods of the present disclosure comprise immunoassay devices and methods that may utilize labelled molecules in various sandwich, competition, or other assay formats. Said assays will develop a signal which is indicative for the presence or absence of the peptide or polypeptide. Moreover, the signal strength can be correlated directly or indirectly (e.g., reverse-proportional) to the amount of polypeptide present in a sample. Other suitable methods comprise measuring a physical or chemical property specific for the peptide or polypeptide such as its precise molecular mass or NMR spectrum. Said methods may comprise biosensors, optical devices coupled to immunoassays, biochips, and analytical devices such as mass-spectrometers, NMR-analyzers, or chromatography devices. Other suitable methods include micro-plate ELISA-based methods, fully-automated or robotic immunoassays.

In other embodiments, the amount of a peptide or polypeptide is determined by contacting the peptide with a specific ligand, optionally removing non-bound ligand, and measuring the amount of bound ligand. The bound ligand will generate an intensity signal. Binding according to the present disclosure includes both covalent and non-covalent binding. A ligand according to the present disclosure can be any compound, e.g., a peptide, polypeptide, nucleic acid, or small molecule, binding to the peptide or polypeptide described herein. Suitable ligands include antibodies, nucleic acids, peptides or polypeptides such as receptors or binding partners for the peptide or polypeptide and fragments thereof comprising the binding domains for the peptides, and aptamers, e.g., nucleic acid or peptide aptamers. Methods to prepare such ligands are well known in the art. For example, identification and production of suitable antibodies or aptamers is offered by commercial suppliers. Those skilled in the art are familiar with methods to develop derivatives of such ligands with higher affinity or specificity. For example, random mutations can be introduced into the nucleic acids, peptides, or polypeptides. These derivatives can then be tested for binding according to screening procedures known in the art, e.g., phage display. Antibodies as referred to herein include both polyclonal and monoclonal antibodies, as well as fragments thereof, such as Fv, Fab and F(ab)$_2$ fragments that are capable of binding antigen or hapten. The present disclosure also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. In some embodiments, the ligand or agent specifically binds to the peptide or polypeptide. Specific binding according to the present disclosure means that the ligand or agent should not bind substantially to ("cross-react" with) another peptide, polypeptide, or substance present in the sample to be analyzed. In certain embodiments, the specifically bound peptide or polypeptide should be bound with at least 3 times higher, at least 10 times higher, or at least 50 times higher affinity than any other relevant peptide or polypeptide. Non-specific binding may be tolerable if it can still be distinguished and measured unequivocally, e.g., according to its size on a Western Blot, or by its relatively higher abundance in the sample. Binding of the ligand can be measured by any method known in the art. In certain embodiments, the method is semi-quantitative or quantitative.

The amount of a peptide or polypeptide may also be determined by contacting a solid support comprising a ligand for the peptide or polypeptide as specified above with a sample comprising the peptide or polypeptide and measuring the amount peptide or polypeptide which is bound to the support. The ligand may be chosen from the group consisting of nucleic acids, peptides, polypeptides, antibodies and aptamers, and can be present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, and plastic tubes. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the disclosure. Suitable methods for fixing/immobilizing said ligand are well known and include, but are not limited to ionic, hydrophobic, covalent interactions and the like. It is also contemplated to use "suspension arrays" as arrays according to the present disclosure (Nolan et al., 2002, *Trends Biotechnol.* 20(1): 9-12). In such suspension arrays, the carrier, e.g., a microbead or microsphere, is present in suspension. The array consists of different microbeads or microspheres, possibly labelled, carrying different ligands. Methods of producing such arrays, for example based on solid-phase chemistry and photo-labile protective groups, are generally known (U.S. Pat. No. 5,744,305).

In some embodiments, a peptide or polypeptide of the disclosure is measured directly, e.g., by NMR or surface plasmon resonance. In other embodiments, an enzymatic reaction product may be measured (e.g., the amount of a protease can be measured by measuring the amount of cleaved substrate, e.g., on a Western Blot). Alternatively, the peptide or polypeptide may exhibit enzymatic properties itself, and may be contacted with a suitable substrate allowing detection by the generation of an intensity signal. For measurement of enzymatic reaction products, the amount of substrate can be saturating. The substrate may also be labelled with a detectable label prior to the reaction. In one embodiment, a sample is contacted with the substrate for an adequate period of time. An adequate period of time refers to the time necessary for a detectable and measurable amount of product to be produced. Instead of measuring the amount of product, the time necessary for appearance of a given (e.g., detectable) amount of product can be measured.

In still other embodiments, a peptide or polypeptide of the disclosure is measured indirectly, and may be coupled covalently or non-covalently to a label allowing detection and measurement. Labelling may be done by direct or indirect methods. Direct labelling involves coupling of the label directly (covalently or non-covalently) to the peptide or polypeptide. Indirect labelling involves binding (covalently or non-covalently) of a secondary ligand to the peptide or polypeptide. The secondary ligand should specifically bind to the peptide or polypeptide. Said secondary ligand may be coupled with a suitable label and/or be the target (receptor) of tertiary ligand binding to the secondary ligand. Secondary, tertiary, or even higher order ligands are often used to increase the signal. Suitable secondary and higher order ligands may include antibodies, secondary antibodies, and the well-known streptavidin-biotin system (Vector Laboratories, Inc.). The peptide or polypeptide or substrate may also be "tagged" with one or more tags as known in the art. Such tags may then be targets for higher order ligands. Suitable tags include biotin, digoxygenin, His-Tag, Glutathione-S-transferase, FLAG, GFP, myc-tag, influenza A virus hemagglutinin (HA), maltose binding protein, and the like. In the case of a peptide or polypeptide, the tag may be located at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels (e.g., magnetic beads, including paramagnetic and superparamagnetic labels), and fluorescent labels. Enzymatically active labels include e.g., horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-STAR™ (Amersham Biosciences), ECF™ (Amersham Biosciences). A suitable enzyme-substrate combination may result in a colored reaction product, fluorescence, or chemoluminescence, which can be measured according to methods known in the art (e.g., using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g., Alexa 568). Other fluorescent labels are available e.g., from Molecular Probes (Oregon). Also the use of quantum dots as fluorescent labels is contemplated. Typical radioactive labels include $^{35}$S, $^{125}$I, $^{32}$P, $^{33}$P, and the like. A radioactive label can be detected by any method known and appropriate, e.g., a light-sensitive film or a phosphor imager. Suitable measurement methods according the present disclosure also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro 31hosph assay (DELFIA), scintillation proximity assay (SPA), turbidimetry, nephelometry, latex-enhanced turbidimetry or nephelometry, or solid phase immune tests. Other methods known in the art (such as gel electrophoresis, 2D gel electrophoresis, SDS polyacrylamide gel electrophoresis (SDS-PAGE), Western Blotting, and mass spectrometry) can be used alone or in combination with labelling or other detection methods as described above.

In some embodiments, the detection methods of the disclosure comprise in situ methods. In alternative embodiments, the detection methods of the disclosure comprise screening methods.

As used herein, an in situ method refers to the detection of protein, phosphopeptide, and/or nucleic acid molecules in a sample wherein the structure of the sample has been preserved. This may thus be a biopsy (e.g., a tissue biopsy) wherein the structure of the tissue is preserved. In situ methods are generally histological i.e. microscopic in nature and include but are not limited to methods such as: in situ hybridization techniques and in situ PCR methods.

In some embodiments, methods of the disclosure comprise in situ hybridization methods. In situ hybridization (ISH) applies and extrapolates the technology of nucleic acid and/or polypeptide hybridization to the single cell level, and, in combination with the art of cytochemistry, immunocytochemistry and immunohistochemistry, permits the maintenance of morphology and the identification of cellular markers to be maintained and identified, allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). DNA ISH can be used to determine the structure of chromosomes and the localization of individual genes and optionally their copy numbers. Fluorescent DNA ISH (FISH) can for example be used in medical diagnostics to assess chromosomal integrity. RNA ISH is used to assay expression and gene expression patterns in a tissue/across cells, such as the expression of miRNAs/nucleic acid molecules. Sample cells are treated to increase their permeability to allow the probe to enter the cells, the probe is added to the treated cells, allowed to hybridize at pertinent temperature, and then excess probe is washed away. A complementary probe is labeled with a radioactive, fluorescent or antigenic tag, so that the probe's location and quantity in the tissue can be determined using autoradiography, fluorescence microscopy or immunoassay, respectively. The sample may be any sample as herein described. The probe is likewise a probe according to any probe based upon the biomarkers mentioned herein.

In some embodiments, methods of the disclosure comprise in situ PCR. In situ PCR comprises PCR based amplification of target nucleic acid sequences prior to ISH. For detection of RNA, an intracellular reverse transcription (RT) step is introduced to generate complementary DNA from RNA templates prior to in situ PCR. This enables detection of low copy RNA sequences. Prior to in situ PCR, cells or tissue samples are fixed and permeabilized to preserve morphology and permit access of the PCR reagents to the intracellular sequences to be amplified. PCR amplification of target sequences is performed either in intact cells held in suspension or directly in cytocentrifuge preparations or tissue sections on glass slides. In the former approach, fixed cells suspended in the PCR reaction mixture are thermally cycled using conventional thermal cyclers. After PCR the cells are cytocentrifugated onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens. Detection of intracellular PCR-products is achieved by one of two entirely different techniques. In indirect in situ PCR by ISH with PCR-product specific probes, or in direct in situ PCR without ISH through direct detection of labeled nucleotides (e.g. digoxigenin-11-dUTP, fluorescein-dUTP, $^3$H-CTP or biotin-16-dUTP) which have been incorporated into the PCR products during thermal cycling.

In some embodiments, the disclosure provides one or more biomarkers comprising a radiolabel facilitating medical diagnostic procedures, including Positron Emission Tomography (PET) and Single Photon Emission Computed Tomography (SPECT). PET and SPECT are very sensitive techniques and require small quantities of radiolabeled compounds, called tracers. The labeled compounds, such as a biomarker according to the disclosure, are transported, accumulated, and converted in vivo in exactly the same way as the corresponding non-radioactively labeled compounds. Tracers, or probes, can be radiolabeled with a radionuclide useful for PET imaging, such as $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I and $^{131}$I, or with a radionuclide useful for SPECT imaging, such as $^{99}$Tc, $^{75}$Br, $^{61}$Cu, $^{153}$Gd, $^{125}$I, $^{131}$I and $^{32}$P. One example of a PET probe is [$^{18}$F]-fluorodeoxyglucose ([$^{18}$F]-FDG).

Screening methods, as used herein, employ techniques of molecular biology. In embodiments, the screening methods of the disclosure comprise preparing sample material in order to access the nucleic acid and/or polypeptide molecules to be detected. Screening methods include, but are not limited to methods such as: Array systems, affinity matrices, Northern blotting and PCR techniques, such as real-time quantitative RT-PCR.

In some embodiments, the methods of the disclosure comprise screening one or more samples using, for example, a microarray. A microarray is a microscopic, ordered array of nucleic acids, proteins, small molecules, cells or other substances that enables parallel analysis of complex biochemical samples. A DNA microarray consists of different nucleic acid probes, known as capture probes that are chemically attached to a solid substrate, which can be a microchip, a glass slide or a microsphere-sized bead. Microarrays can be used e.g. to measure the expression levels of large numbers of polypeptides/proteins/nucleic acids simultaneously.

Several types of microarrays can be employed in embodiments of the disclosure, such as, without limitation, spotted oligonucleotide microarrays, pre-fabricated oligonucleotide microarrays or spotted long oligonucleotide arrays.

In spotted oligonucleotide microarrays the capture probes are oligonucleotides complementary to nucleic acid sequences. This type of array is typically hybridized with amplified. PCR products of size-selected small RNAs from two samples to be compared that are labelled with two different fluorophores. Alternatively, total RNA containing the small RNA fraction is extracted from the abovementioned two samples and used directly without size-selection of small RNAs, and 3' end labeled using T4 RNA ligase and short RNA linkers labelled with two different fluorophores. The samples can be mixed and hybridized to one single microarray that is then scanned, allowing the visualization of up-regulated and down-regulated biomarker genes in one go. The downside of this is that the absolute levels of gene expression cannot be observed, but the cost of the experiment is reduced by half. Alternatively, a universal reference can be used, comprising of a large set of fluorophore-labelled oligonucleotides, complementary to the array capture probes.

Spotted long oligonucleotide arrays are composed of 50 to 70-mer oligonucleotide capture probes, and are produced by either ink-jet or robotic printing. Short Oligonucleotide Arrays are composed of 20-25-mer oligonucleotide probes, and are produced by photolithographic synthesis (Affymetrix) or by robotic printing. More recently, Maskless Array Synthesis from NimbleGen Systems has combined flexibility with large numbers of probes. Arrays can contain up to 390,000 spots, from a custom array design.

In pre-fabricated oligonucleotide microarrays or single-channel microarrays, the probes are designed to match the sequences of known or predicted biomarkers. There are commercially available designs that cover complete genomes from companies such as Affymetrix, or Agilent. These microarrays give estimations of the absolute value of gene expression and therefore the comparison of two conditions requires the use of two separate microarrays.

In some embodiments, the disclosure provides methods of screening for one or more biomarkers in a sample using PCR. The terms "PCR reaction", "PCR amplification", "PCR", "pre-PCR", "Q-PCR", "real-time quantitative PCR" and "real-time quantitative RT-PCR" are used to signify use of a nucleic acid amplification system, which multiplies the target nucleic acids being detected. Examples of such systems include the polymerase chain reaction (PCR) system and the ligase chain reaction (LCR) system. Other methods recently described and known to the person of skill in the art are the nucleic acid sequence based amplification and Q Beta Replicase systems. The products formed by said amplification reaction may or may not be monitored in real time or only after the reaction as an end-point measurement.

In certain embodiments, the methods of the disclosure comprise screening for one or more biomarkers (e.g. 1, 2, 3, 4, 5, or more biomarkers) in a sample using real-time quantitative RT-PCR (qRT-PCR), qRT-PCR is a modification of polymerase chain reaction used to rapidly measure the quantity of a product of polymerase chain reaction. It is preferably done in real-time, thus it is an indirect method for quantitatively measuring starting amounts of DNA, complementary DNA or ribonucleic acid (RNA). This is commonly used for the purpose of determining whether a genetic sequence is present or not, and if it is present the number of copies in the sample.

In some embodiments, the disclosure employs one of 3 methods of RT-PCR, or qRT-PCR. Like other forms of polymerase chain reaction, these methods are used to amplify DNA samples, using thermal cycling and a thermostable DNA polymerase. For example, the methods of the disclosure employ RT-PCR using agarose gel electrophoresis, the use of SYBR Green, a double stranded DNA dye, or the used of one or more fluorescent reporter probes. The latter two of these are optionally analyzed in real-time, constituting real-time polymerase chain reaction method.

In embodiments, the methods of the disclosure comprise detecting one or more biomarkers (e.g. 1, 2, 3, 4, 5, or more biomarkers) in a sample using RT-PCR, wherein the products of said RT-PCR are analyzed using agarose gel electrophoresis. In exemplary embodiments, the unknown sample and a known sample are prepared with a known concentration of a similarly sized section of target DNA for amplification. Both reactions are run for the same length of time in identical conditions (preferably using the same primers, or at least primers of similar annealing temperatures). Agarose gel electrophoresis is used to separate the products of the reaction from their original DNA and excess primers. The relative quantities of the known and unknown samples are measured to determine the presence or quantity of one or more biomarkers in the unknown sample. Accordingly, embodiments of the method are useful to determine whether the probe target sequences of the one or more biomarkers are present or not.

In other embodiments, the methods of the disclosure comprise detecting one or more biomarkers (e.g. 1, 2, 3, 4, 5, or more biomarkers) in a sample using RT-PCR, wherein the products of said RT-PCR are analyzed using SYBR green dye. In these embodiments, a DNA binding dye (SYBR green) binds all newly synthesized double stranded (ds)DNA, and an increase in fluorescence intensity is measured, thus allowing initial concentrations to be determined. A PCR reaction is prepared as usual, using primers directed to the one or more biomarkers disclosed herein, with the addition of fluorescent dsDNA dye. The PCR reaction is run, and the levels of fluorescence are monitored. Comparing the level of fluorescence in the sample to a reference standard sample or a standard curve allows determination of the dsDNA concentration in the reaction, and thus a measure of the presence and quantity of starting material, comprising one or more biomarkers of the disclosure, in the sample.

In still other embodiments, the methods of the disclosure comprise detecting one or more biomarkers (e.g. 1, 2, 3, 4, 5, or more biomarkers) in a sample using RT-PCR, wherein the products of said RT-PCR are analyzed using a fluorescent reporter probe. For example, a sequence-specific nucleic acid based probe that recognizes the one or more biomarkers of the disclosure is used to quantify the presence or levels of said biomarkers in a sample. It is commonly carried out with DNA based probes with a fluorescent reporter and a quencher held in adjacent positions, so-called dual-labelled probes. The close proximity of the reporter to the quencher prevents its fluorescence; it is only on the breakdown of the probe that the fluorescence is detected. This process depends on the 5' to 3' exonuclease activity of the polymerase involved. The real-time quantitative PCR reaction is prepared with the addition of the dual-labelled probe, thereby allowing accurate determination of the final, and so initial, quantities of one or more biomarkers present in the sample.

In embodiments, the methods of the disclosure comprise one or more probes useful for detecting biomarkers (e.g. 1, 2, 3, 4, 5, or more biomarkers) according to the methods disclosed herein. In some embodiments, the probes of the disclosure are useful for the detection of a protein, phosphopeptide, nucleic acid and/or polypeptide molecule. In some embodiments, a probe of the disclosure is capable of recognizing, or detecting, one or more specific sequences of nucleic acid and/or polypeptide. In some embodiments, a probe of the disclosure is capable of recognizing a biomarker of the disclosure by hybridization. A nucleic acid according to the methods of the disclosure comprises any nucleic acid, natural or synthetic, such as DNA, RNA, siRNA, LNA or PNA.

In some embodiments, a probe may be labeled, tagged, immobilized, or otherwise modified according to the requirements of the detection method chosen. A label or a tag is an entity making it possible to identify a compound with which it is associated. It is within the scope of the present disclosure to employ probes that are labeled or tagged by any means known in the art such as but not limited to: radioactive labeling, fluorescent labeling and enzymatic labeling. Furthermore, the probe, labeled or not, may be immobilized to facilitate detection according to the detection method of choice, and this may be accomplished according to the the particular detection method.

Another aspect of the present disclosure provides a kit, comprising: (a) a probe array for determining the presence or level of a dystonia biomarker in a sample, the array comprising of a plurality of probes that hybridizes to the biomarker or variants and mutations thereof that are associated with dystonia and/or likelihood of developing dystonia; or (b) a kit for determining the presence of the biomarker in a sample, comprising the probe array of (a) and instructions for carrying out the determination of the presence of the biomarker in the sample. In some embodiments, the probe array of (a) further comprises a solid support with the plurality of probes attached thereto.

The invention will be further described in the following examples, which do not limit the scope of the invention described in the claims.

The Examples that follow are illustrative of specific embodiments of the invention and various uses thereof. They are set forth for explanatory purposes only and are not to be taken as limiting the invention.

EXAMPLES

Example 1 Development and Validation of Delta-E Torsin1a Localization Assay

To develop an assay capable of detecting conditions that correct a dystonia cellular phenotype, two human cell lines were generated that stably expressed EGFP-tagged human wild-type Torsin 1A, or delta-E Torsin1a, from a single cDNA copy integrated at a defined genomic site (FIG. 1, panel 1).

To limit variation in expression levels associated with random integration or transient expression, single copies of either WT or delta-E human TOR1A cDNAs with N-terminal EGFP fusions were inserted at the FRT site in Flp-In™ T-Rex™ 293 cells (Thermo Fisher Scientific #R780-07) via flippase recombinase-mediated cassette exchange according to the manufacturer's recommended protocols. This system includes an inducible expression feature (TetON) that avoids selective pressure for potential toxic effects of chronic expression of mutant proteins (FIG. 1, panel 1).

Flp-In T-Rex 293 cells inducibly expressing either WT or delta-E Torsin1a were maintained in selective media [DMEM-HG (Thermo Fisher Scientific #11965)+1× Gluta-Max (Thermo Fisher Scientific #35050-061)+75 µg/mL hygromycin (Thermo Fisher Scientific #10687-010)+15 µg/mL blasticidin S (Thermo Fisher Scientific #R210-01)+ 10% tetracycline screened FBS (Hyclone #SH30070.03T)+ 1% penicillin/streptomycin/amphotericin (Mediatech Inc. #30-004-Cl)]. The cells were maintained at 37° C./5% CO2. All experiments were performed on cells with fewer than 5 passages. HEK 293T cells (ATCC #CRL-3216) were maintained in HEK-T media [DMEM (Thermo Fisher #11995)+ 10% FBS (Hyclone#SH30070.03)+1× GlutaMAX+1% penicillin/streptomycin/amphotericin] at 37° C./5% CO2. Human dermal fibroblast lines were maintained in FGM media [MEM (Thermo Fisher #11095-080)+15% FBS (Hyclone #SH30070.03)+1% Non-Essential Amino Acids (Lonza #13-114E)+1% penicillin/streptomycin/amphotericin] at 37° C./5% CO2.

This approach provides control over expression levels, avoiding the wide variation typically seen with random genomic integration or transient expression approaches. Torsin1a expression was also controlled by tetracycline induction to avoid selective pressure modifying the cellular phenotypes. In this expression system, the WT and delta-E Torsin1a lines consistently and robustly reproduced their respective subcellular localization phenotypes (FIG. 1, panels a, b). The mutant phenotype was measured as the percentage of cells with one or more EGFP puncta using automated high-content imaging analysis (see infra).

Upon establishing automated conditions to identify cells with the characteristic punctate EGFP signal, the predictive validity of the automated readout in corroborating existing observations regarding Torsin1a biology was tested. First, compensation by the homologous protein, Torsin1b, is hypothesized to underlie the selective vulnerability of the brain where Torsin1b levels are low. (Jungwirth, M., et al., (2010) *Hum. Mol. Genet.* 19, 888-900.) Consistent with this model, knockdown of Torsin1b significantly increased Torsin1a mis-localization in both the WT and delta-E cell lines (FIG. 1, panel c). % Selected Cells refers to percent of cells that have one or more puncta of EGFP signal as determined by automated image analysis. N=16 independent wells treated with non-silencing siRNA control and 32 independent wells treated with TOR1B siRNAs. *, $p<0.05$; ***, $p<0.0005$ by unpaired t test.

Second, steady-state protein levels of Torsin1a have also been hypothesized to contribute to DYT1 dystonia pathogenesis. (Jungwirth, M., et al., (2010) *Hum. Mol. Genet.* 19, 888-900; Kim, C. E., et al., (2010) *Proc. Natl. Acad. Sci. U.S.A.* 107, 9861-6; Hewett, J. W. et al., (2007) *Proc. Natl. Acad. Sci. U.S.A.* 104, 7271-6.) That model supported by observations in transgenic mouse models. (Goodchild, R. E. & Dauer, W. T. (2004) *Proc. Natl. Acad. Sci. U.S.A* 101, 847-52.) Indeed, we found that inhibiting protein clearance with the proteasome inhibitor MG132 (MG132, 10 µM) significantly increased the percentage of cells with punctate EGFP-Torsin1a signal in both WT and delta-E cell lines (FIG. 1, panel d).

Lastly, expression of delta-E Torsin1a has been associated with increased ER stress and activation of the unfolded protein response (UPR). (Chen, P. et al. (2010) *Hum. Mol. Genet.* 19, 3502-15; Bragg, D. C., et al., (2011) *Neurobiol. Div.* 42, 136-47; Nery, F. C. et al. (2011) *Nat. Commun.* 2, 393; Cao, S. et al. (2010) *Dis. Model. Mech.* 3, 386-96.) In addition, the chemical chaperone phenylbutyric acid (PBA) has recently been shown to reduce signs of ER stress in DYT1 patient-derived fibroblasts. (Barrows, N. J., et al., (2010) *J. Biomol. Screen* 15, 735-47.) We also found that PBA (20 mM) ameliorated the burden of cells with punctate pathology in our assay cell lines (FIG. 1, panel d).

Importantly DMSO vehicle had no effect on the number of cells one or more puncta of EGFP signal. (n=4 independent DMSO-treated wells and 8 independent wells each for MG132 and PBA treatments. ***, $p<0.0005$ by unpaired t test.)

Thus, these observations support the utility of the phenotypic screen as a tool to identify factors that modulate delta-Torsin1a mis-localization, and by extension dystonia phenotypes.

Figure 9:
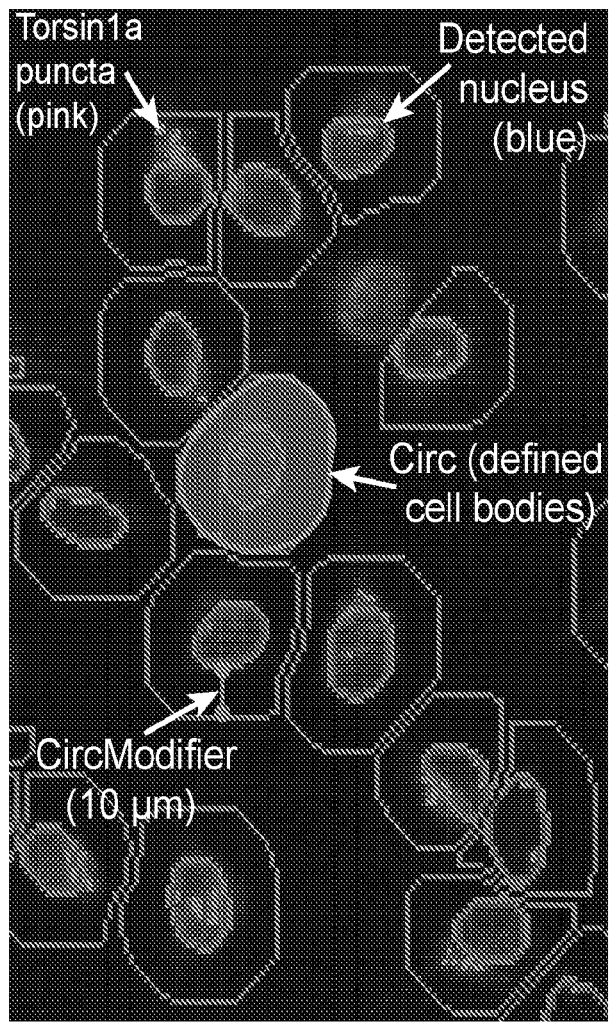
FIG. 9 shows high-content image analysis and assay performance under high-throughput screening conditions. Panels (a) and (b) show automated image analysis and determination of EGFP-Torsin1a localization using Cellomics compartmentalization protocol software. Assay output (defined as % selected cells) is the percentage of cells that are identified with puncta. Panel (c) shows the time course of the high-throughput, high-content RNAi screening assay. Panel (d) shows that the percentage of selected cells was robustly higher in the ΔE compared to WT Torsin1a assay cells (Z'=0.614±0.077), and treatment with a Positive Control (PC) siRNA reliably led to a marked reduction in the percent of selected cells. n=96 independent wells per condition. ***, p<0.0005 by unpaired t test. Data in (d) are presented as box-and-whisker plot displaying 90% confidence interval. Panel (e) shows that TOR1A siRNA mediated silencing of assay readout protein (EGFP-Torsin1a) reduces the percent of selected cells to near zero. n=16 independent wells treated with non-silencing siRNA control and 32 independent wells treated with TOR1A siRNA. Data in (e) are presented as means±S.E.M.
Figure 9:
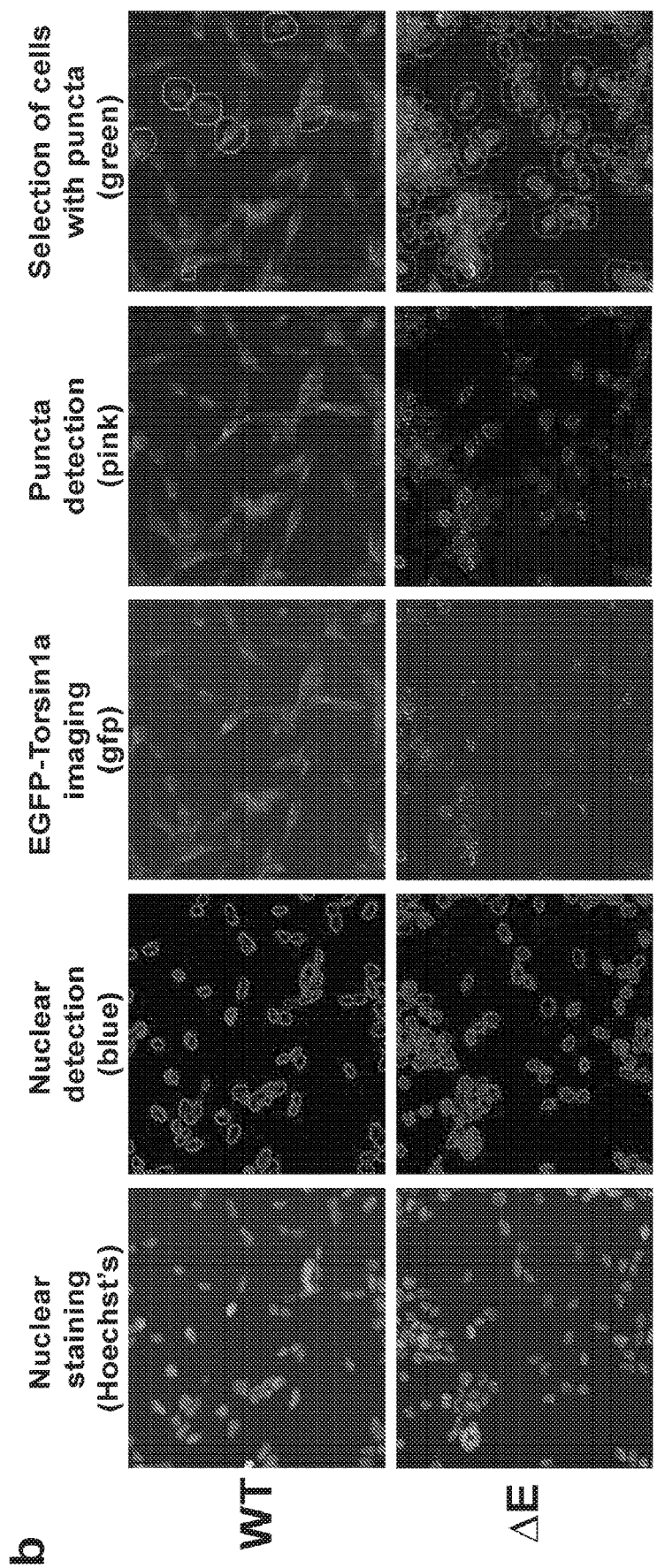
Figure 9:
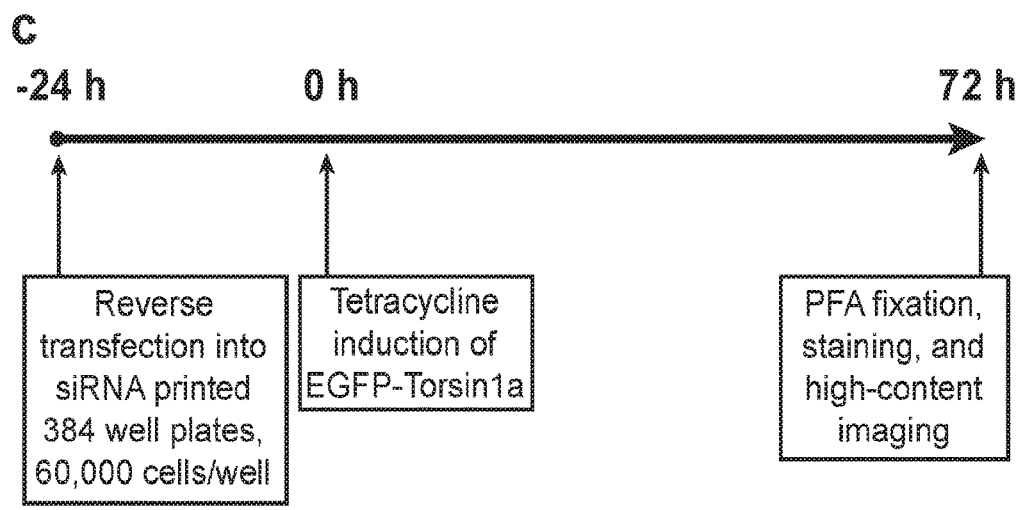
Figure 9:
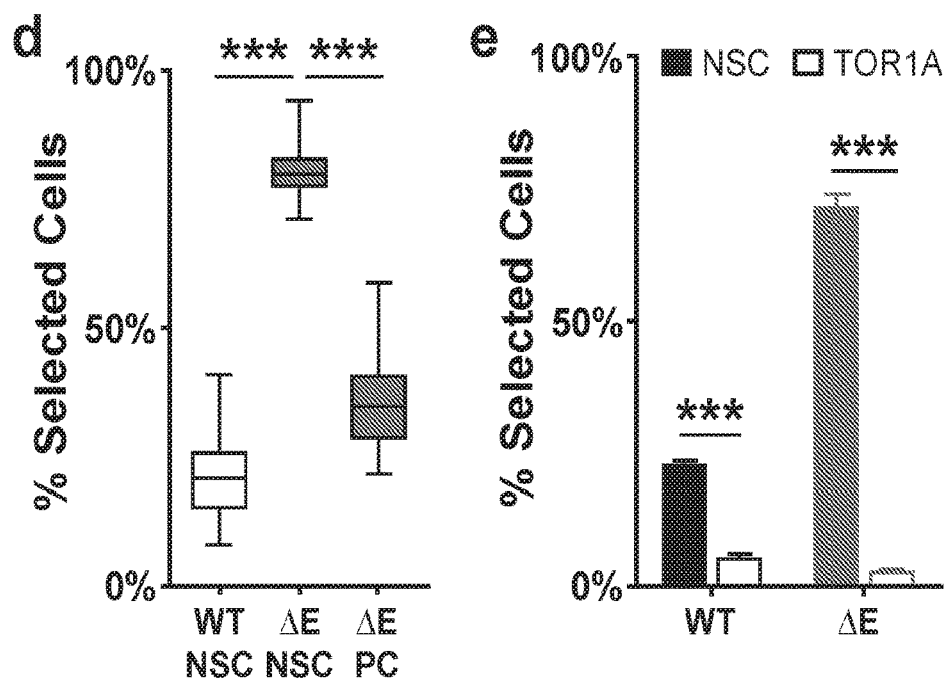

Image Analysis:

Development and validation of the high-content image analysis and assay performance under high-throughput screening conditions is presented in FIG. 9. The image analysis algorithm was developed using the Cellomics ArrayScan V CompartmentAnalysisV2 protocol. Hoechst's nuclear staining (Ch1: excitation 350 nm; emission 461 nm) was used for focusing and for cell identification by nuclear size, shape, and intensity. Automated exposure times for each plate were determined by setting a target saturation of 25% in channel 1 in wells containing tetracycline-induced delta-E cells. Detected cells were gated according to nuclear area, length-to-width ratio, and perimeter-to-area ratio. For the purpose of analysis, cell bodies were defined by a radius of 10 µm from the outer edge of the defined nucleus. Overlapping cells were automatically segmented according to the Cellomics ArrayScanV CompartmentAnalysisV2 object segmentation feature. EGFP fluorescence (Ch2: excitation 488 nm; emission 509 nm) was used for puncta detection. Automated exposure times for each plate were determined by setting a target saturation of 35% in channel 2 in wells containing induced delta-E cells. Torsin1a puncta were identified using the spot detection feature of the Compartmental AnalysisV2 protocol. The percentage of cells containing one or more puncta was used as the primary metric in this assay. As a technical control for the specificity of the signal, we confirmed that RNAi targeting Torsin1a eliminated inclusions (FIG. 9, panel e).

Messenger RNA Expression Profiling of Assay Cell Line

The gene expression profile of cells inducibly expressing delta-E Torsin1a was evaluated to identify mRNAs that are differentially expressed in the DYT1 model system.

Flp-In T-Rex 293 cells inducibly expressing delta-E Torsin1a were seeded at 2×106 cells per 10 cm2 dish. Cells were treated with tetracycline (5 µg/mL, Sigma #87128) or PBS (uninduced control) 24 h after initial plating. Cells were harvested 72 h after tetracycline induction. RNA was extracted using the Rneasy RNA extraction kit (Qiagen #74104) as per manufacturer's protocol. Microarray expression profiling was performed at the Duke Center for Genomic and Computational Biology (Durham, N.C.) using standard protocols and the GeneChip® Human Genome U133 Plus 2.0 Array (Affymetrix). The Affymetrix Gene Chip microarray data underwent strict quality control processing using the simpleaffy package in Bioconductor. Log-scale Robust Multiarray Analysis (RMA) from the affy package in Bioconductor was used for normalization to eliminate systematic differences across the arrays. The mas5 algorithm from the affy package was used to make present/absent calls. Bioinformatics analysis of RNAi screen hits was performed exclusively on probesets found to be present.

Differential gene expression data from microarray analysis shows that expression of 4 genes are up-regulated in response to EGFP-delta-E Torsin1a induction for 72 hours in our assay cell lines: HERPUD1, HSPA5(BiP), RAP1A, and MAP2K5 (Table 1).

(Thermo Fisher #13778150) (10 µL/well) was added 20 min prior to cell plating. Flp-In T-Rex 293 WT or delta-E Torsin1a cells were plated at 3,000 cells/well in 50 µL assay media [DMEM (Thermo Fisher #11965)+1% tetracycline-screened FBS (Hyclone #SH30070.03T)+1× GlutaMAX (Thermo Fisher #35050-061)+1% penicillin/streptomycin/amphotericin (Corning#30-004-Cl)], and incubated at 37° C./5% CO2 overnight. The following day, 15 µL assay media+26.7 µg/mL tetracycline (final tetracycline concentration: 5 µg/mL) was added to all wells except the uninduced control. Seventy-two hours after induction, cells were fixed with 4% PFA (Sigma #P6148) in PBS, permeabilized in PBS+0.5% Triton X-100 (Sigma #T8787), and stained with Hoechst 33342 nuclear dye (Sigma #B2261, 13.3 µg/mL in PBS). Plates were then sealed and imaged on a Cellomics ArrayScan automated high-content imaging system.

After identifying suitable screening conditions described above, a whole genome screen (WGS) targeting 22,909 human genes was performed (Qiagen Whole Genome siRNA Knock-Down Library 1.0). Four siRNAs targeting each gene were tested in a paired-screen design of two independent pools of two siRNAs each (FIG. 1, panel h). (See Panda, D. et al. (2011) *Proc. Natl. Acad. Sci. U.S.A* 108,

TABLE 1 mRNAs differentially expressed in delta-E Torsin1a expressing cells

| geneName | Tet.plus.mean | Tet.minus.mean | FoldChange | p. value | p. adj |
|---|---|---|---|---|---|
| RAP1A | 10.65499601 | 6.25273683 | 4.40225918 | 4.26E−014 | 1.65E−009 |
| RAP1A | 10.76761501 | 5.536435372 | 5.231179638 | 6.02E−014 | 1.65E−009 |
| MAP2K5 | 6.669384725 | 5.459748948 | 1.209635777 | 8.34E−008 | 0.001519571 |
| HERPUD1 | 12.03560636 | 11.40806375 | 0.627542606 | 1.58E−006 | 0.021536699 |
| HSPA5 | 12.27441717 | 11.63766644 | 0.636750727 | 1.99E−006 | 0.021803043 |
| HSPA5 | 8.553374401 | 7.893659664 | 0.659714737 | 2.78E−006 | 0.02531687 |

Example 2: Whole Genome siRNA Screen to Correct Delta-E Torsin1a Mis-Localization We first performed a pilot screen targeting 960 genes from the Qiagen Whole Genome siRNA Knock-Down Library 1.0 to determine the robustness of the assay system under automated high-content imaging, high-throughput screening conditions, and to establish that gene knockdown using siRNA could normalize delta-E Torsin1a distribution (FIG. 1, panels e-g; see also, FIG. 9, panel c). We thereby identified suitable screening conditions and a positive control siRNA pair (e.g., FIG. 1, panel g). WT and delta-E treated with non-silencing siRNA control or with positive control siRNA showed the ability to rescue the delta-E Torsin1a mis-localization phenotype (FIG. 1, panels e-g.) The reproducibility of the assay was established in multiple runs (FIG. 1, panel h).

The genome-wide RNAi screen on Flp-In T-Rex 293 cells inducibly expressing either WT or delta-E Torsin1a was performed at the Duke University RNAi screening facility (Durham, N.C.) by using the Qiagen genomic siRNA library v 1.0 consisting of four distinct siRNAs (A, B, C, and D) targeting 22,909 known and putative human genes as described in 27. Pairs of siRNAs (either AB or CD) in 5 µL of water (1 pmol/well) were added to clear-bottom 384-well plates (Corning #3712). Where appropriate, non-silencing siRNA (Qiagen #SI03650325) or TOR1B siRNAs (Qiagen #s SI00749574, SI04135404, SI04221728, and SI04270672) were added instead of library siRNAs. OptiMEM (Thermo Fisher #11058-021)+0.5% Lipofectamine RNAiMAX 19036-41; Barrows, N. J. et al., (2014) *Methods Mol. Biol.* 1138, 285-99; Harding, H. P. et al., (2003) *Mol. Cell* 11, 619-33.) Primary hits were defined as those genes whose knockdown improved delta-E Torsin1a localization by at least 3 standard deviations (from the mean of the non-silencing control siRNA (NSC)) and the effect was concordant, e.g. present in both of the two unique siRNA pools (FIG. 1, panel i). Hits that were cytotoxic, significantly decreased EGFP-Torsin1a expression, or were not expressed in the assay cell line (as determined by microarray analysis) were discarded. The primary images were then examined by blinded scorers and ranked to identify those hits that resulted in typical wild-type cellular morphology and Torsin1a distribution. The resulting group was used for pathway analysis and consisted of 93 high-stringency and high-quality hits (FIG. 1, panel j; Table 2).

TABLE 2

Gene hits used for pathway analysis

| HUGO Gene Symbol | Entrez Gene ID |
|---|---|
| AASS | 10157 |
| ACOT13 | 55856 |
| AGGF1 | 55109 |
| ANXA3 | 306 |
| ARHGEF11 | 9826 |
| ATG9A | 79065 |
| ATP13A1 | 57130 |
| ATP5A1 | 498 |

TABLE 2-continued

Gene hits used for pathway analysis

| HUGO Gene Symbol | Entrez Gene ID |
|---|---|
| BDP1 | 55814 |
| BOP1 | 23246 |
| C16orf58 | 64755 |
| C5orf44 | 80006 |
| CCDC86 | 79080 |
| CCZ1 | 51622 |
| CDCA4 | 55038 |
| CEBPD | 1052 |
| CEP78 | 84131 |
| CLEC4A | 50856 |
| CNOT6L | 246175 |
| COASY | 80347 |
| CTRB1 | 1504 |
| DDX24 | 57062 |
| DHX15 | 1665 |
| DIXDC1 | 85458 |
| DLL3 | 10683 |
| DNM1 | 1759 |
| DUSP5 | 1847 |
| EPDR1 | 54749 |
| ERMP1 | 79956 |
| ERO1LB | 56605 |
| EXOSC1 | 51013 |
| FAM92B | 339145 |
| FLRT2 | 23768 |
| GOLGA1 | 2800 |
| GP1BB | 2812 |
| HERC2P9 | 440248 |
| HHEX | 3087 |
| HIGD2B | 123346 |
| HNRPULI | 11100 |
| JPH1 | 56704 |
| K1AA1257 | 57501 |
| KMT2A | 4297 |
| LOC285033 | 285033 |
| LOC286186 | 286186 |
| LOC441204 | 442519 |
| MAML2 | 84441 |
| MERTK | 10461 |
| MRC2 | 9902 |
| NGLY1 | 55768 |
| NTPCR | 84284 |
| P4HTM | 54681 |
| PBX2 | 5089 |
| PCDHGB3 | 56102 |
| PHACTR3 | 116154 |
| POLR2E | 5434 |
| POLR2K | 5440 |
| PPP1R16A | 84988 |
| PRRG1 | 5638 |
| PSMD4 | 5710 |
| PTF1A | 256297 |
| PVT1 | 5820 |
| RBM3 | 5935 |
| RPAP3 | 79657 |
| RPL10A | 4736 |
| RPL10L | 140801 |
| RPL11 | 6135 |
| RPL12 | 6136 |
| RPL39 | 6170 |
| RPL5 | 6125 |
| RPL6 | 6128 |
| RPUSD4 | 84881 |
| SCD | 6319 |
| SH2D3C | 10044 |
| SPANXC | 728712 |
| SPDYE4 | 388333 |
| SPPL2A | 84888 |
| SPTLC1 | 10558 |
| SRGAP3 | 9901 |
| SRP19 | 6728 |
| SRP68 | 6730 |
| SRPR | 6734 |
| SSBP2 | 23635 |
| TAF15 | 8148 |
| TGFB1 | 7040 |
| TMEM258 | 746 |
| TRAPPC3 | 27095 |
| UBE21 | 7329 |
| UGT8 | 7368 |
| UNG | 7374 |
| WBSCR22 | 114049 |
| W1BG | 84305 |
| XAGE1D | 9503 |
| Y1PF3 | 25844 |

Example 3: Hit Validation and Bioinformatics Analysis

To cross-validate WGS hits in a system that did not rely upon exogenous expression of Torsin1a or a fusion protein, four of the highest-quality hits were tested in an orthogonal counter screen using patient-derived fibroblasts. We tested each shRNA for its ability to rescue a previously described defect in luciferase secretion. Chen, P. et al. (2010) *Hum. Mol. Genet.* 19, 3502-15; Cao, S. et al. (2010) *Dis. Model. Mech.* 3, 386-96; Barrows, N. J., et al., (2010) *J. Biomol. Screen.* 15, 735-47.) DYT1 patient data were obtained from 4 independent patient-derived lines and WT data (black bar) from 3 normal healthy control lines. Each line was tested in 5 independent experiments that included 4 technical replicates each (with the exception of SCD data from 3 independent experiments). Three of the four hits tested also improved this DYT1-related phenotype (FIG. 1, panel k). Bioinformatic analysis was then conducted, which identified eleven significantly over-represented signaling pathways (Table 3).

TABLE 3

Bioinformatic analysis of whole genome RNAi screen hits.

| | Ingenuity Canonical Pathways | p-value |
|---|---|---|
| 1 | EIF2 Signaling (6) | 0.000098 |
| 2 | Assembly of RNA Polymerase II Complex (3) | 0.0011 |
| 3 | Cell Cycle: G1/S Checkpoint Regulation (3) | 0.0019 |
| 4 | Glucocorticoid Receptor Signaling (5) | 0.0041 |
| 5 | Nucleotide Excision Repair Pathway (2) | 0.0087 |
| 6 | Notch Signaling (2) | 0.010 |
| 7 | Coenzyme A Biosynthesis (1) | 0.012 |
| 8 | Estrogen Receptor Signaling (3) | 0.015 |
| 9 | Lysine Degradation II (1) | 0.020 |
| 10 | Ceramide Biosynthesis (1) | 0.024 |
| 11 | Oleate Biosynthesis II (Animals) (1) | 0.048 |

The most highly enriched pathway among WGS hits—as well as among hits derived from an additional, less stringent WGS analysis (2SD effect size), was eukaryotic initiation factor 2a (eIF2-alpha) signaling, also known as the integrated stress response (ISR) (FIG. 2a). (Sidrauski, C. et al., (2013) *Elife* 2, e00498; Hinnebusch, A. G. & Lorsch, J. R., (2012) *Cold Spring Harb. Perspect. Biol.* 4.) Briefly, in the integrated stress response, eIF2-alpha, the rate-limiting regulatory subunit of the eIF2 complex which mediates the binding of methionyl-tRNA to the ribosome to begin protein translation (Vattem, K. M. & Wek, R. C., (2004) *Proc. Natl. Acad. Sci. U.S.A* 101, 11269-74), is phosphorylated by four upstream stress-sensitive kinases. Phosphorylation of eIF2- alpha has two main effects: a general decrease in the rate of protein translation and an increase in the translation of a subset of transcripts containing upstream open reading frames (uORFs). (Jackson, R. J., et al., (2010) *Nat. Rev. Mol. Cell Biol.* 11, 113-27; Harding, H. P. et al., (2000) *Mol. Cell* 6, 1099-108.) Principal among the transcripts whose translation is upregulated is ATF4, a transcription factor which stimulates the expression of stress response proteins. (Jackson, R. J., et al., (2010) *Nat. Rev. Mol. Cell Biol.* 11, 113-27; Fullwood, M. J., et al., (2012) *Prog. Mol. Biol. Transl. Sci.* 106, 75-106.) Eukaryotic initiation factor 2a signaling also leads to the expression of the protein phosphatase 1 regulatory subunits CreP and GADD34, which dephosphorylate eIF2-alpha and terminate ISR activation. (Boyce, M. et al., (2005) *Science* 307, 935-9.)

Example 4: Pharmacological Characterization of the Effects of eIF2-Alpha Signaling on Torsin1A Localization Although the screen implicated eIF2-alpha signaling, the hits that yielded the bioinformatics result (FIG. 2, panel b) did not reveal the directionality of the signaling change normalizing delta-E Torsin1a localization. However, knockdown of each of the four eIF2-alpha kinases significantly worsened delta-E Torsin1a localization (FIG. 2, panels a, b) indicating that decreased eIF2-alpha signaling has a deleterious effect on delta-E Torsin1a localization. These results also suggest a mechanism in which promoting eIF2-alpha pathway signaling, e.g. suppression of eIF2-alpha activity, would be beneficial.

Figure 2:
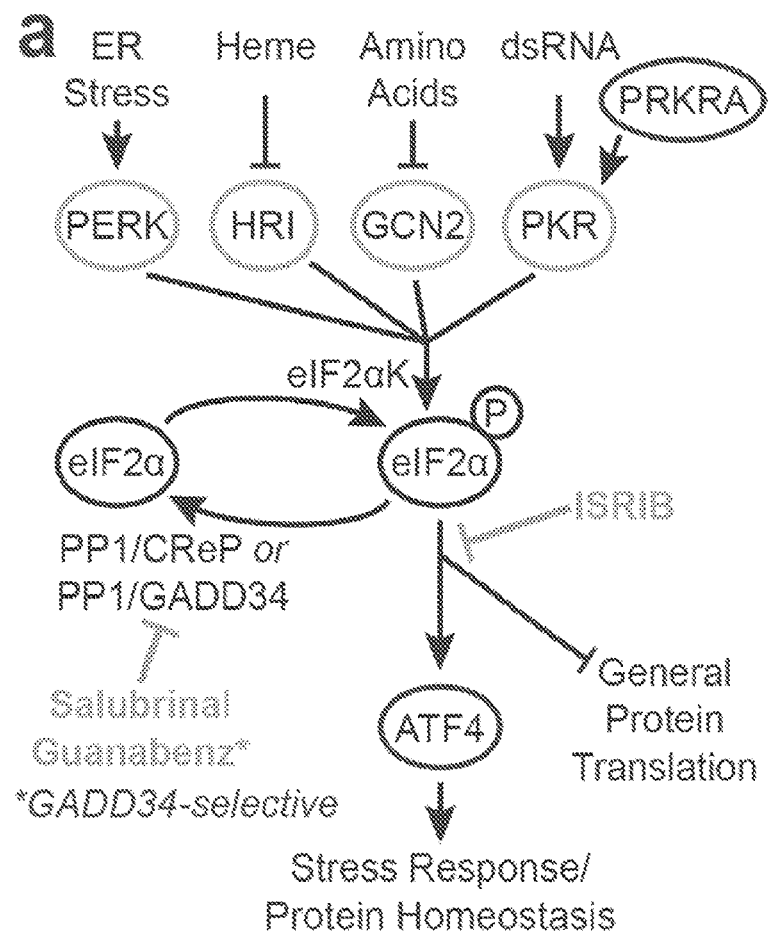
FIG. 2 shows that enhancement of eIF2-alpha (also referred to as "eIF2α") corrects delta-E Torsin1a mis-localization. Panel (a) shows a diagram of the eIF2-alpha signalling pathway. Proteins whose knockdown worsened the percentage of cells with punctate delta-E Torsin1a in the whole genome screen (WGS) are indicated by circles. Panel (b) shows WGS results relevant to the eIF2-alpha pathway. Dashed lines indicate 3 Standard Deviations from mean (solid line). Panels (c-h), left panels, show the effects of the indicated compounds on Torsin1a localization (black circles), cell count (grey squares), and EGFP-Torsin1a expression (grey triangles) in the delta-E (panels c-e, g, h) or WT (panel f) assay cell lines. Right panels show representative images from the respective treatments. Scale bars=20 μm. All data are presented as means±S.E.M. Panels (i) and (j) show that DMSO vehicle control has no effect on WT Torsin1a localization (i) or cell count (j).
Figure 2:
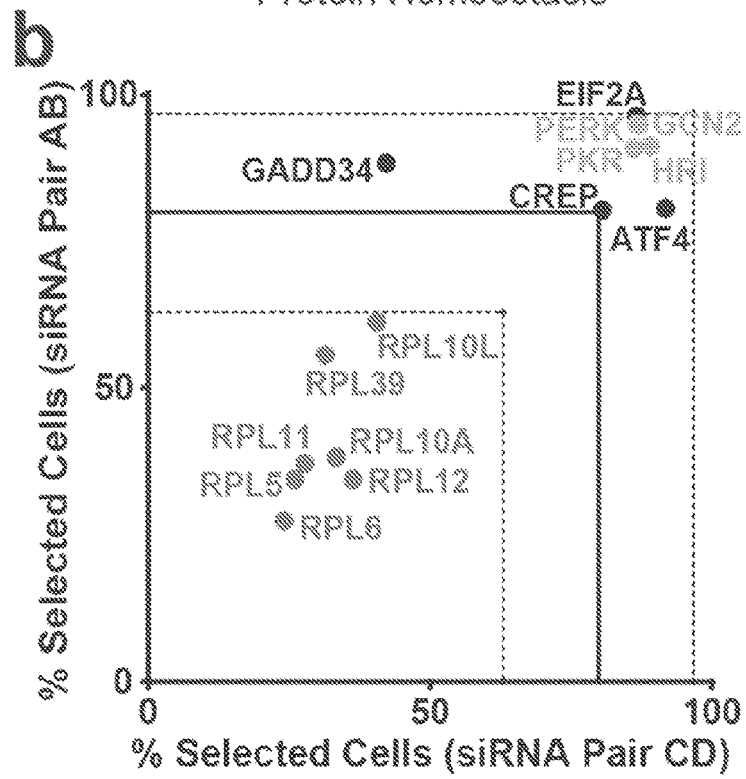
Figure 2:
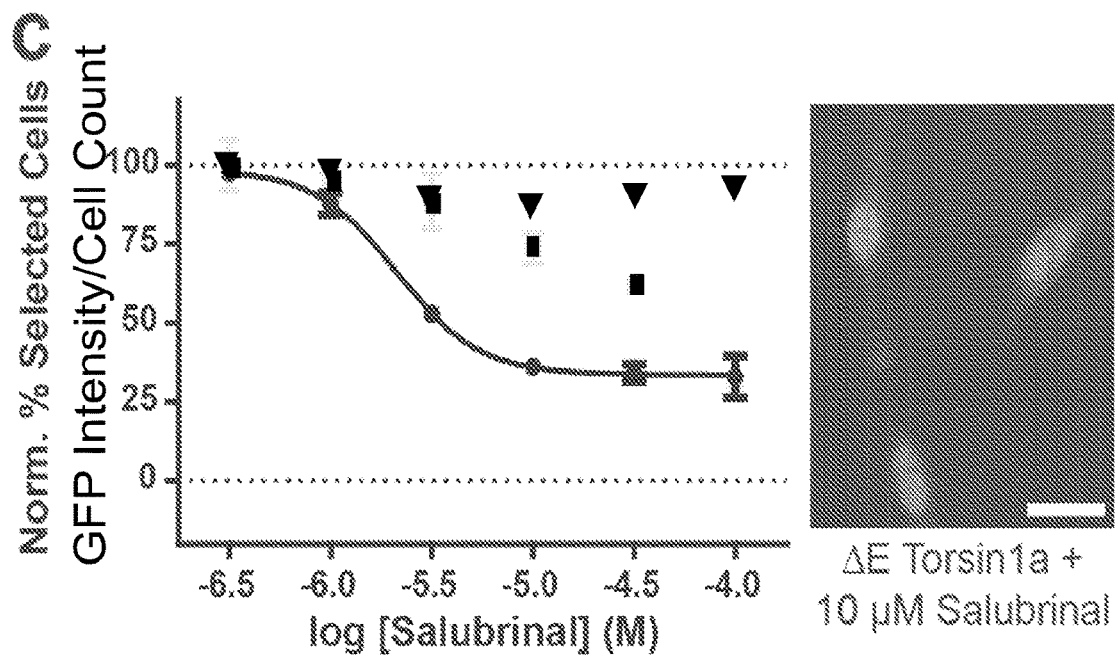
Figure 2:
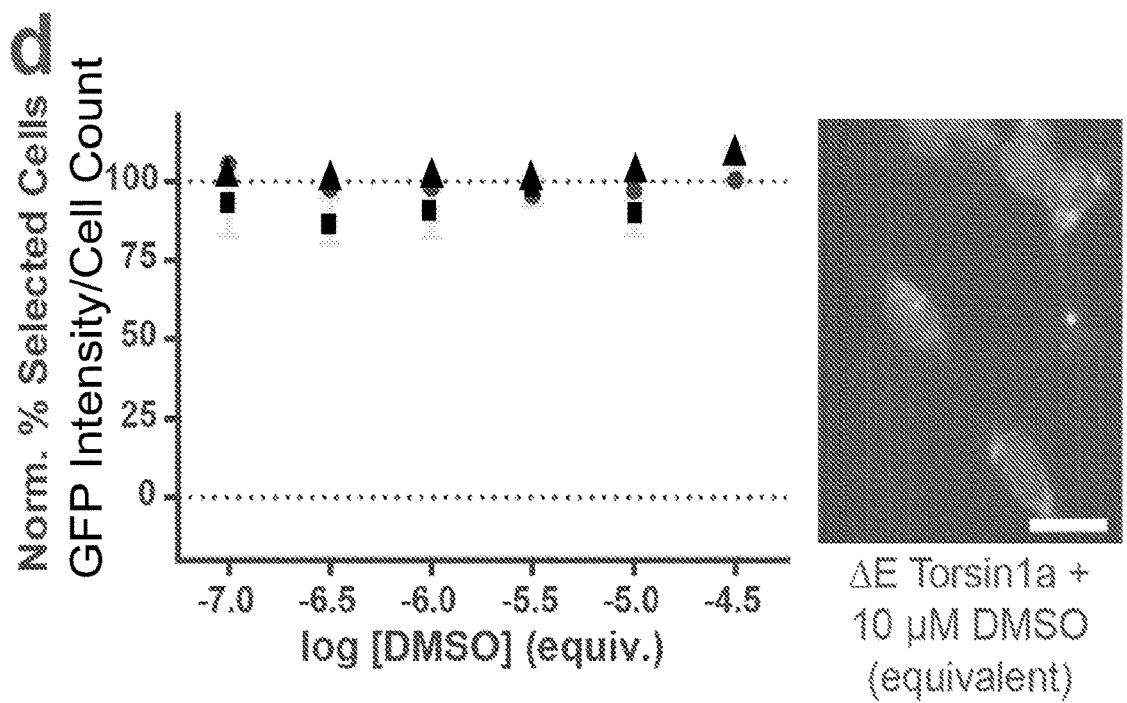
Figure 2:
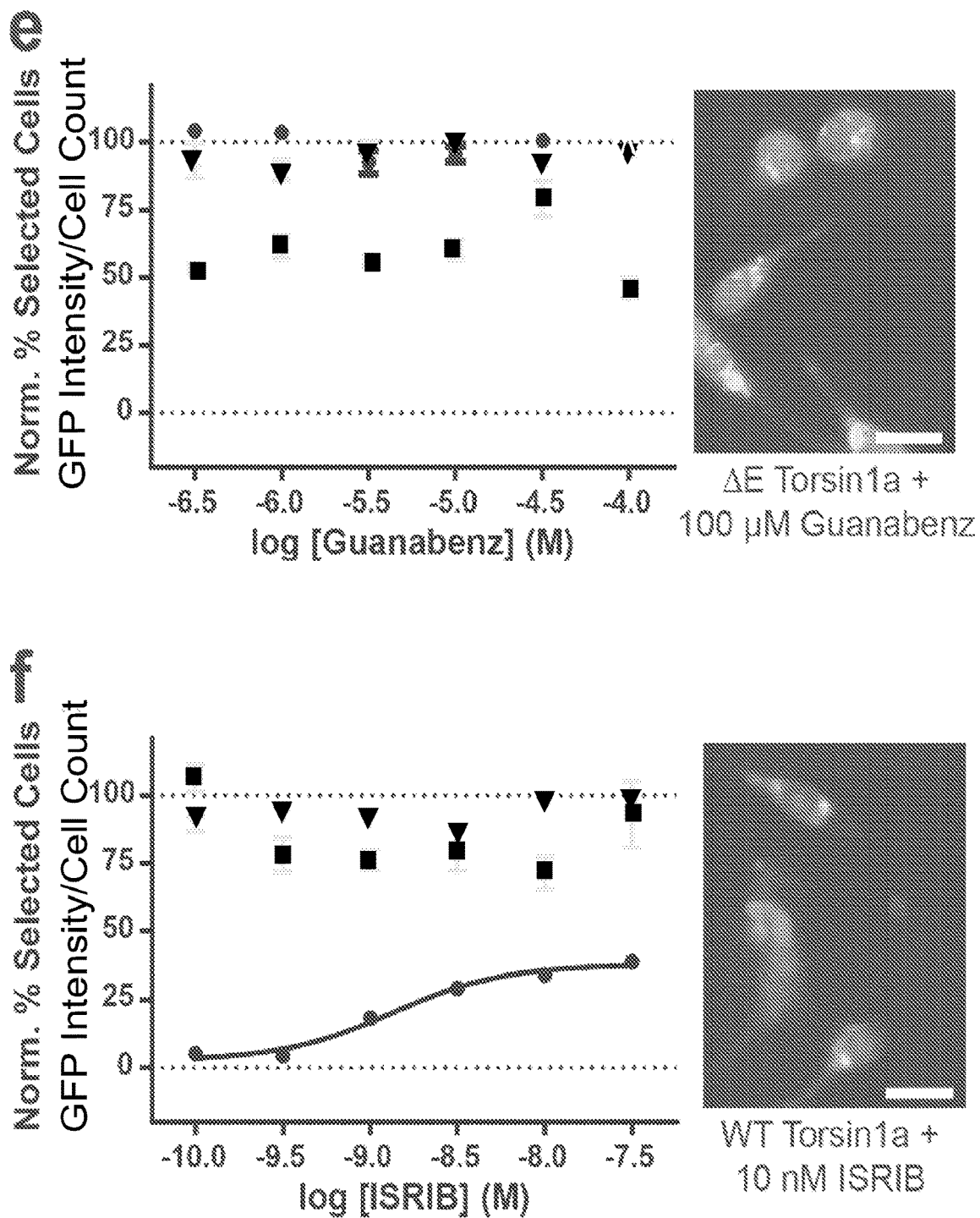
Figure 2:
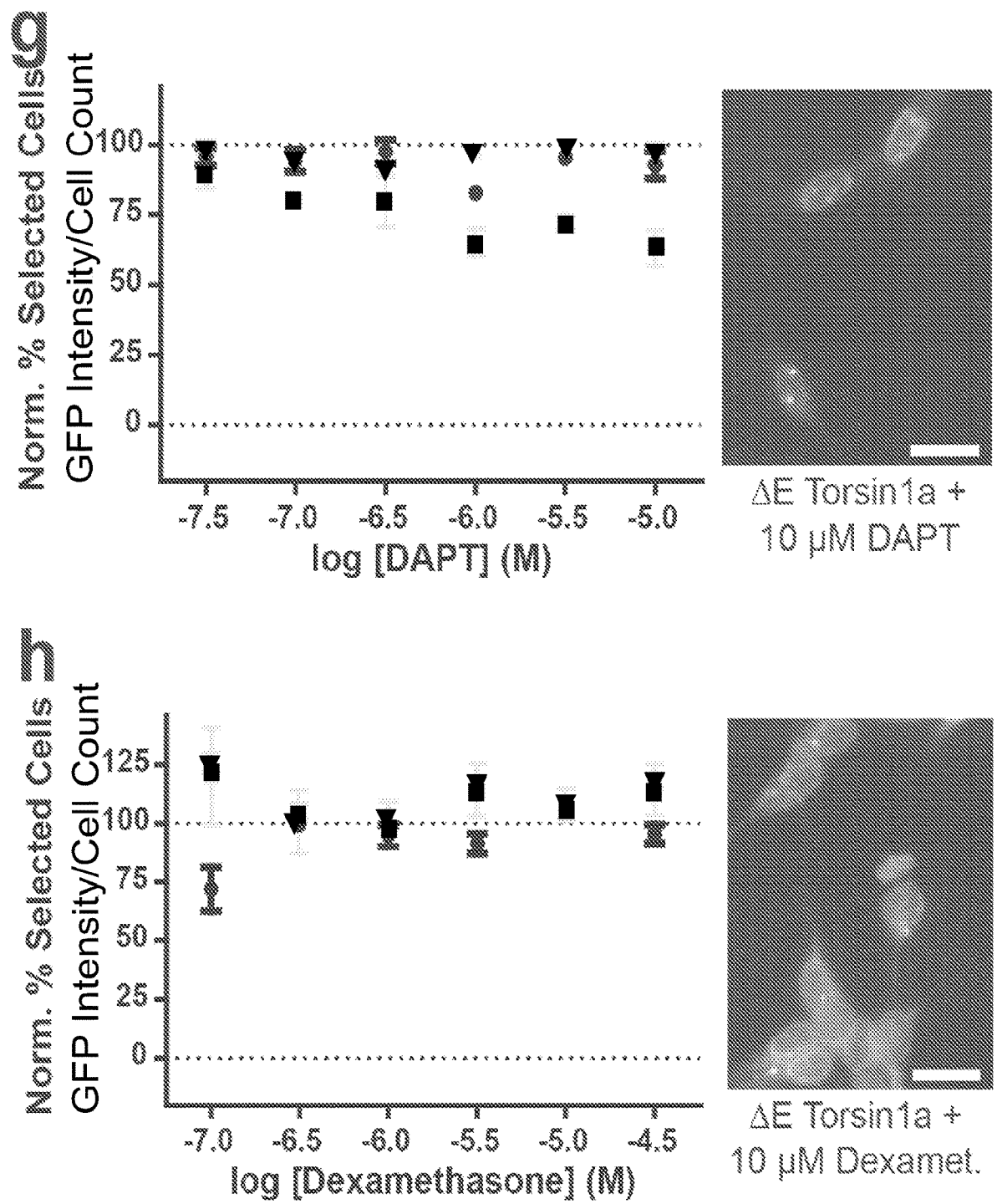
Figure 2:
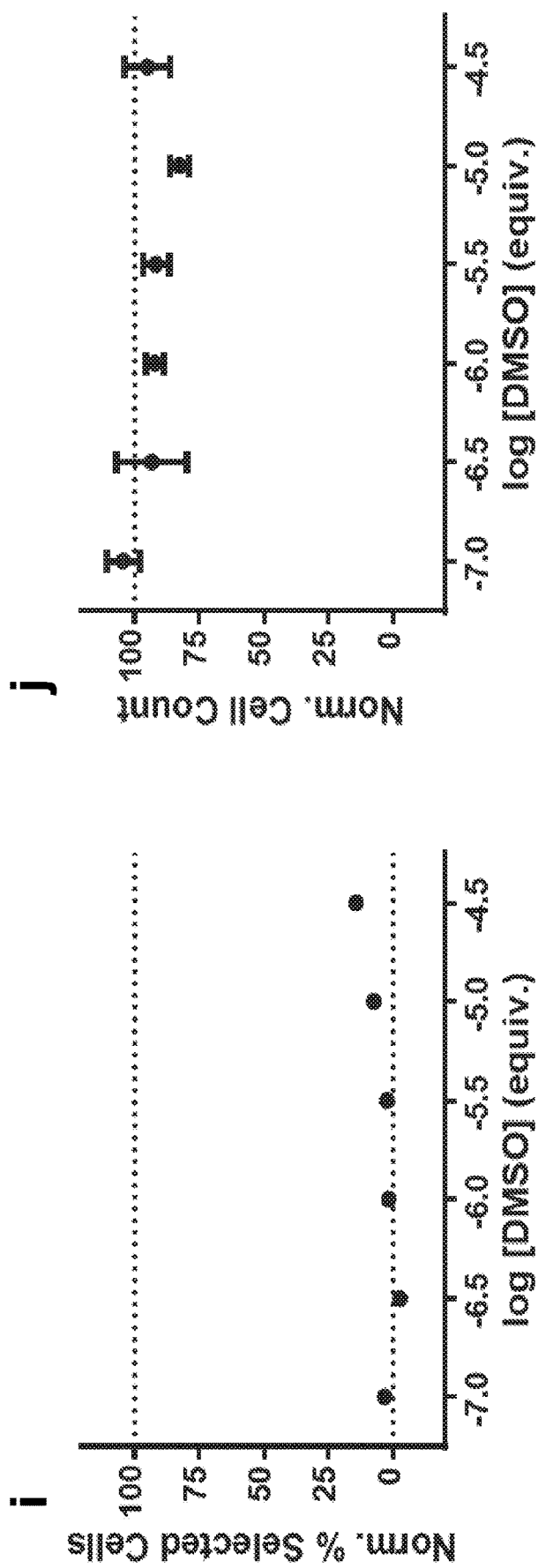

In order to test this model directly, the delta-E Torsin1a cell line was treated with compounds targeting the eIF2-alpha signaling pathway (FIG. 2). Flp-In T-REx 293 cells inducibly expressing either WT or delta-E Torsin1a were plated in clear-bottom 384-well plates (Corning #3712) at 3,000 cells/well in 30 μL assay media [DMEM (Thermo Fisher #11965)+1% tetracycline-free FBS (Hyclone #SH30070.03T)+1× GlutaMAX (Thermo Fisher #35050-061)+1% penicillin/streptomycin/amphotericin (Corning #30-004-Cl)], and incubated at 37° C./5% $CO^2$ overnight. The following day, serial drug dilutions were prepared at 2× final concentration in assay media containing 10 μg/mL tetracycline and 30 μL of the drug/tetracycline mixture was added to the appropriate wells, while control wells received 30 μL of assay media alone or assay media+10 μg/mL tetracycline (final tetracycline concentration for all wells except negative controls: 5 μg/mL). Cells were then incubated at 37° C./5% $CO^2$ for 48 hours and fixed, permeabilized, Hoechst stained, and imaged as described above. The range of the Torsin1a localization effect was normalized to the percentage of cells with puncta in vehicle-treated delta-E cell line as the maximum and that in WT cell line as the minimum (FIG. 2, panels c-h). Cell count and EGFP-Torsin1a expression were normalized to their respective values in the vehicle-treated delta-E cell line as the maximum. All dose response data are the average of 4 independent experiments per dose. Untreated control data used for normalization are the average of 24 independent experiments.

Salubrinal (R&D Systems #2347), a drug that prolongs ISR activation by promoting eIF2-alpha phosphorylation (Tsaytler, P., et al., (2011) *Science* 332, 91-4), caused a robust dose-dependent normalization of delta-E Torsin1a localization, without modifying steady-state EGFP-Torsin1a levels or significant toxicity or obvious alterations of cellular morphology at effective concentrations (EC50=2.12 μM) (FIG. 2, panel c). As a control, we confirmed that treatment with vehicle (DMSO) at concentrations present in these experiments had no effect on the rate of delta-E or WT Torsin1a inclusions or cell number (FIG. 2, panel d). In addition, none of the compounds tested significantly altered steady-state levels of EGFP-Torsin1a (FIG. 2, grey triangles in all panels).

Another eIF2-alpha phosphatase inhibitor, guanabenz, had no effect on delta-E Torsin1a localization (FIG. 2, panel e). Guanabenz, however, is a more selective inhibitor of GADD34-containing eIF2-alpha phosphatase complexes (Stockwell, S. R. et al., (2012) *PloS One* 7, e28568), suggesting that activity of both GADD34- and CreP-containing PPI complexes may need to be silenced in order to normalize delta-E Torsin1a localization. Consistent with this possibility, neither GADD34 nor CreP was identified as a hit in the RNAi screen (FIG. 2, panel b).

We next examined the efficacy of a direct activator of the eIF2-alpha kinase PERK, CCT02031238. CCT020312 also caused a dose-dependent reduction in the number of cells with Torsin1a inclusions. However, CCT020312 treatment was highly toxic at effective concentrations, as indicated by both cell count and cellular morphology. Thus, collectively these experiments suggest that positive modulation—as opposed to direct activation—of eIF2-alpha signaling may be more easily tolerated and therefore more likely to be of therapeutic value.

Upon finding that prolonged signaling through eIF2-alpha phosphorylation normalizes delta-E Torsin1a distribution (e.g., FIG. 2, panel c), it was then determined whether preventing such signaling would alter the normal distribution of Torsin1a. To do this, the compound ISRIB, which prevents the downstream signaling consequences of eIF2-alpha phosphorylation, (Hinnebusch, A. G. & Lorsch, J. R., (2012) *Cold Spring Harb. Perspect. Biol.* 4; Patil, C. & Walter, P., (2001) *Curr. Opin. Cell Biol.* 13, 349-55), was tested on the WT Torsin1a-expressing assay cell line. ISRIB caused a dose-dependent increase in cells with punctate Torsin1a localization without effects on Torsin1a expression levels (FIG. 2, panel f). These findings indicate a dynamic role for the ISR pathway in bi-directionally regulating Torsin1a localization.

Finally, compounds were tested targeting two other pathways enriched among the WGS hits, notch signaling and glucocorticoid signaling, and another ER stress response pathway. Treatment with the y-secretase inhibitor, DAPT, which blocks notch signaling, had no effect on delta-E Torsin1a localization (FIG. 2, panel g), nor did the anticonvulsant, valproic acid, which, among other activities, activates notch signaling. Similarly, neither the glucocorticoid receptor agonist dexamethasone (FIG. 2, panel h), or a small panel of additional compounds modulating glucocorticoi-dimineralocorticoid receptor signaling significantly modified delta-E Torsin1a localization. Lastly, because PERK-mediated eIF2-alpha signaling is one of three branches of the unfolded protein response (Dang, M. T. et al., (2005) *Exp. Neurol.* 196, 452-63), modulators that are available for another branch, which requires ATF6 signaling, were tested. We found that compounds targeting this branch primarily caused cytotoxicity. Furthermore, knockdown of ATF6 did not significantly normalize or worsen delta-E Torsin1a localization in the WGS screen.

Together, these results identify augmentation of signaling through the eIF2-alpha pathway as a specific, efficacious and non-toxic target to normalize delta-E Torsin1a mis-localization.

Example 5: Expression of ATF4 is Sufficient to Normalize Delta-E Torsin1a Localization The mechanisms downstream of eIF2-alpha phosphorylation that might be involved in mediating the normalizing effects of ISR signaling on delta-E Torsin1a localization was investigated. Phosphorylation of eIF2-alpha has two downstream consequences: a decrease in the general rate of protein translation and an increase in translation of a subset of transcripts containing uORFs, the most well-characterized of which is the transcription factor ATF4 (FIG. 2a). (Jackson, R. J., et al., (2010) Nat. Rev. Mol. Cell Biol. 11, 113-27.) Therefore, to determine if increased ATF4 expression alone was sufficient to normalize delta-E Torsin1a localization, we overexpressed ATF4 in the delta-E Torsin1a assay cell line.

Flp-In T-REx 293 cells inducibly expressing either WT or delta-E Torsin1a were plated as described above. The following day, cells were transfected with empty vector (pBluescript) or pRK/FLAG-ATF4 using Lipofectamine2000 (Thermo Fisher #11668) and Opti-MEM (Thermo Fisher #11058) according to the manufacturer's instructions (56 ng DNA/well, 10 µL total volume/well). 4 hours later, 20 µL of assay media+15 µg/mL tetracycline was added to each well (5 µg/mL final concentration), and cells were incubated at 37° C./5% $CO^2$ for 48 hours. Cells were then fixed, permeabilized, Hoechst stained, and imaged as described above. After initial imaging, cells were stained for FLAG-ATF4 as follows: 50 µL blocking solution [10% normal goat serum (Thermo Fisher #16210-064) in PBS] was added to each well and the cells were incubated for 20' at RT. Excess blocking solution was then aspirated and 50 µL primary antibody solution [mouse anti-FLAG Mj2 (Sigma #F3165), 1:1000 in blocking solution] was added to each well for 30' at RT. Cells were then washed twice with PBS and 50 µL secondary antibody solution [Alexa594-conjugated goat anti-mouse (Thermo Fisher #A-11005), 1:1000 in blocking solution] was added to each well for 30' at RT. Lastly, plates were washed 4 times with PBS, sealed, and re-imaged.

Figure 3:
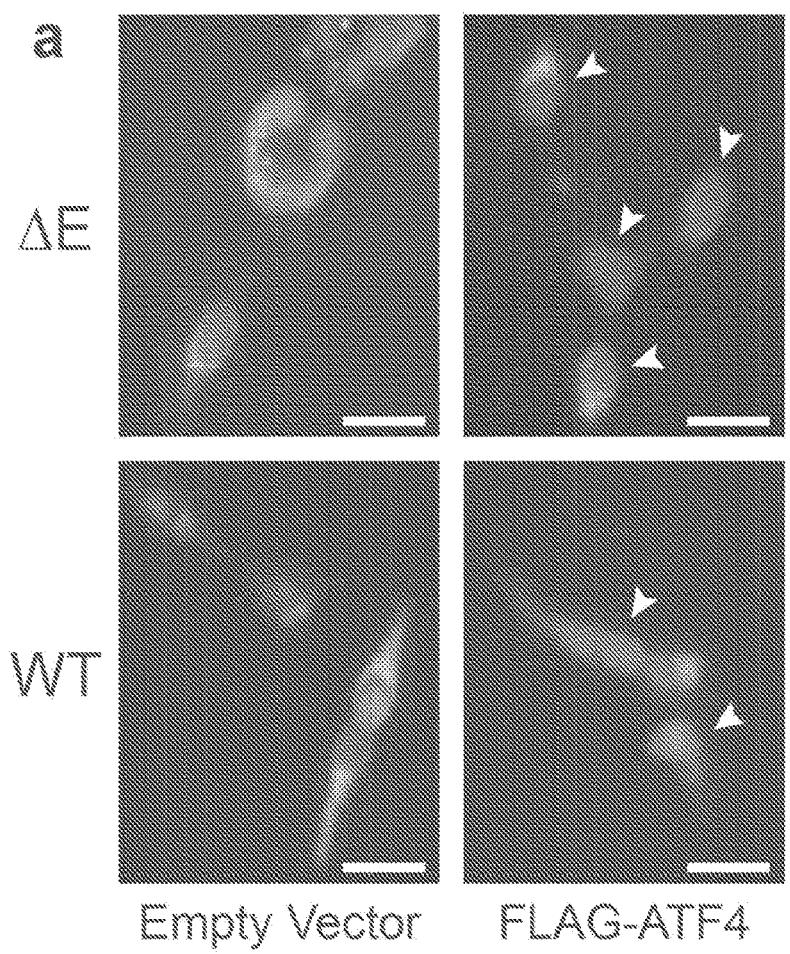
FIG. 3 shows that ATF4 overexpression is sufficient to correct delta-E Torsin1a mis-localization. Panel (a) shows representative images of EGFP-Torsin1a localization (light punctate staining) and FLAG epitope staining (white arrows) in the transfected delta-E and WT assay cell lines. Scale bars=20 μm. Panel (b) shows quantitation of data presented in panel (a). All data are presented as means±S.E.M. ***, p<0.0005 by unpaired t test.
Figure 3:
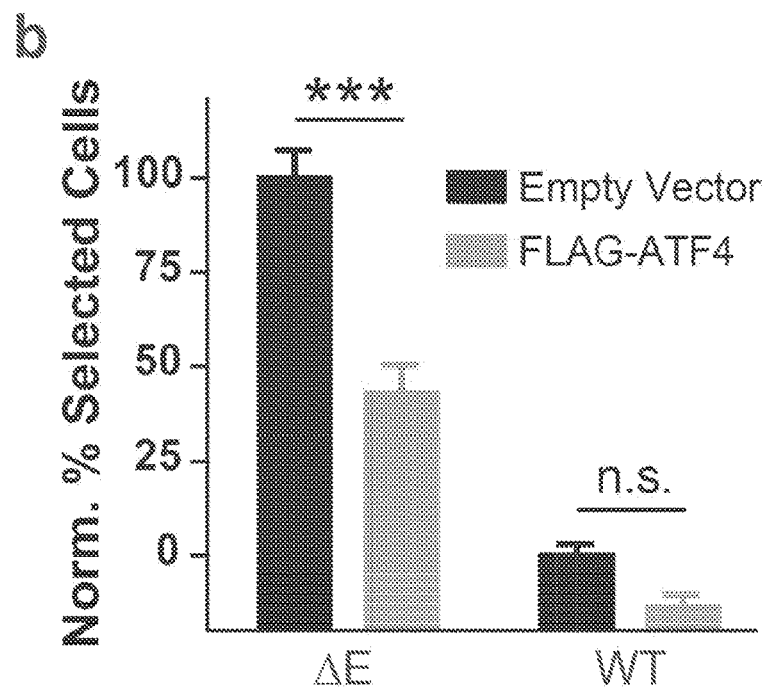

Representative images are presented in FIG. 3, panel (a). Quantitated data are presented in FIG. 3, panel (b). Quantitation range of the Torsin1a localization effect was normalized to the percentage of cells with puncta in vector control-transfected delta-E cell line as the maximum and that in WT cell line as the minimum. N=16 independent wells for each condition, and an additional 24 untransfected control wells used for normalization.

ATF4 overexpression significantly improved delta-E Torsin1a localization, with negligible effects on WT Torsin1a localization (FIG. 3a). Moreover, the magnitude of the effect was similar between salubrinal-treated and ATF4-expressing cells (FIGS. 2c and 3b; salubrinal efficacy=66.4%, ATF4 efficacy=57.0%).

Example 6: Enhancing eIF2-Alpha Signalling Improves Neonatal Survival of Homozygous DYT1 Knock-in Mice The findings above support a role for the eIF2-alpha signaling pathway in normalizing in vitro cellular phenotypes related to the DYT1 genotype. Next, the effect of targeting eIF2-alpha signaling on the deleterious consequences of the DYT1 TorsinA mutation was determined in vivo. Etiological mouse models of DYT1 dystonia have not had robust dystonic phenotypes. (Tanabe, L. M., et al., (2012) PloS One 7, e32245; Camargos, S. et al., (2008) Lancet. Neurol. 7, 207-15; Seibler, P. et al. (2008) Lancet. Neurol. 7, 380-1.) Nonetheless, another deleterious genotype-dependent effect of the mutation on the animal-neonatal lethality of homozygous delGAG knock-in mice—facilitated interrogation of the impact of eIF2-alpha targeting in vivo (FIG. 4a). (Seibler, P. et al. (2008) Lancet. Neurol. 7, 380-1; Goodchild, R. E., et al, (2005) Neuron 48, 923-32.)

Breeding and Viability Determination:

Pairs of heterozygous delta-E Torsin1a knock-in breeders (courtesy of Dr. W. Dauer, University of Michigan) were randomly assigned to vehicle or salubrinal treatment groups. Starting 10 days after breeding cages were established, each female mouse was given a daily subcutaneous injection of vehicle or salubrinal at approximately 6 p.m. Cages were checked for new pups three times per day: morning (~8 a.m.), early afternoon (~2 p.m.), and during injections (~6 p.m.). In order to minimize stress and the possibility of litter abandonment, mice with newborn pups were not given injections. Newborn pups were identified by marking limbs with a permanent laboratory marker, and tail samples were taken for genotyping at P0. At approximately P0.5, cages were checked again, and the status of each pup was recorded. If pups were first observed at the 8 am check, the 2 pm check was considered P0.5. If pups were first observed at the 2 pm or 6 pm checks, an additional check was performed at approximately midnight, and considered P0.5. Mortality was also tracked the following day, after which time identifying marks were predominately washed off or obscured by fur. Approximately 8 days after birth all remaining pups were sacrificed, and 10 days after birth daily injections resumed for the subsequent litter. All genotyping and, whenever possible, all pup identification and mortality checks were performed blinded to treatment group.

Drug Administration:

Salubrinal (R&D Systems #2347) stocks were prepared at 26 mM (10× final concentration) in DMSO and stored in single-use aliquots at −80° C. Each day immediately before injections, a single salubrinal aliquot was thawed to room temperature and diluted 1:10 in injection vehicle (final vehicle composition: 1×PBS/10%/DMSO/0.1% BSA). Empty injection vehicle was stored at room temperature in single-use aliquots. Mice were given a single subcutaneous injection of 3.3 mg/kg salubrinal (approximately 80 µL for a 30 g mouse) or an equivalent volume of empty injection vehicle.

N=29 vehicle- and 28 salubrinal-treated homozygous pups and 65 vehicle- and 91 salubrinal-treated pooled heterozygous and wild-type pups. No significant drug effect on mortality was observed for either wild-type or heterozygous genotype, so results were combined to simplify presentation (FIG. 4, panel b).

Figure 4:
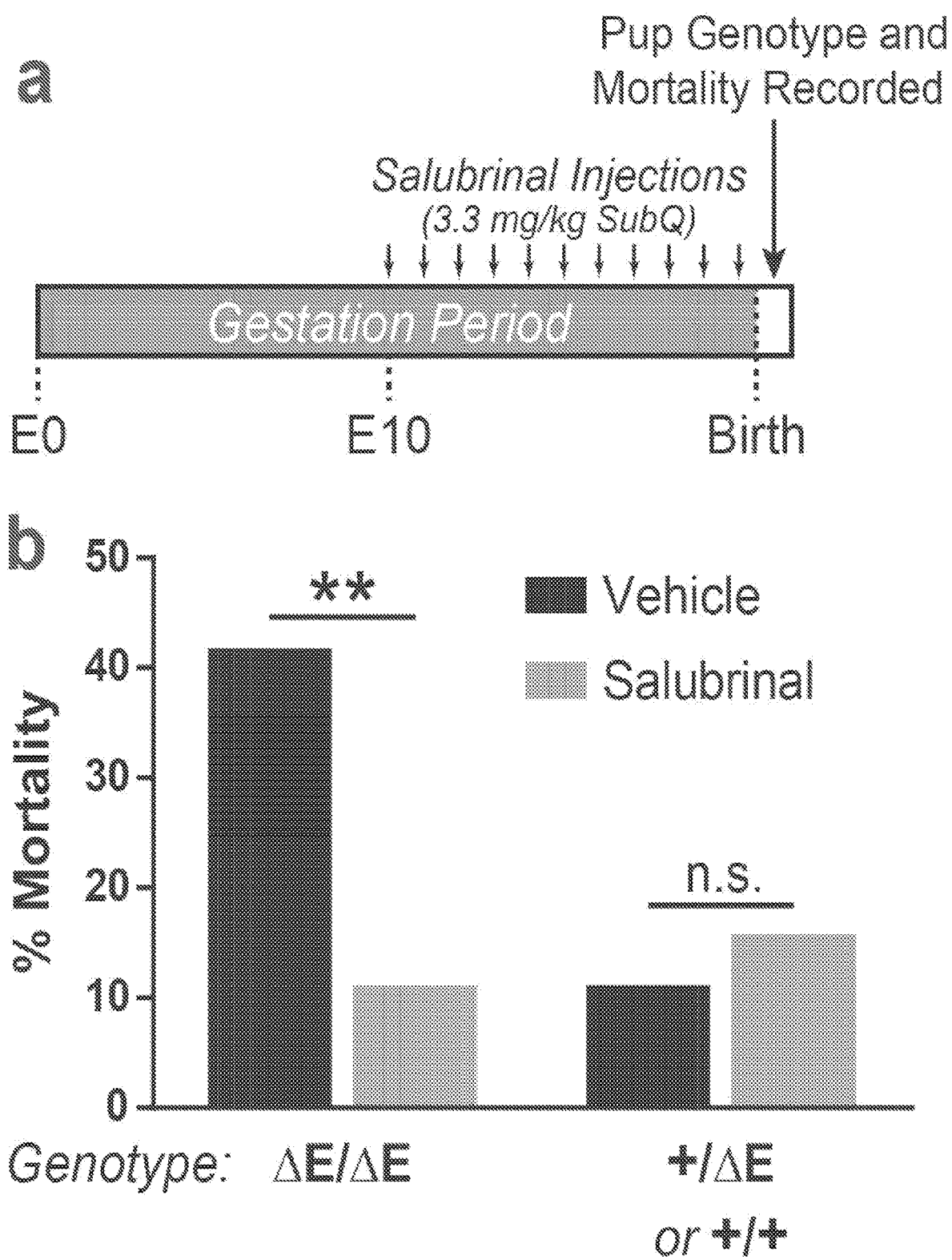
FIG. 4 shows that salubrinal improves perinatal survival of homozygous DYT1 knock-in mice. Panel (a) shows the experimental design of perinatal survival experiments. Panel (b) shows the effect of in utero salubrinal exposure on perinatal survival. **, p<0.01 by Chi-square test.

The eIF2-alpha phosphatase inhibitor salubrinal was administered daily to pregnant dams (in Tor1adelGAG/+× Tor1adelGAG/+breedings) from approximately embryonic day 10 through delivery and tested its effects on neonatal survival (FIG. 4, panel a). In comparison to litters from vehicle-treated dams, salubrinal dramatically reduced the mortality of delta-E/delta-E pups (FIG. 4, panel b). Additionally, there was no evidence that salubrinal had a non-specific mechanism in improving neonatal survival, as no mortality differences were observed between treatment and control groups in the remaining pups of either wildtype or heterozygote genotypes (FIG. 4, panel b). Although in this study design there was no postnatal salubrinal treatment except possibly through lacteal transfer (though homozygous delta-E/delta-E pups are known to not nurse), we anecdotally note that two salubrinal-treated homozygous delta-E Torsin1a pups survived through the second postnatal day. No vehicle-treated homozygous pups survived through even the first postnatal day.

Example 7: Stress-Induced eIF2-Alpha Signaling is Impaired in Cells from Human DYT1 Patients As described above, pharmacologically enhancing eIF2-alpha signaling can treat in vitro and in vivo DYT1 genotype-related dystonia phenotypes. However, a key remaining question was whether the eIF2-alpha signaling pathway was disrupted in DYT1 dystonia. To address this, we examined the integrity of the eIF2-alpha signaling pathway in fibroblasts derived from human DYT1 patients. We measured the well-known stress-induced increase in ATF4 expression as a readout of pathway activation.

Normal control and DYT1 patient human dermal fibroblasts were plated in 6-well plates at 25,000 cells/well in FGM media (2 mL/well) and incubated 37° C./5% CO2 for 4 days. Media was replenished with FGM (1 mL/well) and incubated at 37° C./5% CO2 overnight. Opti-MEM (1 mL/well) containing 2 μg/mL thapsigargin (Santa Cruz Biotechnology #sc-24017) was added to cells and incubated as indicated (final concentration: 1 μg/mL).

Cells were harvested in RIPA buffer [150 mM NaCl/50 mM NaH2PO4/2 mM EDTA/1 % Triton X-100/0.5% SDS/0.5% deoxycholic acid/50 mM NaF/10 mM Na4P2O7/1 mM Na3VO4/1× phosphatase inhibitor cocktail (Sigma #P5726)/1× cOmplete Mini EDTA-free protease inhibitor cocktail (Roche #04693159001)]. Total protein concentrations were assessed by BCA assay (Thermo Fisher Scientific #23225). Proteins were resolved on 4-15% TGX gels (Bio-Rad #5671085), transferred to nitrocelulose membrane, blocked in TBS-T+5% non-fat dry milk, and probed as indicated. (Primary antibodies employed in the examples of the disclosure are presented in Table 4.) ATF4 expression was normalized to 1-actin expression. N=3 independent control cells lines and 4 independent DYT1 cell lines, 3 replicates each.

TABLE 4

Primary antibodies used in the Examples.

| Reactivity | Supplier | Cat. # | Dilution |
| --- | --- | --- | --- |
| β-Actin | Millipore | MAB1501 | 1:1,000 |
| FLAG | Sigma | F3165 | 1:1,000 |
| ATF4 | Santa Cruz Biotechnology, Inc. | SC-200 | 1:500 |
| CreP | Proteintech | 14634-1-AP | 1:500 |
| GAPDH | Abcam | ab9485 | 1:1,000 |

Figure 5:
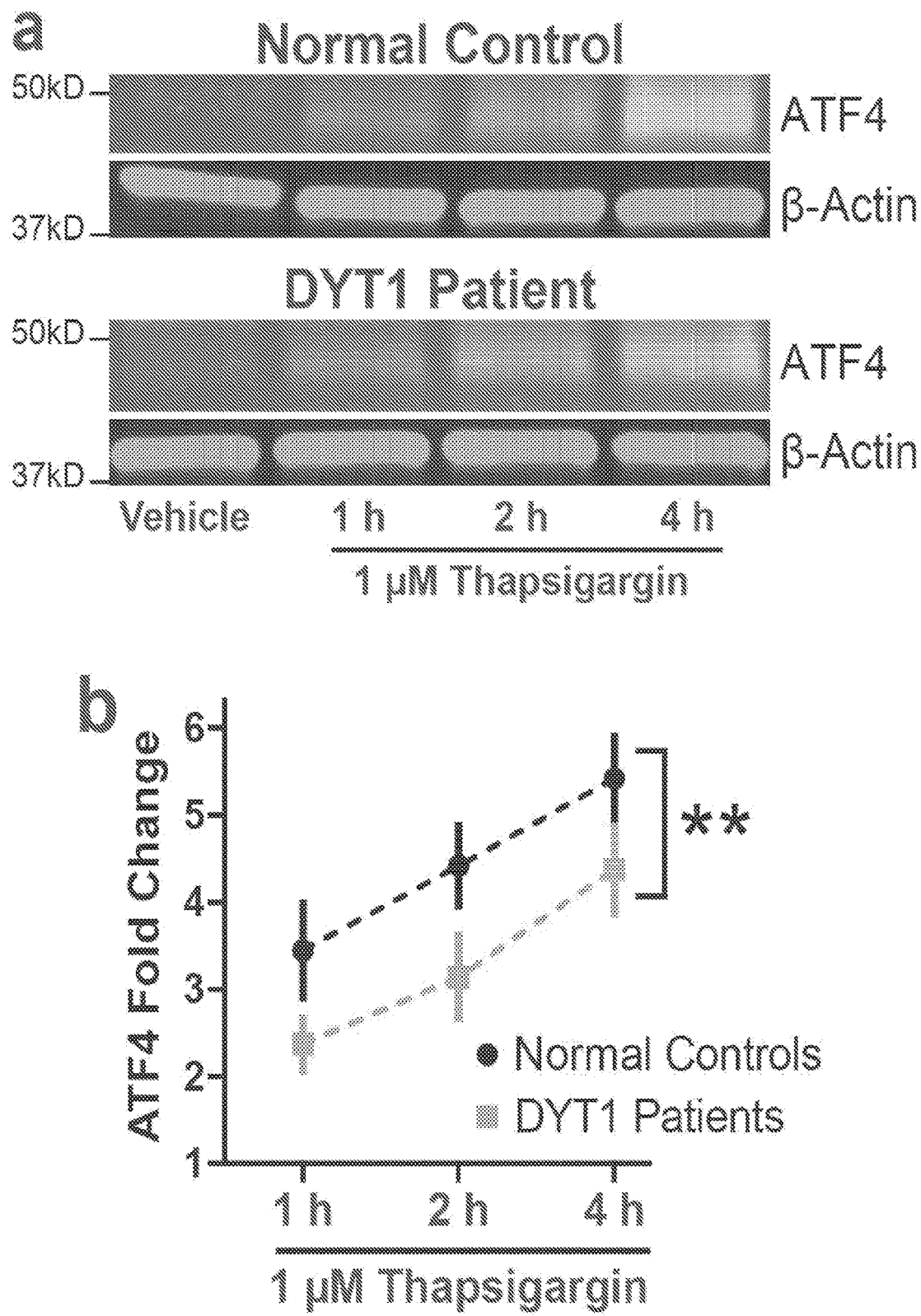
FIG. 5 shows molecular and genetic analyses establishing eIF2α pathway dysfunction in DYT1 and sporadic dystonia patients. Panel (a) shows Western blot analysis of ATF4 levels in fibroblasts derived from DYT1 patients, and healthy control cells, at various times following thapsigargin treatment. Blots were re-probed for β-actin as a loading control. Panel (b) shows quantitation of the data presented in panel (a). , p<0.005 by two-way ANOVA. Panel (c) shows the results of whole exome sequencing of patients with sporadic dystonia patients and normal controls. Among these is a p.P46L mutation in ATF4, an eIF2-alpha pathway gene. Panel (d) shows that the P46L mutation reduces ATF4 transcriptional activity relative to WT or another common ATF4 variant (Q22P). , p<0.005 by unpaired t test. Panel (e) shows representative Western images revealing reduced steady-state levels of P46L ATF4 relative to WT controls. ATF4 expression was normalized to GAPDH. Panel (f) shows quantification of reduced P46L FLAG-ATF4 levels. *, p<0.05 by unpaired t test. Panel (g) shows the ratio of ATF4 levels (normalized to GAPDH) under proteasomal inhibition relative to untreated (MG132/untreated) controls. **, p<0.005 by unpaired t test. All data are presented as means±S.E.M.
Figure 5:
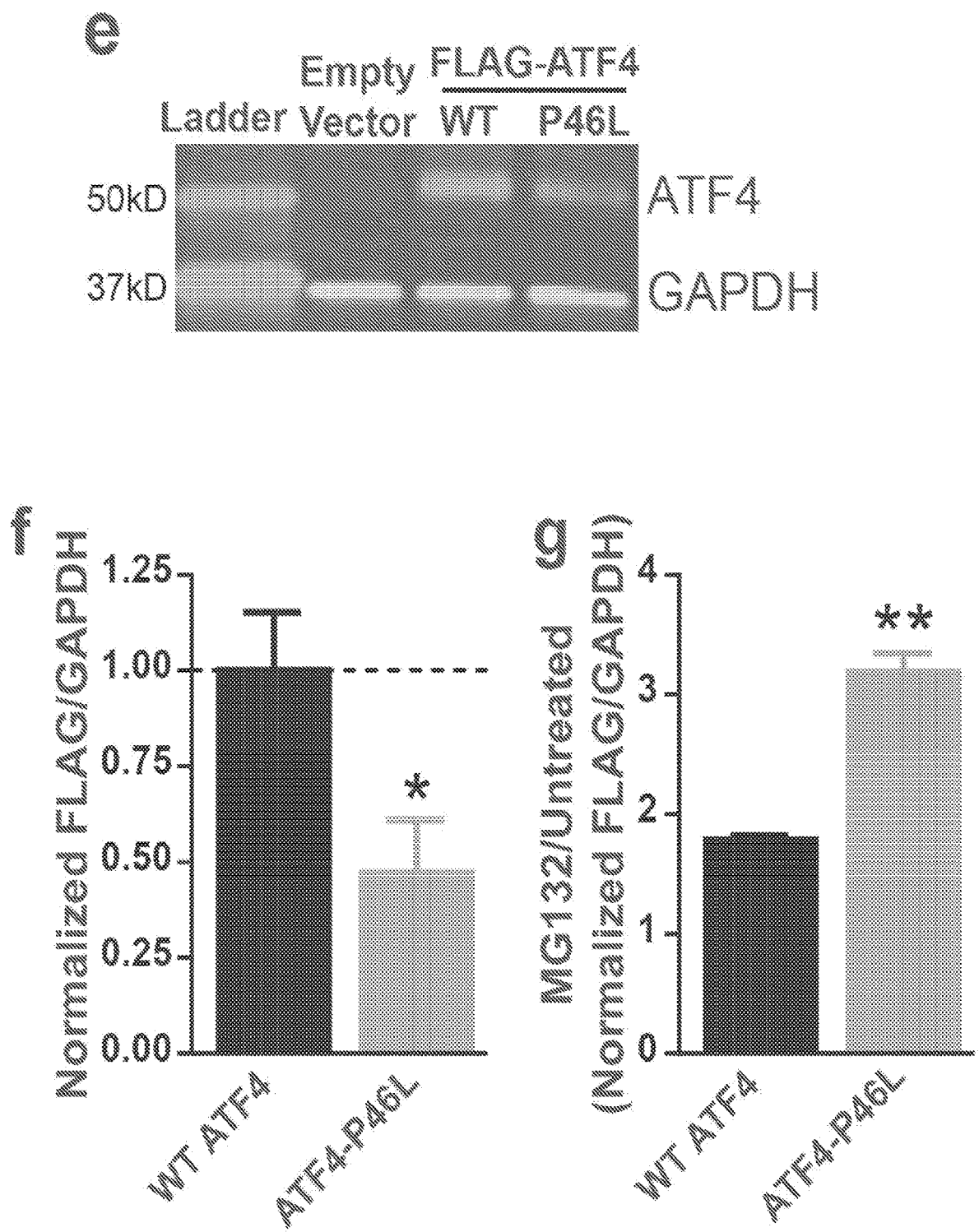

Representative images and quantitation are presented in FIG. 5, panels a, b. Strikingly, we found that ATF4 upregulation in response to the ER stressor thapsigargin was impaired in DYT1 patient-derived fibroblasts relative to fibroblasts from patients without disease (FIG. 5). This result provides evidence that eIF2-alpha signaling is disrupted in DYT1 dystonia.

Example 8: Identification of a Loss-of-Function ATF4 Mutation in Sporadic Dystonia Patients Interestingly, another rare inherited dystonia supports our findings implicating deficient eIF2-alpha signaling in DYT1 dystonia pathogenesis. Mutations in the PRKRA gene, which encodes an upstream eIF2-alpha kinase activator (FIG. 2a), cause DYT16 dystonia. (Zech, M., et al., (2015) *Mov. Disord* 30, 878-9; Vaughn, L. S. et al., (2015) *J. Biol. Chem.* 290, 22543-57; Lassot, I. et al., (2001) *Mol. Cell. Biol.* 21, 2192-202.) Functionally, the most common PRKRA mutation impairs the eIF2-alpha signaling pathway by delaying and reducing eIF2-alpha phosphorylation. (Frank, C. L., (2010) *J. Biol. Chem.* 285, 33324-33337.) Considering the intersection of this known cause of DYT16 with our findings newly implicating DYT1 dystonia in the eIF2-alpha pathway, it was hypothesized that eIF2-alpha pathway dysfunction might also contribute to instances of non-familial sporadic dystonia.

To investigate this possibility, exomic sequences from 20 patients presenting with sporadic dystonia were examined. (FIG. 5, panel c). 20 subjects with sporadic dystonia were exome sequenced. Results were compared to sequence from 573 control samples that were sequenced as part of other studies at Duke University. All studies were reviewed and approved by the Duke University Medical Center IRB, and all subjects gave written informed consent. Dystonia subjects were recruited at the Movement Disorders Center at Duke University Medical Center, Durham, N.C.

We collected 20 unrelated patients diagnosed with adult onset, sporadic dystonia (3 men and 17 women) with a mean age of dystonia onset of 47.4+/−9.59 years. A diagnostic workup was conducted by a Movement Disorders specialist to confirm the symptoms of dystonia with muscle involvement classified as focal, segmental, multifocal, or generalized. Only presumptive primary cases were recruited. Secondary dystonias associated with conditions such as Parkinson's disease or other neurodegenerative diseases were excluded. Cases suggestive of Mendelian inheritance were also excluded. A complete family and medical history was collected including common toxic exposures and medical comorbidities. Control samples were sequenced as part of other studies at Duke University Medical Center and were not enriched for (but not specifically screened for) dystonia or other neurological disorders.

Sequencing of DNA was performed at Duke University. Samples were exome sequenced using the Agilent All Exon 37 MB or 50 MB kit using Illumina GAIIx or HiSeq 2000 or 2500 sequencers according to standard protocols. All samples were processed using the same methods, as follows. The Illumina lane-level fastq files were aligned to the Human Reference Genome (NCBI Build 37) using the Burrows-Wheeler Alignment Tool (BWA). We then used Picard software (picard.sourceforge.net) to remove duplicate reads and process these lane-level SAM files, resulting in a sample-level BAM file that is used for variant calling. GATK was used to recalibrate base quality scores, realign around indels, and call variants. Variants were required to have a quality score (QUAL) of at least 20, a genotype quality (GQ) score of at least 20, at least 10× coverage, a quality by depth (QD) score of at least 2 and a mapping quality (MQ) score of at least 40. Indels were required to have a maximum strand bias (FS) of 200 and a minimum read position rank sum (RPRS) of −20. SNVs were restricted according to VQSR tranche (calculated using the known SNV sites from HapMap v3.3, dbSNP, and the Omni chip array from the 1000 Genomes Project): the cutoffs were a tranche of 99.9%. Variants were excluded if marked by EVS as being failures. Variants were annotated to Ensembl 73 using SnpEff. Only genetically European ethnicity samples were included in the analysis. Samples were screened with KING to remove second-degree or higher relatives; samples with incorrect sexes according to X:Y coverage ratios were removed, as were contaminated samples according to VerifyBamID. We used Analysis Tools for Annotated Variants (igm.cumc.columbia.edu) to identify coding variants that were found in at least 2 cases and 0 controls. The presence of mutations in ATF4 causing the P46L amino acid substitution were confirmed by Sanger sequencing.

The results of exome analysis are presented in FIG. 5, panel c. In these exomes, an analysis was performed to identify unique missense variants (relative to 573 controls) that were present in at least two cases. Genome-wide (i.e. agnostic to hypothesized mechanism), this analysis identified only 14 rare missense coding mutations that met this criterion (FIG. 5, panel c). Notably, one of these mutations was in the gene for the phospho-eIF2-alpha effector ATF4 (n.22:39917587C/T, rs111719524, p.P46L).

To evaluate the functional significance of this mutation, we tested the transcriptional activation activity of P46L ATF4 using a luciferase reporter driven by the ATF4-sensitive amino acid response element (AARE) (FIG. 5, panel d). As controls, we tested the activity of similarly expressed WT protein and a common ATF4 polymorphism, Q22P, which is present in approximately one third of the human population (exac.broadinstitute.org).

Constructs and Mutagenesis:

P46L and Q22P mutations were introduced into pRK/FLAG-ATF4 using a QuikChange Lightning site-directed mutagenesis kit (Agilent #210518) according to the manufacturer's instructions. Amino acid response element-sensitive Renillia luciferase (AARE-Rluc) was obtained from SwitchGear Genomics (#S900027). Constitutively expressed Cyperidina luciferase was obtained from New England Biolabs (pCMV-Cluc 2; #N0321S). pAARE-Rluc, pCMV-Cluc 2, and wildtype and mutant ATF4 sequences were confirmed by Sanger sequencing.

AARE Reporter Assay:

HEK293T cells were plated in 6-well plates (Corning #3506) at 500,000 cells per well in 2 mL HEK-T media [DMEM (Thermo Fisher #11995)+10%0/FBS+1× GlutaMAX+1× penicillin/streptomycin/amphotericin] and incubated at 37° C./5% CO2 overnight. The following day, cells were transfected with pAARE-Rhuc, pCMV-Cluc2, and empty vector or WT/mutant ATF4 as appropriate, using Lipofectamine2000 and OptiMEM according to the manufacturer's instructions (2.5 μg total DNA/well, 500 μL total volume/well). After 4 hours, transfection media was aspirated and replaced with fresh HEK-T media and cells were incubated at 37° ° C./5% CO2. 24 hours after transfection, 500 μL samples of conditioned media were transferred to a separate plate and stored at −80° C., and the remaining media was aspirated. Cells were then washed once with ice-cold PBS and lysed in 250 μL/well ice-cold lysis buffer [25 mM Tris-HCl/12.5 mM NaH2PO4/2 mM EGTA/1% Triton X-100/1× cOmplete Mini EDTA-free protease inhibitor]. Lysates were scraped, collected, clarified via centrifugation at 10,000 g for 10' at 4° C., and stored at −80° C. The following day, Clue activity in the conditioned media samples and Rluc activity in the clarified lysates was measured using BioLux Cyperidina Luciferase (NEB #E3309) and Pierce Renilla Luciferase (Thermo Fisher #16167) assay kits, respectively, according to the manufacturer's instructions. Data in (FIG. 5, panel d) are the average of 10 independent experiments.

The P46L mutation significantly reduced ATF4 activity, while no significant differences in activity were identified between Q22P and WT protein (FIG. 5, panel d). Western blot analysis of lysates prepared from the HEK293T cells described above further revealed that steady-state levels of P46L ATF4 were reduced in comparison to WT ATF4 control cDNA expressed under identical conditions (47.2% of WT) (FIG. 5, panels e, f). Data in (FIG. 5, panel e) are the average of 10 independent experiments.

Levels of P46L ATF4 were also significantly more sensitive to treatment with the proteasome inhibitor, MG132, suggesting that the P46L mutation increases its proteasomal degradation (FIG. 5, panel g). The data presented in FIG. 5, panel g reveals greater contribution of proteasomal degradation to P46L steady state levels as compared to WT ATF4. Cells expressing the FLAG-tagged ATF4 constructs indicated were treated with vehicle or MG132 (10 μM) for 2 hours, then lysed, blotted, and quantified. Data are the average of 8 independent experiments. Proteasomal degradation is a well-known, tightly regulated mechanism that controls cellular levels of ATF4. (Andreev, D. E. et al., (2015) *Elife* 4, e03971; Waugh, J. L. & Sharma, N., (2013) *Neurol. Clin.* 31, 969-86.) Therefore, this rare variant mutation may function by dysregulating this process.

Figure 6:
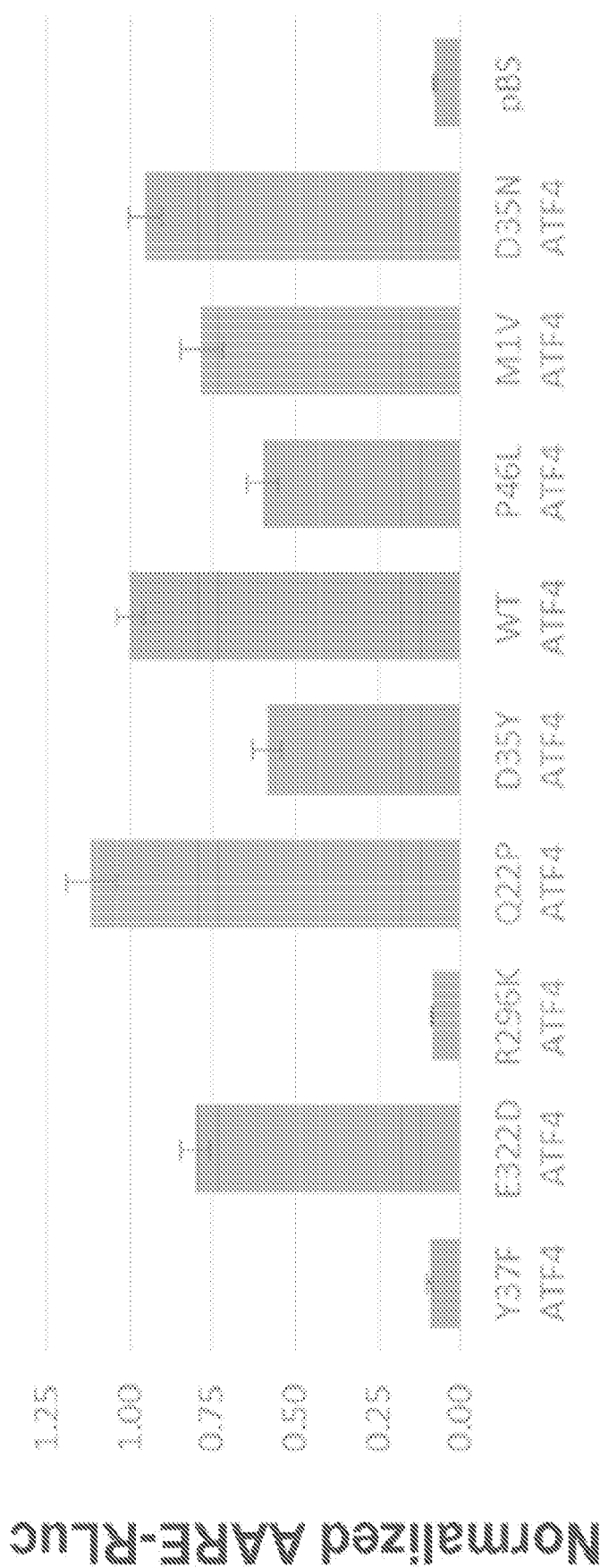
FIG. 6 shows additional sporadic mutations in dystonia patients with reduced ATF4 transcriptional activity relative to WT controls. Panel (a) shows transcriptional activation activity of mutant ATF4 constructs measured in HEK293T cells. Data was normalized such that luciferase activity after WT ATF4 transfection=1. *, p<0.05; ***, p<0.0005 by unpaired t test vs WT ATF4 condition. Panel (b) shows rare and common variants in ATF4 exon 1 identified by Sanger sequencing of 239 sporadic cervical dystonia patients; frequency, enrichment and predicted mutation severity shown at right.

Additional coding mutations identified in sporadic cervical dystonia cases (e.g. D35N, D35Y) showed significantly reduced activity, consistent with the direction of eIF2α pathway impairment that would be predicted by the effects described in DYT1 here and DYT16 (FIG. 6).

This series of experiments provides evidence that deficient eIF2-alpha signaling may contribute not only to rare inherited dystonias, but also to sporadic forms of dystonia.

Example 9: DYT1 Patient Cells have Increased Basal Levels of a Negative Feedback Regulator of the eIF2-Alpha Pathway PRKRA and ATF4 are components of the eIF2-alpha pathway, providing a mechanistic connection between eIF2-alpha signaling and dystonia. However, it remained unclear why eIF2-alpha signaling was disrupted in DYT1 (see Example 7; FIG. 5, panels a, b, supra). Because the ER stress-induced response of ATF4 translation was present but attenuated in DYT1 patient cells, it was hypothesized that DYT1 is caused by an increase in negative feedback mechanisms that attenuate 54bosphor-eIF2-alpha signaling.

Figure 7:
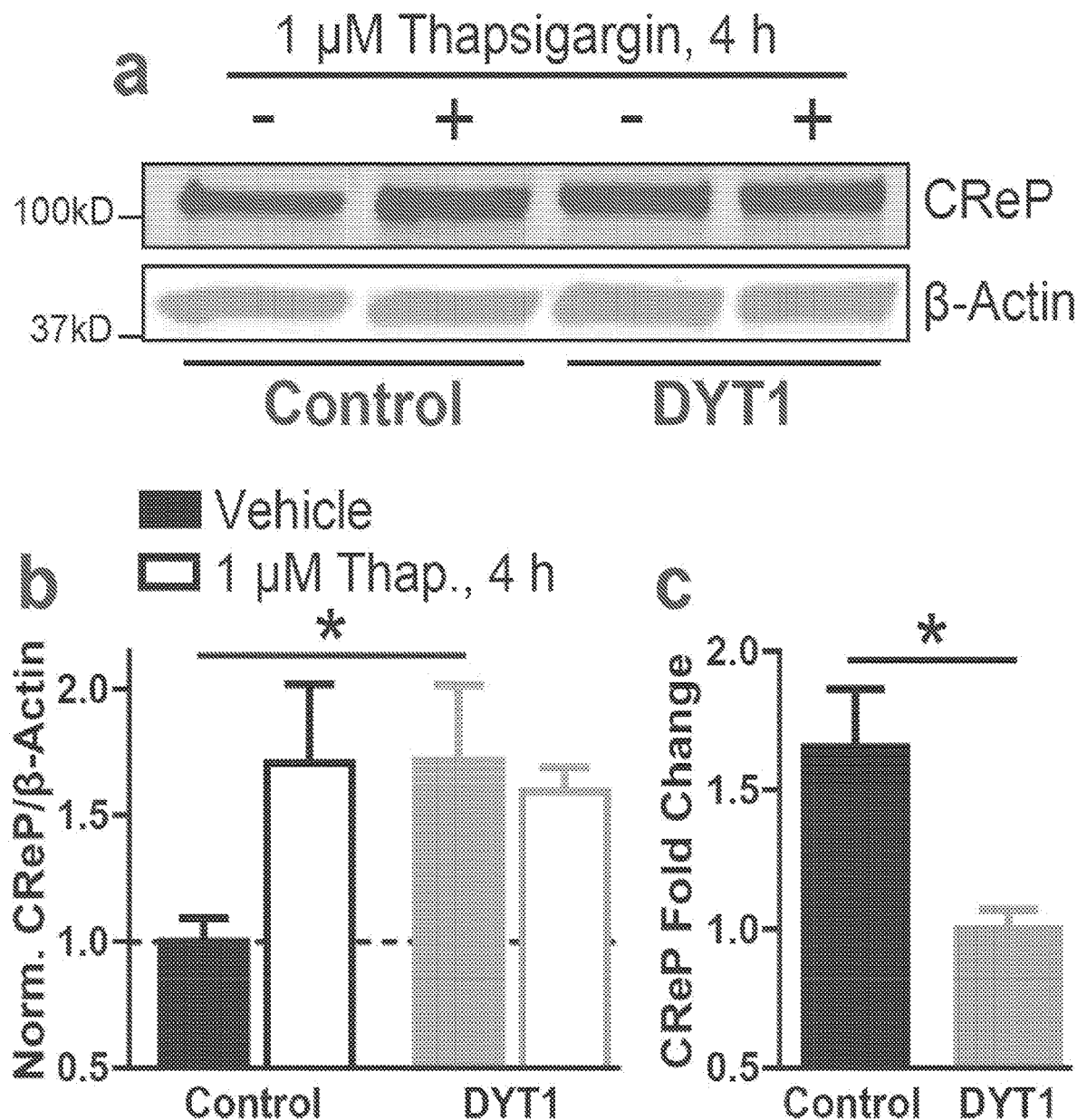
FIG. 7 shows that the eIF2-alpha phosphatase CreP is constitutively upregulated in DYT1 dystonia patients, and is not further upregulated in response to thapsigargin. Panel (a) shows representative Western blots for CreP with and without exposure to thapsigargin. Blots were re-probed for β-actin as a loading control. Panel (b) shows quantitation of replicates of the Western analyses presented in panel (a). N=3 independent control cell lines, and 4 independent DYT1 cell lines, 3 replicates each. *, p<0.05 by unpaired t test. All data are presented as means±S.E.M. CreP expression was normalized to β-actin expression. Panel (c) shows quantitation of the fold-change in CreP levels in control and DYT1 fibroblasts upon thapsigargin exposure (1 μM, 4 h). Panel (d) shows a model depicting the sites of eIF2-alpha pathway dysfunction in various forms of dystonia.
Figure 7:
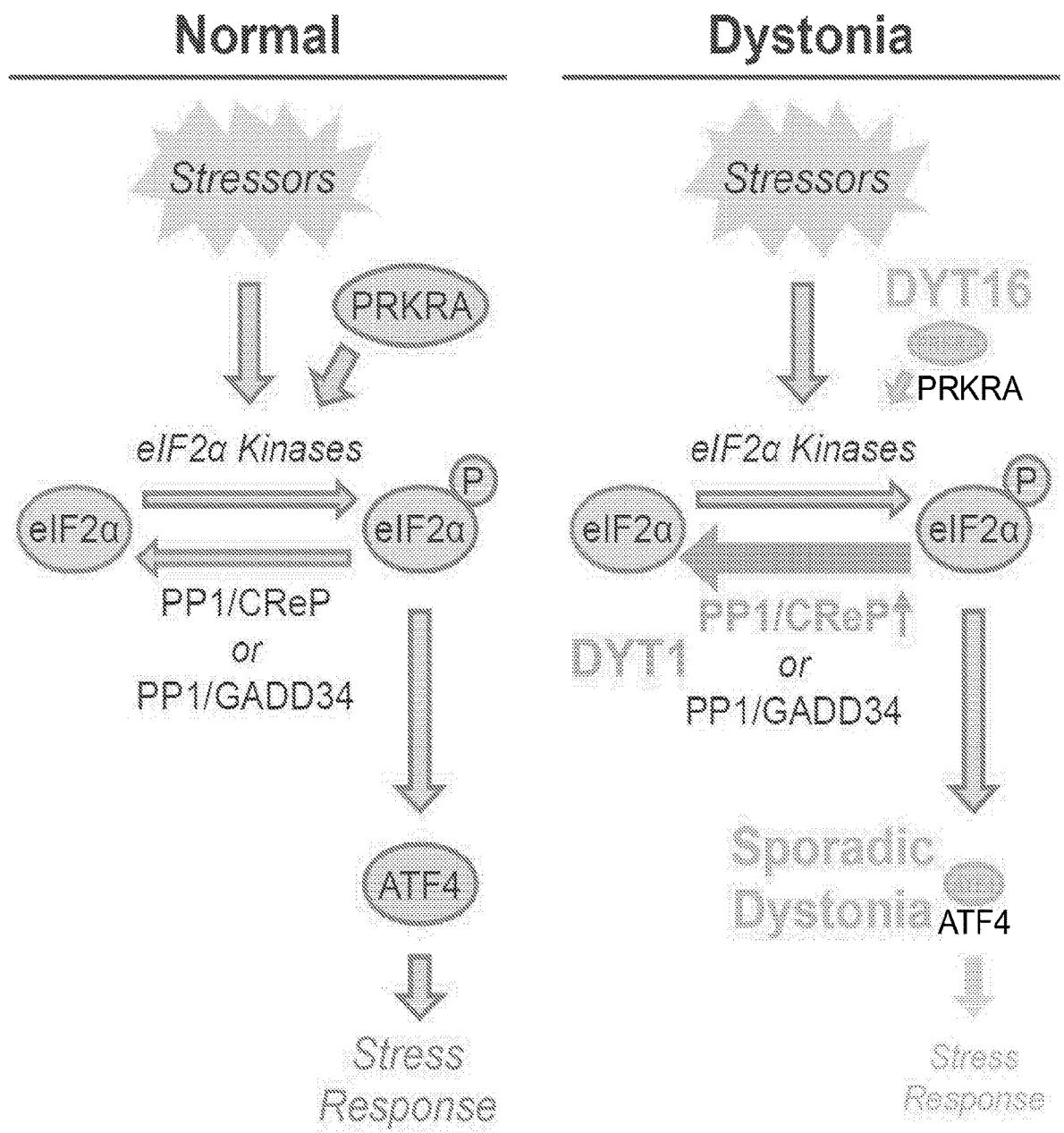

Two negative feedback proteins in the eIF2-alpha pathway are the eIF2-alpha phosphatase subunits, CreP and GADD34. A role for CreP was suggested by our pharmacological studies in which only salubrinal (which inhibits both CreP and GADD34) but not guanabenz (a specific inhibitor of GADD34) corrected delta E Torsin1a mislocalization. (See Example 4, supra.) We therefore measured levels of CreP under basal and ER-stressed conditions (FIG. 7). We determined at least two differences in CreP levels between fibroblasts from DYT1 patients and healthy controls. First, basal CreP levels were significantly higher in fibroblasts from DYT1 patients (FIG. 7, panels a, b), supporting our negative feedback hypothesis. Second, whereas CreP levels in normal fibroblasts robustly increased after treatment with thapsigargin as expected (FIG. 6c), CreP levels in DYT1 patient fibroblasts were unresponsive to the treatment (FIG. 7, panel c). As the increase in CreP levels in response to stress is regulated by 55hosphor-eIF2-alpha-dependent translation (Marciniak, S. J. & Ron, D, (2006) *Physiol. Rev.* 86, 1133-49), the failure of CreP levels to rise provides additional evidence that eIF2-alpha pathway signaling is deficient in DYT1.

These results support a mechanism in DYT1 dystonia whereby basally increased levels of negative feedback proteins impair acute, stress-responsive eIF2-alpha signaling (FIG. 7, panel d).

Example 10: Long Term Plasticity in the Cortico-Striatal Synapse by Modulation of eIF2-Alpha Pathway eIF2-alpha pathway dysfunction in a setting that does not involve exogenously expressed Torsin1a, mimicked the human genotype (heterozygosity), and involved the brain was examined. Dystonia is a brain disorder and although a disturbed ER stress response is a plausible mechanism for CNS disease, eIF2-alpha phosphorylation is also known to have brain-specific roles in long-term synaptic plasticity (Costa-Mattioli and Sonenberg, 2006, *Crit. Rev. Neurobiol.* 18, 187-95; Di Prisco et al., 2014, Nat. Neurosci. 17, 1073-82; Trinh and Klann, 2013, Neurobiol. Learn. Mem. 105, 93-9). Coincidentally, disrupted synaptic plasticity in basal ganglia circuitry has long been hypothesized as a disease mechanism for dystonia (reviewed in Peterson et al., 2010, Neurobiol. Dis. 37, 558-73). Furthermore, DYT1 mouse models have disruptions of long-term synaptic plasticity in the striatum—absence of type 5 metabotropic glutamate receptor (mGluR5)-dependent long-term synaptic depression (LTD) and increased long-term potentiation (LTP) magnitude (Martella et al., 2014, Neurobiol. Dis. 65, 124-32; Martella et al., 2009, Brain 132, 2336-49). In the hippocampus, eIF2-alpha phosphorylation is required for mGluR-dependent LTD (Di Prisco et al., 2014, Nat. Neurosci. 17, 1073-82) and shifts that reduce the amount of phosphorylated protein have been previously hypothesized to lower the threshold for LTP (Costa-Mattioli et al., 2007, Cell 129, 195-206). Thus, known brain-specific eIF2-alpha roles directly correlate with previously well-described alterations in DYT1 mouse model synaptic plasticity.

To directly test these predictions, whole-cell electrophysiology of striatal projection neurons was performed in acute brain slices to induce long-term depression in the presence of eIF2-alpha pathway-modulating drugs. Acute horizontal brain slices from the progeny of heterozygous ΔE Torsin1a knockin×homozygous Drd1a-tdTomato mice (age P15-21) were prepared largely as described in (Trusel et al., 2015, Cell Rep. 13, 1353-65). LTD was induced as in Trusel et al., 2015, with modifications.

Animals and Slice Preparation

Heterozygous delGAG Torsin1a knockin mice (courtesy of Dr. W. Dauer, University of Michigan) were crossed with homozygous Drd1a-tdTomato mice (Jackson Labs) and the progeny was used at postnatal day 15-21 for experiments. Mice were anesthetized and intracardially perfused with high-sucrose solution (194 mM sucrose, 30 mM NaCl, 4.5 mM KCl, 2 mM MgCl2, 200 μM CaCl2, 1.2 mM NaH2PO4, 26 mM NaHCO3, and 10 mM glucose, saturated with 95% O2 and 5% CO2). Animals were then decapitated, their brains dissected, and 300 μm horizontal slices were cut on a Leica VT1200S vibratome. Slices were then transferred to artificial cerebrospinal fluid (ACSF; 124 mM NaCl, 2.5 mM KCl, 2 mM MgCl2, 2 mM CaCl2, 26 mM NaHCO3, 1.2 mM NaH2PO4, and 10 mM glucose, saturated with 95% O2 and 5% CO2, pH 7.4, 300 mOsm/l) to equilibrate for at least 1 h.

Recording and Analysis

Single slices were transferred to a recording chamber and superfused continuously with ACSF containing 50 μM picrotoxin at 32° C. and 3-4 mL/min. Neurons were visualized using infrared differential interference microscopy. Micropipettes were pulled (Narishige) from borosilicate glass tubes (King Precision Glass) for a final resistance of 2.5-4.5 MΩ when filled with internal solution (130 mM KSO4CH4, 5 mM KCl, 5 mM NaCl, 100 μM EGTA, 10 mM HEPES, 2 mM MgCl2, 50 μM CaCl2, 2 mM ATP-Mg, 400 μM GTP-Na, pH 7.3, 290 mOsm/l). Evoked excitatory postsynaptic potentials (EPSPs) were recorded in the dorsolateral striatum, while stimulating every 30 seconds with a concentric bipolar electrode (FHC) in cortical layer V (see Trusel et al., Cell Reports, 2015). To induce long-term depression, 4 trains of 100 Hz stimulation (every 10 s) were applied while the postsynaptic cell was depolarized to −50 mV. Baseline EPSPs were recorded for at least 10 min or until a stable baseline was reached. Data were acquired by pClamp v10 and analyzed using Clampfit v10.4, Origin v8.0, and GraphPad Prism v6.

Figure 8:
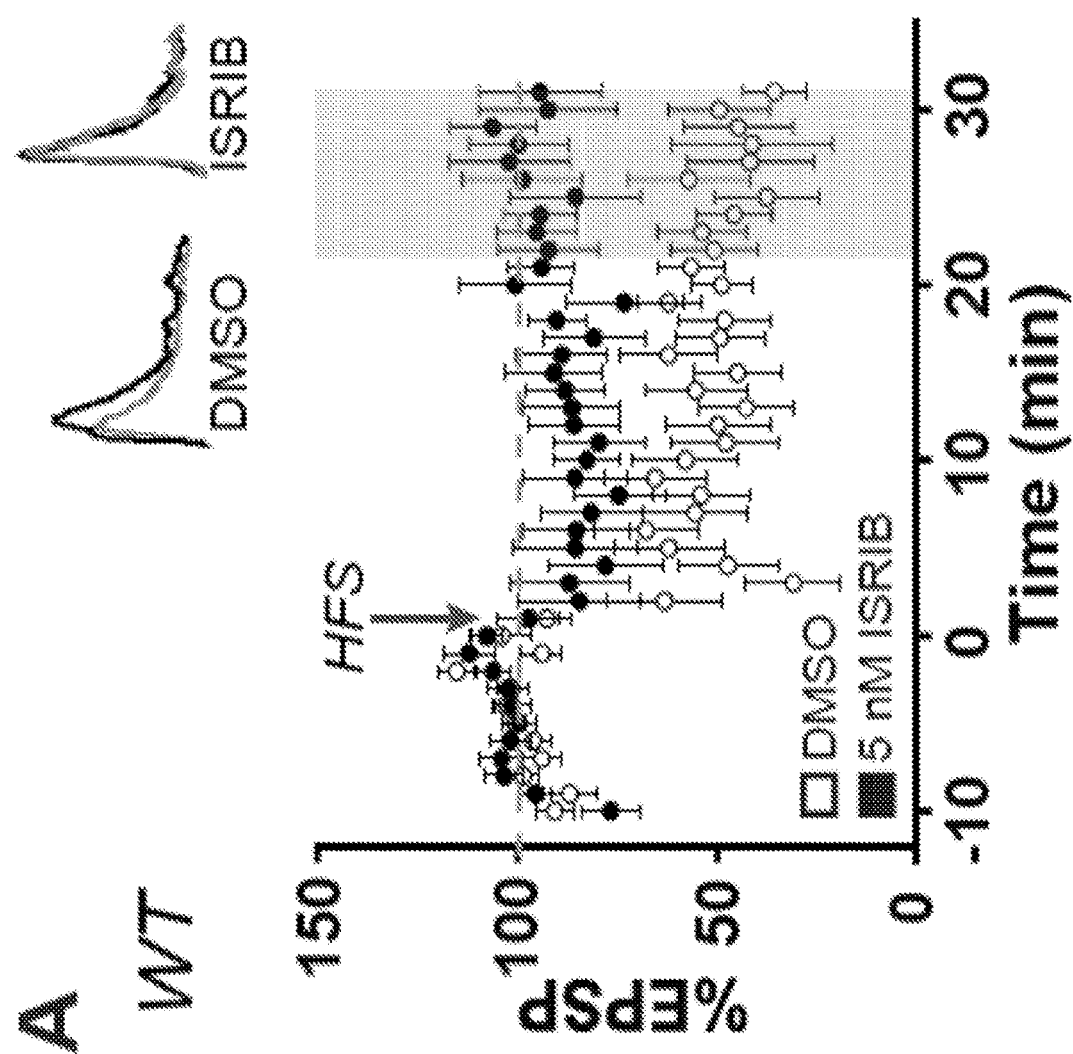
FIG. 8 shows restoration of long term plasticity in the cortico-striatal synapse by modulation of eIF2-alpha pathway. Panel (a) shows a time course of Long term depression (LTD) in cortico-striatal synapse induced by 4 trains 100 Hz on V layer of cortex (see Example 10) in WT mice (vehicle; white dots), and when incubated with ISRIB (5 nM, 1 hr.) (black dots; P=0.015). Panel (h) shows the temporal course in delta-E-TorsinA mice treated with vehicle; (white dots), or sa1003 (20 mM; shaded dots; p=0.0274). In each of panels (a) and (b), black traces above the graph are EPSPs recorded before HFS, gray traces are EPSPs recorded after 21 min post HFS. Panel (c) shows mean magnitude of LTD in (A) and (B). Data in blue shaded box in panels (A) and (B) (minutes 21-31) were averaged. *, p<0.05 by Mann-Whitney U-test. Data are means±S.E.M.
Figure 8:
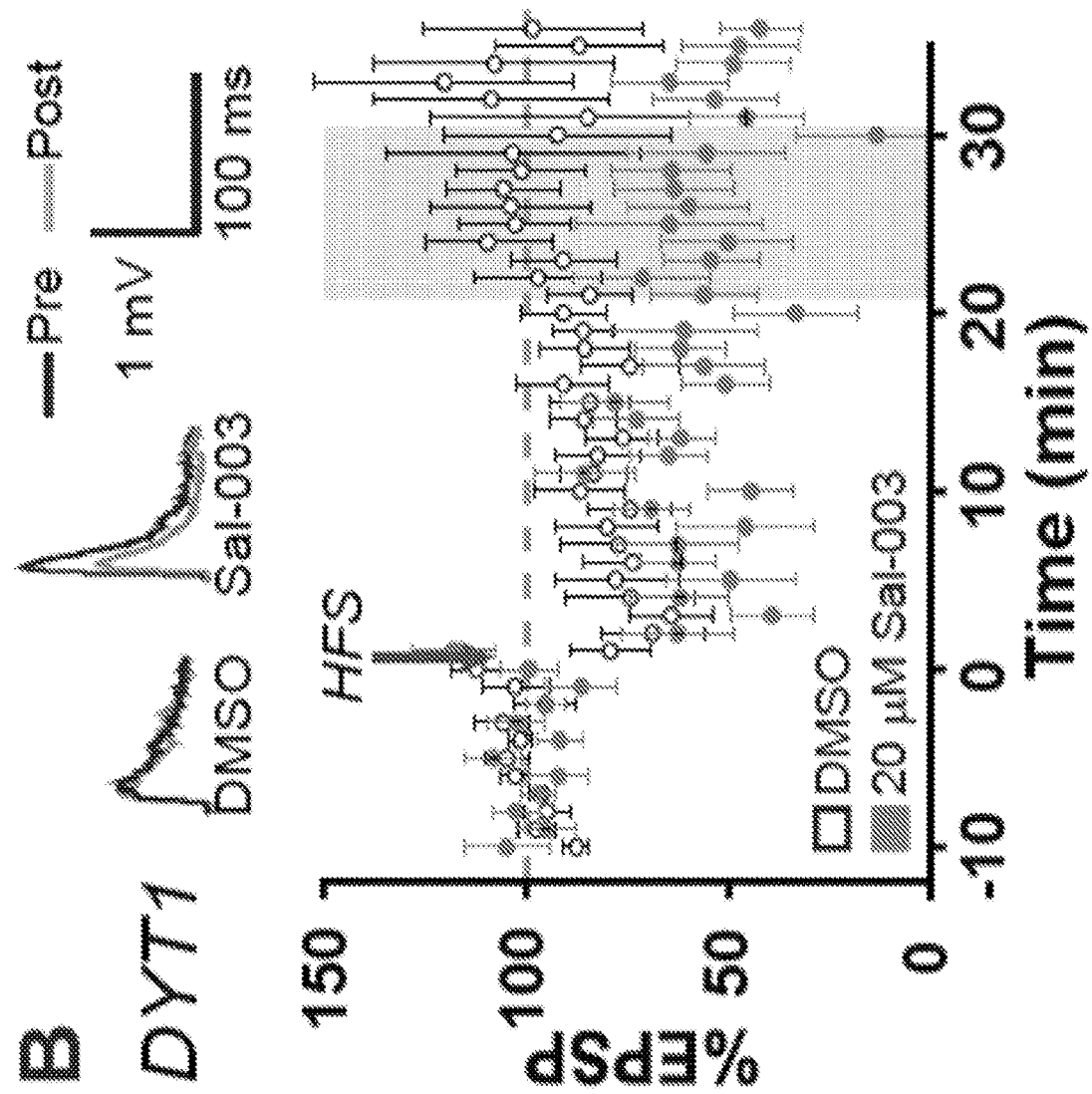
Figure 8:
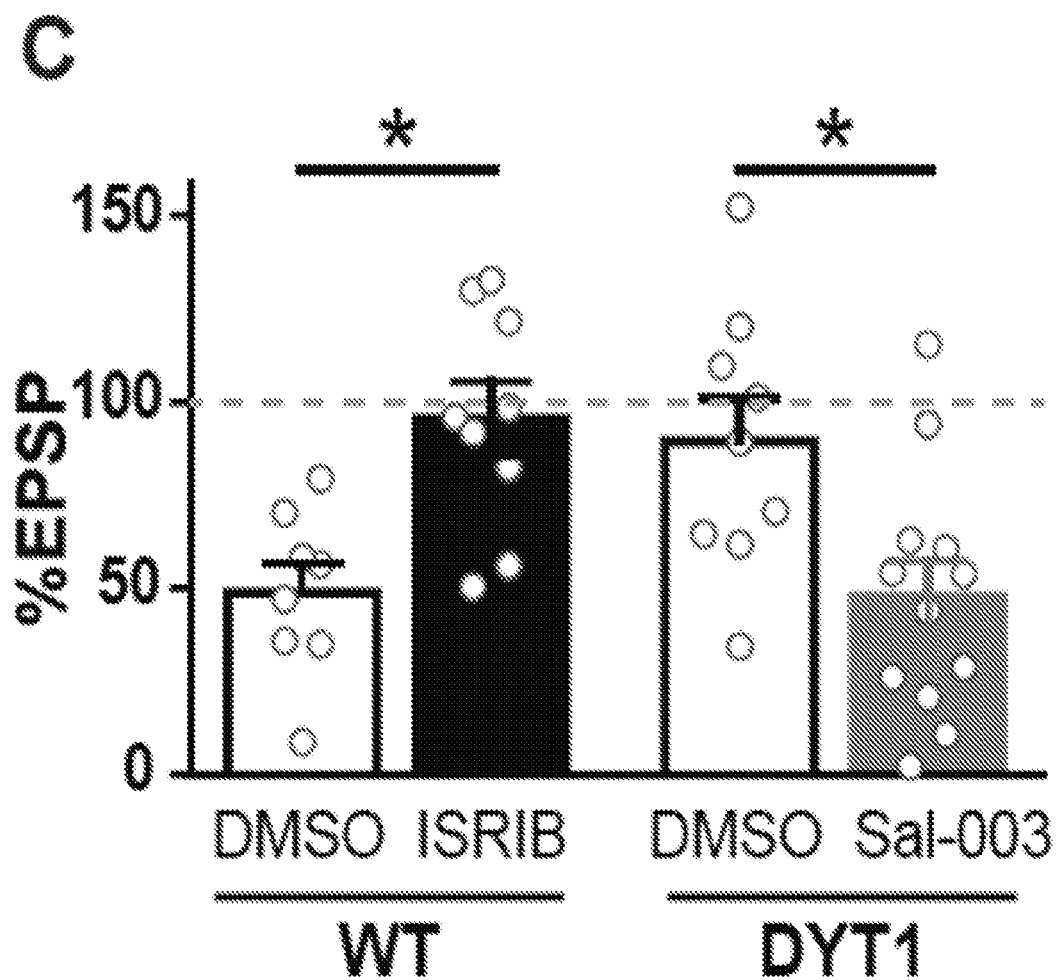

Results eIF2-alpha signaling was assessed to determine if it normally plays a role in striatal mGluR5 LTD. Pre-incubation with ISRIB (5 nM), a blocker of eIF2-alpha pathway signaling, robustly inhibited LTD in WT brain slices (FIG. 8, panel A). Additionally, it was notable that while control vehicle-treated slices display a range of responses, none were greater than the baseline amplitude; however, in the presence of ISRIB, potentiating responses were now observed.

To test whether augmenting eIF2-alpha signaling in DYT1 model mice would normalize synaptic plasticity, brain slices from mice heterozygous for the DYT1 knockin mutation (delGAG) were treated with 20 μM Sal-003, an inhibitor of eIF2α phosphatases. In comparison to vehicle-treated brain slices, Sal-003 restored long-term depression (FIG. 8, panel B) and to levels that once again approximate the normal magnitude (FIG. 8, panel B and C). These observations demonstrate that eIF2-alpha signaling normally plays a role in brain processes that are disrupted in DYT1 model mice and that acute enhancement of eIF2-alpha phosphorylation is sufficient to restore normal brain plasticity to disease model mice.

Figure 10:
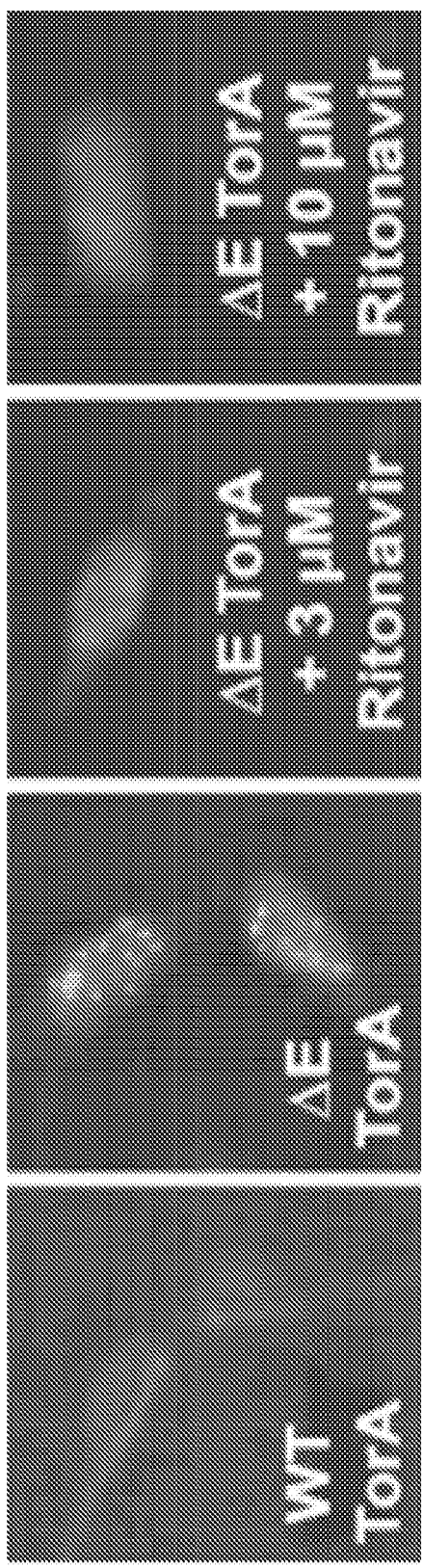
FIG. 10 shows Torsin1a mis-localization is restored in cells treated with ritonavir.

Example 11: Anti-Retroviral "Avir" Drugs are Useful for Treating Dystonia, and Dystonia Associated Disorders The HIV protease inhibitors ritonavir, lopinavir, saquinovir, nelfinavir, and indinavir corrected TorsinA localization in a dose-dependent fashion, with no cellular toxicity observed at effective doses (Table 5, FIG. 10). Furthermore, in orthogonal assays, ritonavir, lopinavir, and saquinovir corrected secretory deficits (Table 5), a phenotype also present in Dyt1 patient-derived fibroblasts. (Cao, S. et al. (2010) *Dis. Model. Mech.* 3, 386-96.) Subsequent testing of additional HIV protease inhibitors supported the activity of this class of compounds and generated favorable structure-activity relationship (SAR) data from which to design improved compounds (Tables 5 and 6). The results with a subset of compounds were also observed in a Luciferase secretion assay (Tables 5 and 6).

TABLE 5

Delta-Torsin1a mislocalization assay and C.Luc. Sectretion Assays

| Collected Activity Data | ΔE TorsinA Mislocalization Assay | | | C.Luc. Secretion Assay | |
|---|---|---|---|---|---|
| | Localization EC50 (μM) | Localization Max Efficacy | Cytotoxicity EC50 (μM) | Secretion EC50 (μM) | Secretion Max Efficacy |
| Ritonavir | 4.11 | 87% | None | 3.72 | 49% |
| Lopinavir | 4.69 | 70% | 37.2 | 0.98 | 177% |
| Saquinavir | 9.41 | 88% | 23.6 | 8.09 | 34% |
| Nelfinavir | 3.49 | 80% | 6.05 | No Activity | |
| Indinavir | 26.5 | 114% | 35.2 | No Activity | |
| Atazanavir | No Activity | | None | No Activity | |
| Amprenavir | No Activity | | None | No Activity | |
| Darunavir | No Activity | | None | No Activity | |

Table 6 presents additional data showing that the indicated HIV protease inhibitors correct DYT1 phenotypes. % DYT1 Pathology is according to methods for high-throughput assay screening analysis described above, in which % cells with punctate EGFP signal following EGFP-Torsin1a protein expression are measured as "% selected cells." Efficacy and Max Response refer to activity on a normalized scale in which the % selected cells in the cell line expressing WT-TorsinA is set to 0% and the %selected cells in the cell line expressing DYT1 Mutant Torsin1a is set to 100% pathology. Efficacy is calculated as the magnitude of the pathology correction relative to the mutant Torsin1a pathology. For example an efficacy=−100% would be equivalent to the WT TorsinA phenotype, and 0% would be equivalent to the Mutant TorsinA phenotype. CCv2 refers to the dose response Curve Class annotation, and AC refers to Active Concentration. (See Inglese, J., et al. (2006), PNAS, 103: 11473-11478.)

TABLE 6

HIV protease inhibitors correct DYT1 phenotypes

| | | % pathology | | | | Cytotox | | |
|---|---|---|---|---|---|---|---|---|
| Sample Name | CC-v2 | AC50 (μM) | Efficacy | Max Resp | CC-v2 | AC50 (μm) | Efficacy | Max Resp |
| Viracept | −2.3 | 5.26 | −119.39 | −94.06 | −1.1 | 10.49 | −106.32 | −97.72 |
| Saquinavir mesylate | −1.1 | 8.33 | −85.98 | −84.62 | −2.1 | 20.93 | −105.74 | −96.01 |
| Indinavir sulfate | −2.1 | 29.57 | −114.60 | −97.76 | −3 | 37.22 | −80.64 | −67.80 |
| Amprenavir | 4 | | | | 4 | | | |
| Ritonavir | −1.1 | 2.96 | −92.96 | −82.60 | 4 | | | |
| Lopinavir | −1.3 | 4.69 | −69.97 | −89.03 | −3 | 37.22 | −69.87 | −55.19 |
| Darunavir | 4 | | | | 4 | | | |
| Atazanavir | 4 | | | | 4 | | | |
| Nelfinavir mesylae hydrate | −1.1 | 2.70 | −75.26 | −92.46 | −1.1 | 6.05 | −98.05 | −95.64 |
| Des-hydroxy Lopinavir | −3 | 8.33 | −82.44 | −33.96 | −2.2 | 20.93 | −77.66 | −66.67 |

Figure 11:
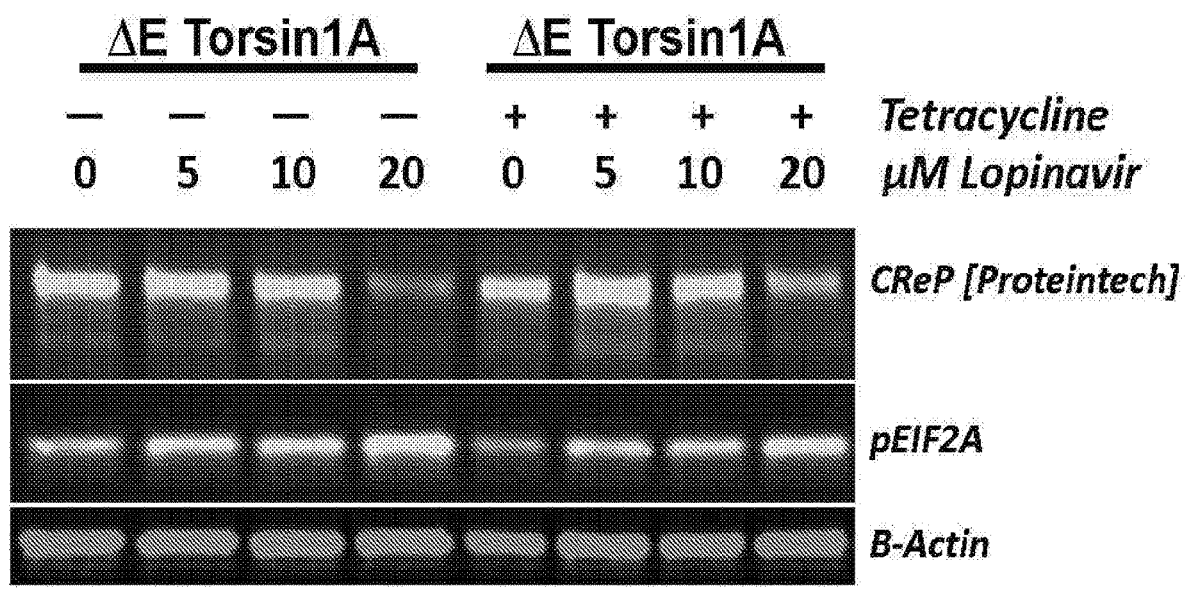
FIG. 11 shows that lopinavir treatment in EGFP-delta-E Torsin1a Flip-In TREx 293 cells decreases CReP abundance. Panel (a) shows Western blot analysis of CreP and eIF2-alpha in WT and delta-E Torsin1a cells exposed to increasing concentration of Lopinavir. Blots were probed for β-actin as a loading control. Panel (b) shows quantitation of CreP protein levels, and panel (c) shows quantitation of eIF2-alpha protein levels, in WT and delta-E Torsin1a cells exposed to varying doses of lopinavir.
Figure 11:
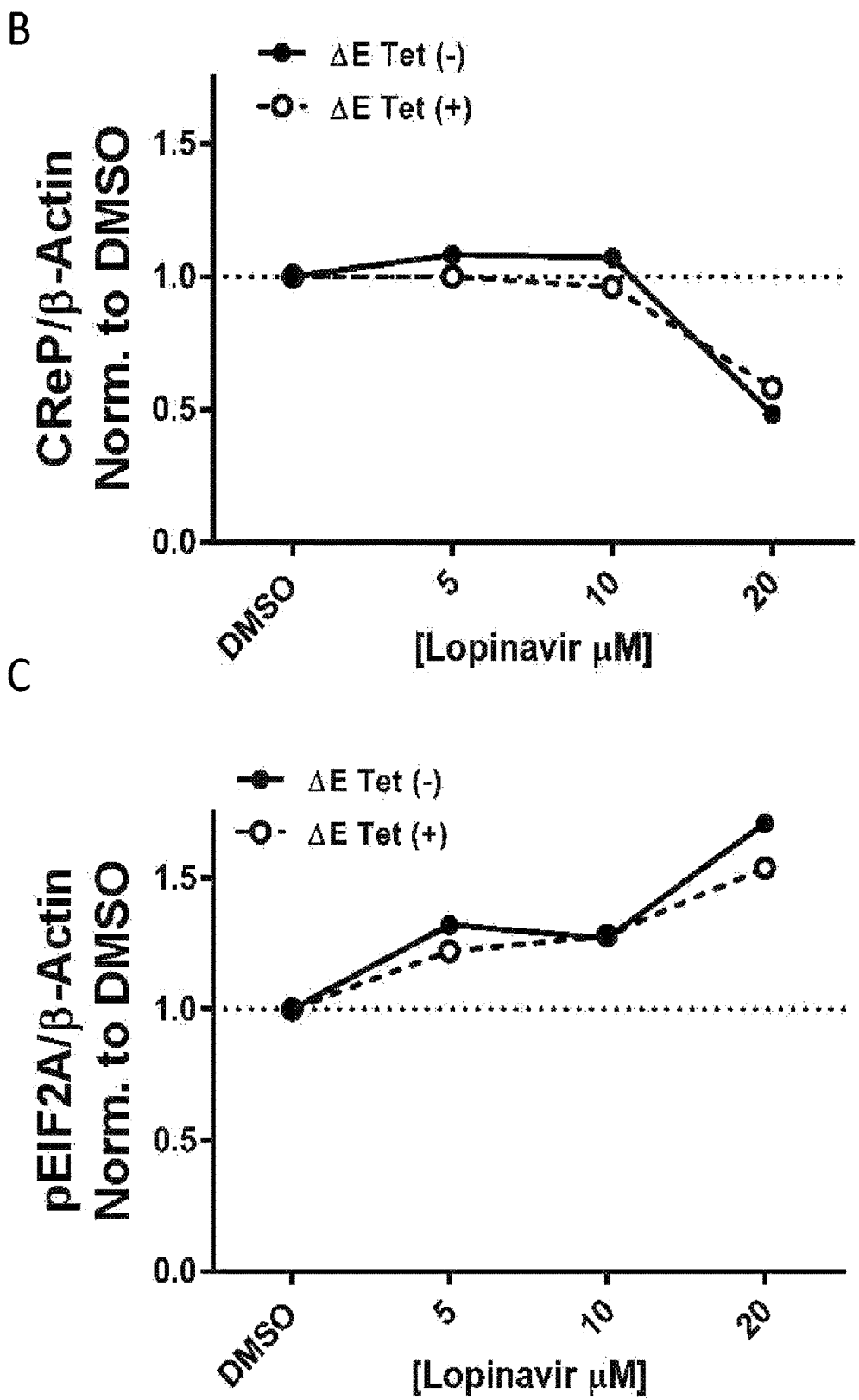

Western blot analyses were conducted to determine the effect of Lopinavir on ATF4, CreP, pEIF2-alpha, and β-actin abundance in EGFP-ΔE Torsin1a expression assay cell lines. The HIV protease inhibitor Lopinavir increases phosphorylation of EIF2-alpha and ATF4 abundance in a dose dependent manner through down-regulation of steady state levels of the EIF2-alpha protein phosphatase 1 regulatory subunit, CreP, as determined in the EGFP-ΔE Torsin1a expression assay cell line (FIG. 11). This down regulation of CreP is in keeping with the HIV protease inhibitor mediated CreP regulation. (See De Gassart et al. PNAS 2015.)

The invention claimed is:

1. A method of treating DYT1 dystonia in a subject, the method comprising administering one or more of an HIV aspartyl protease inhibitor, wherein the one or more HIV aspartyl protease inhibitor is ritonavir, lopinavir, saquinavir, nelfinavir, or indinavir, or a combination thereof.

2. The method of claim 1, wherein the subject is a child.

3. The method of claim 1, wherein the one or more HIV aspartyl protease inhibitor is ritonavir.

4. The method of claim 1, wherein the one or more HIV aspartyl protease inhibitor is lopinavir.

5. The method of claim 1, wherein the one or more HIV aspartyl protease inhibitor is saquinavir.

6. The method of claim 1, wherein the one or more HIV aspartyl protease inhibitor is nelfinavir.

7. The method of claim 1, wherein the one or more HIV aspartyl protease inhibitor is indinavir.

8. A method of correcting delta-E Torsin1A mislocalization in a cell, the method comprising contacting the cell with one or more of an HIV aspartyl protease inhibitor, wherein the one or more HIV aspartyl protease inhibitor is ritonavir, lopinavir, saquinavir, nelfinavir, or indinavir, or a combination thereof.

9. The method of claim 8, wherein the cell is a human cell.

10. The method of claim 8, wherein the one or more HIV aspartyl protease inhibitor is ritonavir.

11. The method of claim 8, wherein the one or more HIV aspartyl protease inhibitor is lopinavir.

12. The method of claim 8, wherein the one or more HIV aspartyl protease inhibitor is saquinavir.

13. The method of claim 8, wherein the one or more HIV aspartyl protease inhibitor is nelfinavir.

14. The method of claim 8, wherein the one or more HIV aspartyl protease inhibitor is indinavir.

\* \* \* \* \*